(12) United States Patent
Najib et al.

(10) Patent No.: US 7,943,661 B2
(45) Date of Patent: *May 17, 2011

(54) SUBSTITUTED 1,3-DIPHENYLPROP-2-EN-1-ONE DERIVATIVES AND PREPARATION AND USES THEREOF

(75) Inventors: Jamila Najib, Santes (FR); Karine Caumont-Bertrand, Frelinghien (FR)

(73) Assignee: Genfit, Loos (FR)

( * ) Notice: Subject to any disclaimer, the term of this patent is extended or adjusted under 35 U.S.C. 154(b) by 1270 days.

This patent is subject to a terminal disclaimer.

(21) Appl. No.: 10/520,079

(22) PCT Filed: Jul. 8, 2003

(86) PCT No.: PCT/FR03/02127
§ 371 (c)(1),
(2), (4) Date: Apr. 22, 2005

(87) PCT Pub. No.: WO2004/005233
PCT Pub. Date: Jan. 15, 2004

(65) Prior Publication Data
US 2005/0176808 A1    Aug. 11, 2005

(30) Foreign Application Priority Data

Jul. 8, 2002 (FR) .................................. 02 08571

(51) Int. Cl.
C07D 335/06 (2006.01)
(52) U.S. Cl. .......................................... 514/432; 549/23
(58) Field of Classification Search .................. None
See application file for complete search history.

(56) References Cited

U.S. PATENT DOCUMENTS

| | | | |
|---|---|---|---|
| 3,558,612 A | 1/1971 | Kuhn et al. | |
| 3,994,955 A | 11/1976 | Sprenger | |
| 4,190,671 A | 2/1980 | Vanstone et al. | |
| 4,656,305 A | 4/1987 | Vanstone et al. | |
| 5,109,025 A | 4/1992 | Satoh et al. | |
| 5,276,058 A | 1/1994 | Satoh et al. | |
| 5,326,670 A * | 7/1994 | Kotachi et al. | 430/296 |
| 5,523,302 A | 6/1996 | Cain et al. | |
| 7,385,082 B2 | 6/2008 | Delhomel et al. | |
| 7,547,729 B2 * | 6/2009 | Caumont-Bertrand et al. | |
| 7,566,737 B2 | 7/2009 | Delhomel | |
| 7,632,870 B2 | 12/2009 | Najib et al. | |
| 2005/0171149 A1 * | 8/2005 | Najib et al. | 514/312 |
| 2005/0176808 A1 | 8/2005 | Najib et al. | |
| 2007/0032543 A1 * | 2/2007 | Delhomel et al. | 514/432 |

FOREIGN PATENT DOCUMENTS

| | | |
|---|---|---|
| DE | 43 27 365 | 2/1995 |
| EP | 0 947 511 | 10/1999 |
| EP | 1 254 658 | 11/2002 |
| EP | 1 254 759 | 11/2002 |
| FR | 2 248 829 | 5/1975 |
| FR | 2 383 157 | 8/1977 |
| FR | 78 06279 | 10/1978 |
| FR | 2 841 900 | 1/2004 |
| JP | 52078856 | 7/1977 |
| WO | WO 95/05358 | 2/1995 |
| WO | WO 98/27970 | 7/1998 |
| WO | WO 00/23073 | 4/2000 |
| WO | WO 01/98291 | 12/2001 |
| WO | 2004/005233 | 1/2004 |
| WO | 2004/005243 | 1/2004 |

OTHER PUBLICATIONS

Byrn, et al. "Solid State Chemistry of Drugs", 2d ed., SSCI, Inc., Ch. 10 Polymorphs, pp. 232-247 (1999).*
Pond et al., caplus an 1906:1190.*
Pond et al., caplus an 1906:1190 (1906).*
Shibata, "Anti-tumorigenic Chalcones", Stem Cells, vol. 12, 1994, pp. 44-52.
Dimmock et al, "Bioactivities of Chalcones", Current Medicinal Chemistry, Bentham Science Publishers, vol. 6, No. 12, 1999, pp. 1125-1149.
L'ebreau et al, "Antioxidant Properties of Di-Tert-Butylhydroylated Flavonoids", Free Radical Biology and Medicine, vol. 29, No. 9, Nov. 1, 2000, pp. 900-912.
Mukherjee et al, "Synthetic and Biological Activity Evaluation Studies on Novel 1,3-Diarylpropenones", Bioorganic & Medicinal Chemistry, vol. 9, No. 2, 2001, pp. 337-345.
Cheng et al, "Broussochalcone A, a potent antioxidant and effective suppressor of inducible nitric oxide synthase in lipopolysaccharide-activated macrophages", Biochemical Pharmacology, vol. 61, No. 8, Apr. 15, 2001, pp. 939-946.
Cheng et al, "Antioxidant properties of butein isolated from Dalbergia odorifera", Biochemica et Biophysics Acta, vol. 1392, No. 2/3, Jun. 15, 1998. pp. 291-299.
Rajakumar et al, "Antioxidant Properties of Phenyl Styryl Ketones", Free Radical Research, vol. 22, No. 4, 1995, pp. 309-317.
Arty et al, "Synthesis of benzylideneacetophenones and their inhibition of lipid peroxidation", European Journal of Medicinal Chemistry 2000 France, vol. 35, No. 4, 2000, pp. 449-457.
Database Chemical Abstracts Service, XP002236011, abstract & Zhang et al, "Antioidation of Peurperia lobate isoflavones", Tongji Yike Dauxe Xeubao, vol. 26, No. 5, 1997, pp. 340-342. Stoll et al, Chalcone derivatives antagonize interactions between the human oncoprotein NDM2 and p53, Biochemistry, United States Jan. 16, 2001, vol. 40, No. 2, Jan. 16, 2001, pp. 336-344.
Database Chemical Abstracts Service, XP002262904, abstract & Shi et al, "Synthesis of ethyl Flavone(or chalcone)oxyllsobutyrate and its derivatives as potential antilipidemic agents", Taiwan Yaoxue Zazhi, vol. 27, No. 1-2, 1975, pp. 12-16.
Lebeau et al, "Beneficial effects of different flavonoids, on functional recovery after ischemia and reperfusion in isolated rat heart", Bioorganic & Medicinal Chemistry Letters, vol. 11, No. 1, Jan. 8, 2001, pp. 23-27.
Patent Abstracts of Japan vol. 014, No. 126, Mar. 9, 1990 & JP 02 003670 A Jan. 9, 1990.
Halliwell, "Oxidants and the central nervous system: some fundamental questions. Ix oxidant damage relevant to Parkinson's disease, Alzheimer's disease, traumatic injury or stroke?", Acta Neurologica Scandinavica, Supplementum, Denmark 1989, vol. 126, 1989, pp. 23-33.

(Continued)

Primary Examiner — Sun Jae Y Loewe
(74) Attorney, Agent, or Firm — Nixon & Vanderhye P.C.

(57) ABSTRACT

The invention concerns novel substituted 1,3-diphenylprop-2-en-1-one derivatives, pharmaceutical compositions comprising same, their therapeutic uses, in particular for treating cerebral ischemia. The invention also concerns a method for preparing said derivatives.

17 Claims, 8 Drawing Sheets

OTHER PUBLICATIONS

Office Action dated Feb. 26, 2009, issued in connection with U.S. Appl. No. 10/520,078.
King, Frank D. "Bioisosteres, Conformational Restriction, and Prodrugs—Case History: An Example of a Conformational Restriction Approach", Medical Chemistry: Principles and Practice, 1994, Chapter 14, pp. 206-225.
Byrn, et al, "Solid State Chemistry of Drugs", 2$^{nd}$ ed., SSCI, Inc., Chapter 10, p. 232-247, 1999.
Sogawa et al, "3,4-Dihydroxychalcones as Potent 5-Lipoxygenase and Cyclooxygenase Inhibitors", Journal of Medicinal Chemistry, American Chemical Society, Washington, US, vol. 36, No. 24, 1993, pp. 3904-3909.
Nakamura et al, "Synthesis and Biological Activities of Fluorinated Chalcone Derivativs", Bioorganic & Medicinal Chemistry, Elsevier Science Ltd, GB, vol. 10, No. 3, Mar. 2002, pp. 699,706.
Calliste et al, "Chalcones: Structural Requirements for Antioxidant, Estrogenic and Antiproliferative Activities", Anticancer Research, Helenic Anticancer Institute, Athens, GR, vol. 21, No. 6A, 2001, pp. 3949-3956.
Furman et al, "Di-tert-Butylhydroxylated Flavonoids Protect Endothelial Cells Against Oxidized LDL-Induced Cytotocity", Journal of Biochemical and Molecular Toxicology, Wiley, New York, NY, US, vol. 15, No. 5, 2001, pp. 270-278.
Lim et al, "Synthesis of flavonoids and their effects on aldose reductase and sorbitol accumulation in streptozotocin-induced diabetic rat tissues", Journal of Pharmacy and Pharmacology, London, GB, vol. 53, No. 5, May 2001, pp. 653-668.
U.S. Appl. No. 10/520,079, filed Apr. 2005, Najib et al.
U.S. Appl. No. 11/493,040, filed Jul. 2006, Delhomel et al.
Patent Abstracts of Japan, vol. 018, No. 415, Aug. 4, 1994 & JP 06 122623 A, May 6, 1994.
Patent Abstracts of Japan, vol. 012, No. 209, Jun. 15, 1988 & JP 63 010720 A, Jan. 18, 1988.
Haraguchi et al, "Antioxidative and Superoxide Scavenging Activities of Retrochalcones in Glycyrrhiza Inflata", Bioorganic & Medicinal Chemistry, Elsevier Science Ltd, GB, vol. 6, No. 3, Mar. 1998, pp. 339-347.
Chemical Abstracts Service XP002236041, abstract & Oganesyan et al, "Study of structure-activity (A) interrelations in the flavonoid series. I. Synthesis of chalcome derivatives and quantitative SA analysis", Khimiko-Farmatseviicheskii Zhurnal, vol. 20, No. 6, 1986, pp. 696-702.
Hsu et al, Structure-Activity Relationships of Substituted Flavonoids. (I), Taiwan-Kexue-Formosanscience, Taipei, TW, vol. 27, No. 1/2, 1973, pp. 23-26.
Szajda et al, "New alkoxycarbonylalkyl oxychalcones and their alpha, beta-dibromo derivatives of potential antimicrobial activity", Die Pharmazie, Germany, East Mar 1989, vol. 44, No. 3, Mar. 1989. pp. 190-191.
Stoll et al, "Chalcone derivatives antagonize interactions between the human oncoprotein MDM2 and p53", Biochemistry, American Chemical Society. Easton, PA, US, vol. 40, No. 2, Jan. 16, 2001, pp. 336-344.
Database, Chemical Abstracts Service, XP002271329, abstract & Shi et al, "Synthesis of ethyl flavone (or chalcone) oxyisobutyrate and its derivatives as antilipemic agents", Taiwan Yaoxue Xazhi, vol. 27, No. 1-2, 1975, pp. 12-16.
Database Chemical Abstracts Service, XP002271330, abstract & Palanowski et al, "Synthesis of potentiao vasoactive compounds. I. phenylacrylophenone derivatives", Acta Poloniae Pharmaceutica (English Translation), vol. 24, No. 6, 1967, pp. 567-574.
Database, Chemical Abstracts Service, XP002271331, abstract & JP 54 019947 A (Taisho Pharmaceutical Co.) Feb. 15, 1979.
Database, Chemical Abstracts Service, XP002271332, abstract & Safak et al, "Chalcones. II. Synthesis of some chalcone derivatives and their antifungal activity against Candida albicans", Fabad Farmasotik Bilimler Dergisi, vol. 8, No. 2, 1983, pp. 80-88.
Database, Chemical Abstracts Service, XP002271333, abstract & JP 05 255655 A, (Kanebo Ltd), Oct. 5, 1993.
Database, Chemical Abstracts Service, XP002271334, abstract & Sun et al, "Studies on flavonoids. VIIII. Synthesis of 7-substituted flavones and 2',4-dihydroxy-3-methoxy-4'-substituted chalcones", Gaodeng Xuexiao Huaxue Xuebao, vol. 9, No. 8, 1988, pp. 853.855.
Database, Chemical Abstracts Service, XP002271335, abstract &Szajda et al, Carbon 13 NMR study of o-, m- and p-' (alkoxycarbonyl)alkoxy chalcones and their alpha, beta dibromo derivatives, Magnetic Resonance in Chemistry, vol. 27, No. 4, 1989, pp. 399-402.
Cheng et al, "Broussochalcone A, a potent antioxidant and effective suppressor of inducible nitric oxide synthase in lipopolysaccharide-activated macrophages", Biochemical Pharmacology 61 (2001) 939-946.
Cheng et al, "Antioxidant properties of butein isolated from Dalbergia odorifera", Biochemica et Biophyics Acta 1392 (1908) 291-299.
Hsieh et al, "Synthesis and Anti-inflammatory Effect of Chalcones and Related Compounds", Pharmaceutical Research, vol. 15, No. 1, 1998, pp. 39-46.
French et al, "A New Preparation of Substituted 4H-1-Benzothiopyran-4-ones from C(a),N-Benzyolhydrazones or C(a),N-Carboalkoxyhydrazones and Methyl Thiosalicylate," Journal of Heterocyclic Chemistry, 1998, 35, 45-48.
Pond, F. J., et al., "The Action of Sodium Alcoholate Upon Anisylidene Acetophenone Dibromide", Journal of the American Chemical Society (1900), 22(10), 658-85.
Malik et al, "Synthesis and bioefficacy evaluation of 2-[4-(3-arylprop-2-enoyl)phenoxy]-N-substituted acetamides and 2-[4-(5-aryl-4,5-dihydro-1$H$-pyrazol-3-yl)-phenoxylacetic acid hydrazides as potential pesticides", Indian Journal of Chemistry, vol. 40B, Aug. 2001, pp. 682-687.

* cited by examiner

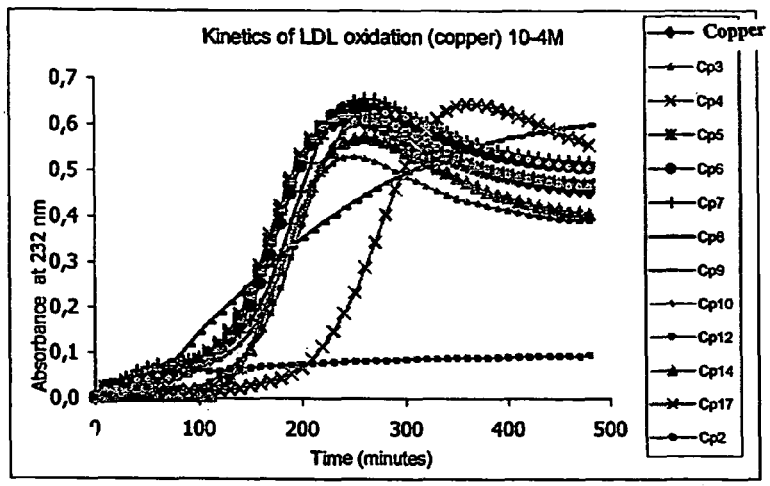
Figure : 1-1
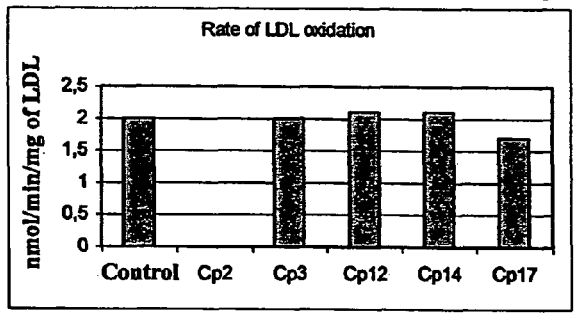
Figure : 1-2
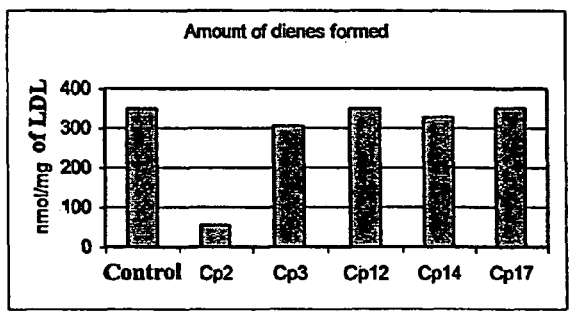
Figure : 1-3
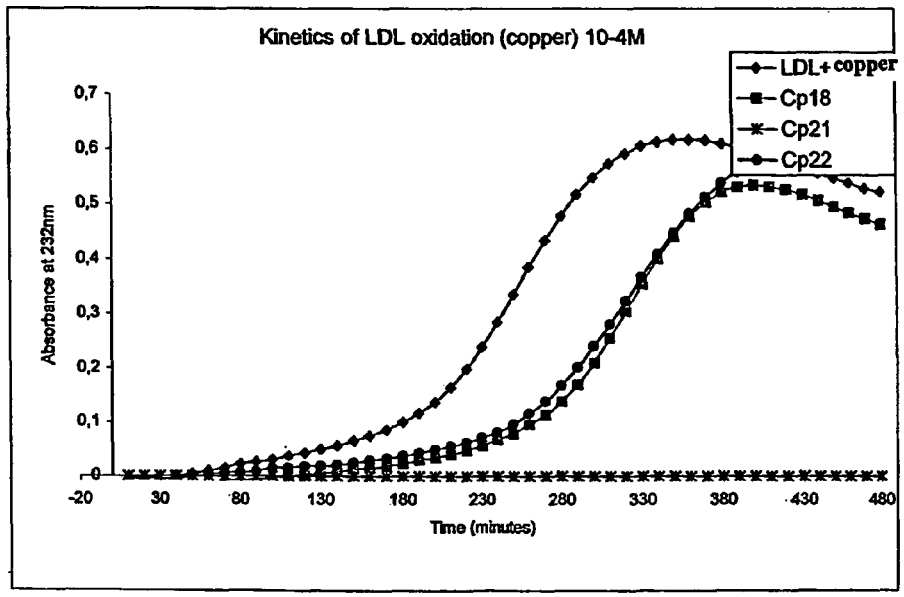
Figure :1-4

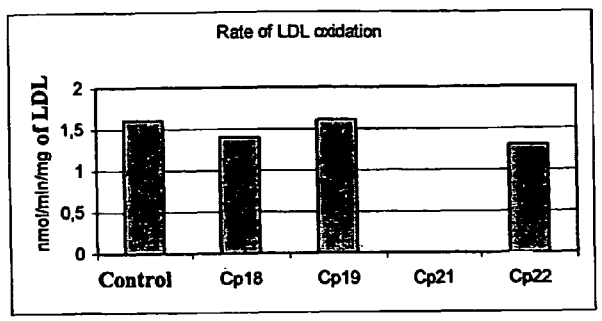
Figure : 1-5
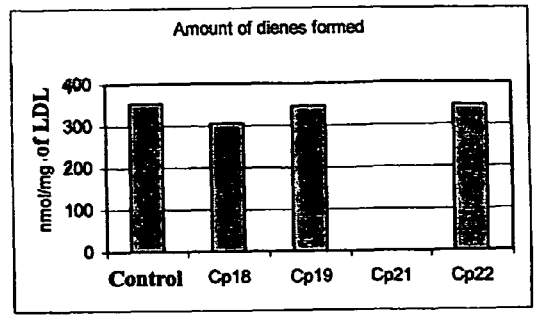
Figure : 1-6
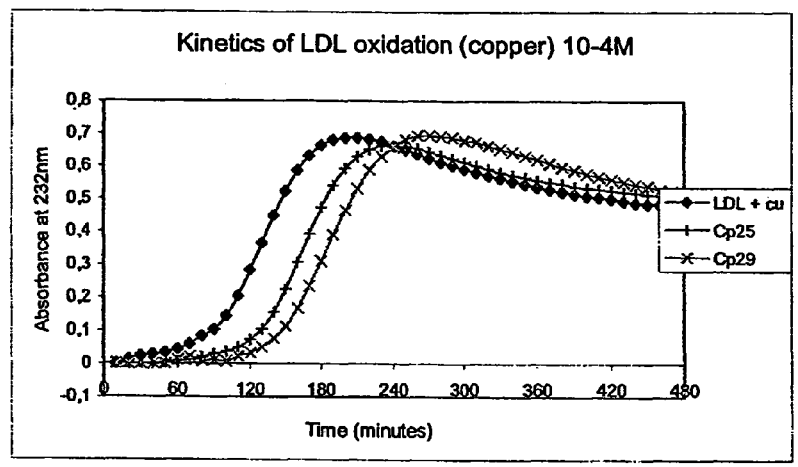
Figure : 1-7
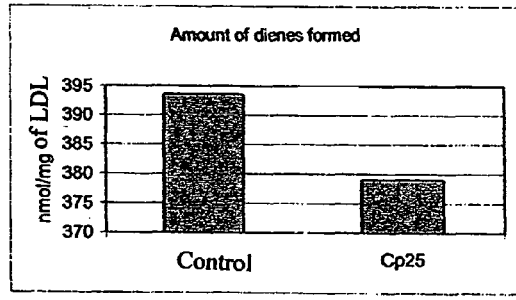
Figure : 1-8

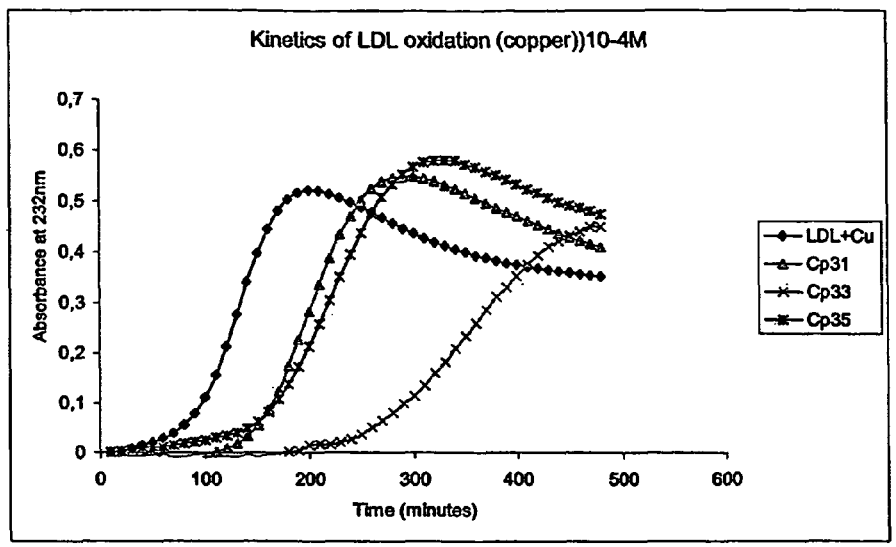
Figure : 1-9
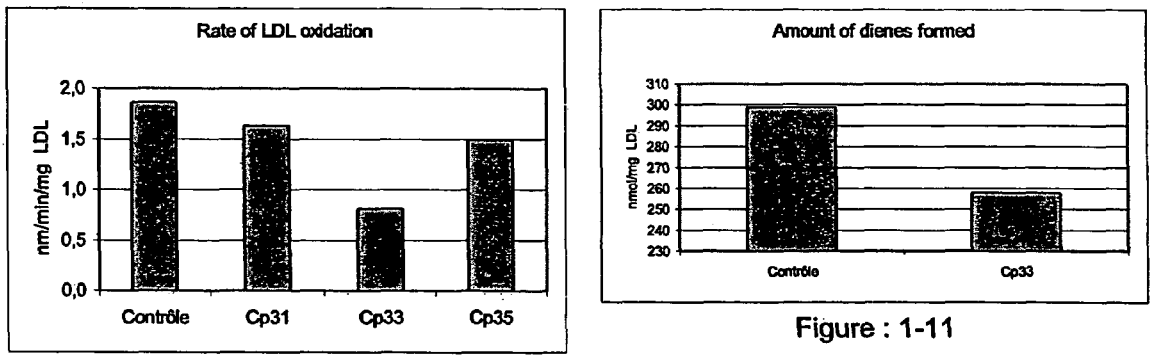
Figure : 1-10
Figure : 1-11
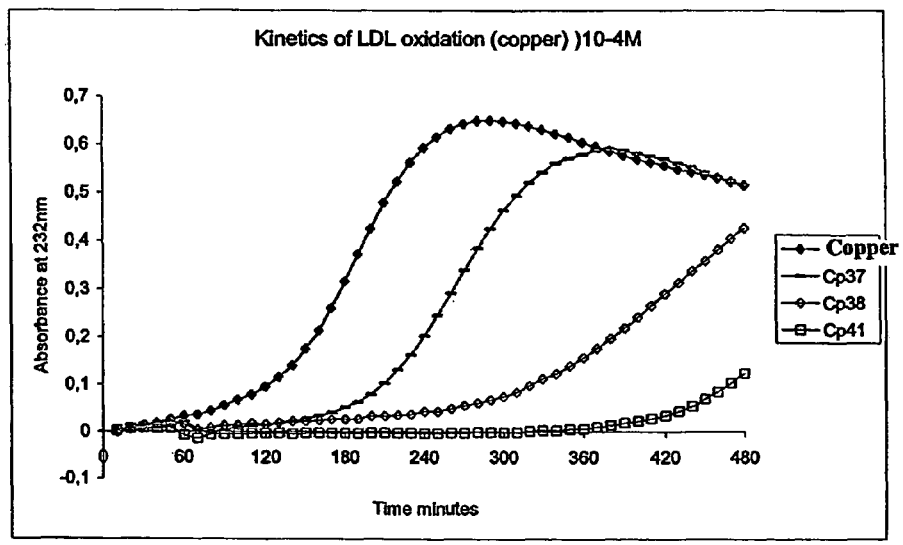
Figure : 1-12

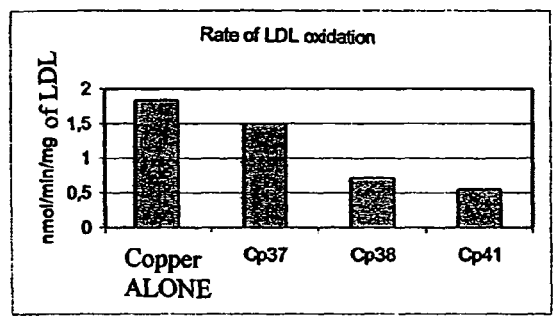
Figure: 1-13
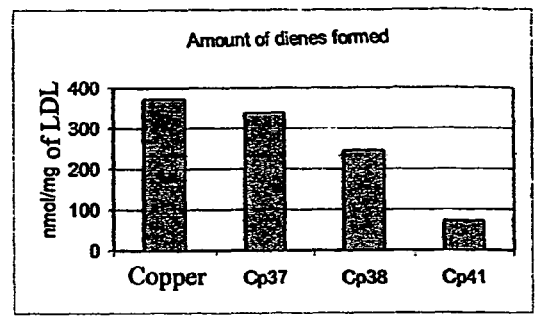
Figure: 1-14

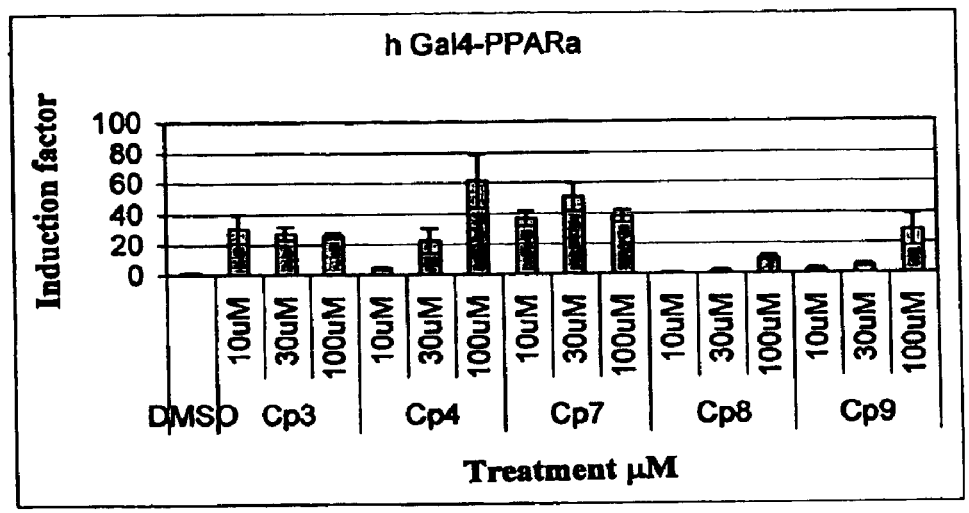
Figure: 2-1
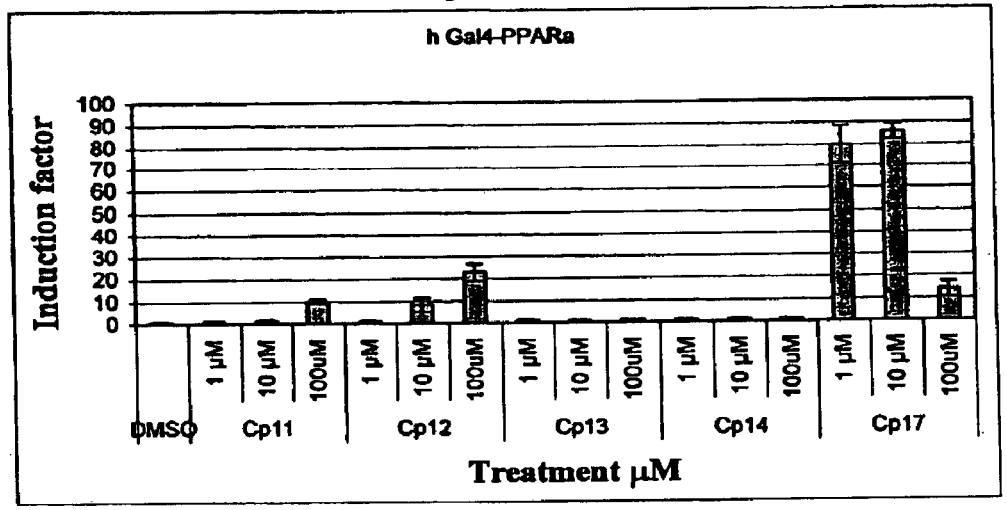
Figure: 2-2
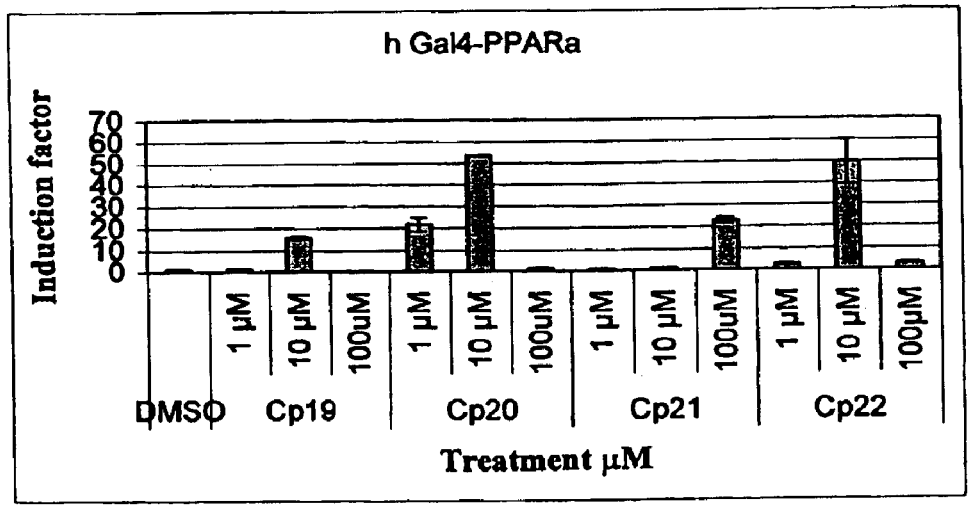
Figure: 2-3

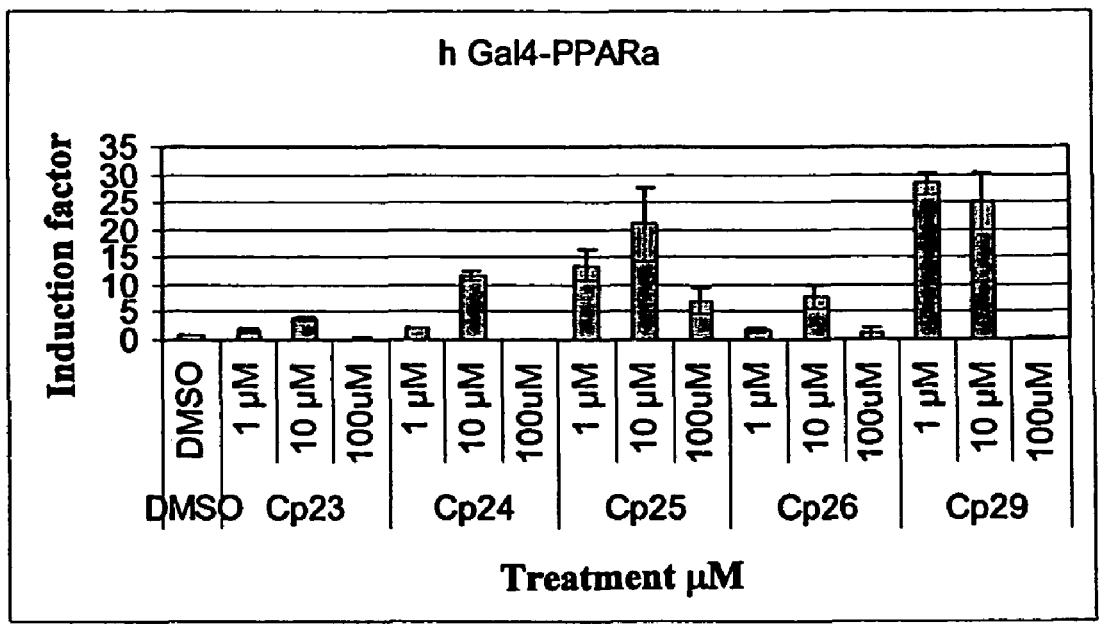
Figure : 2-4
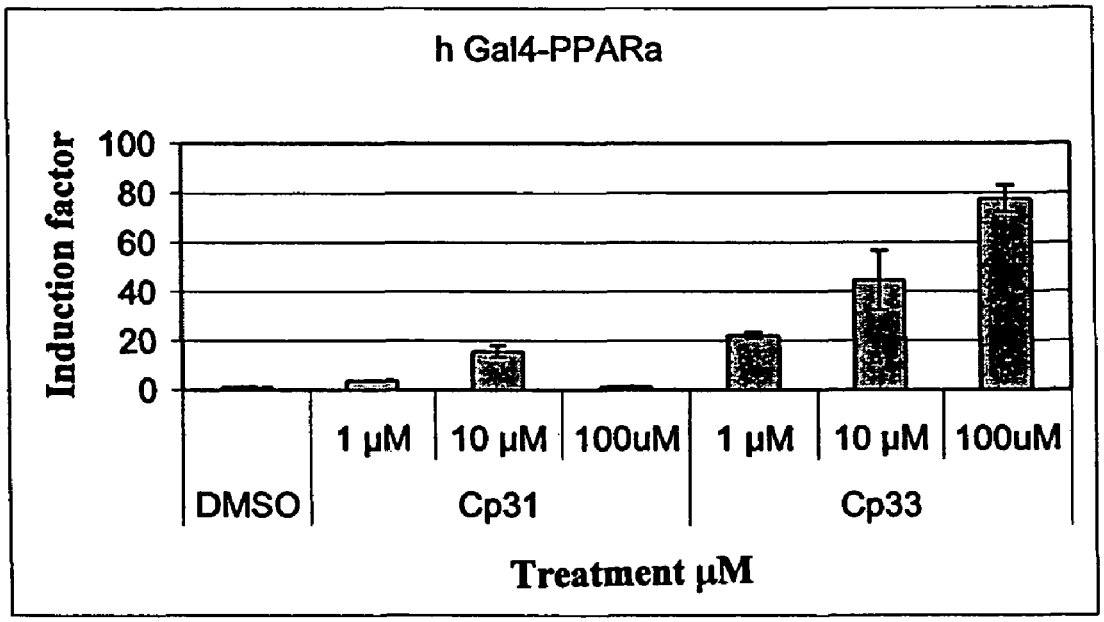
Figure : 2-5

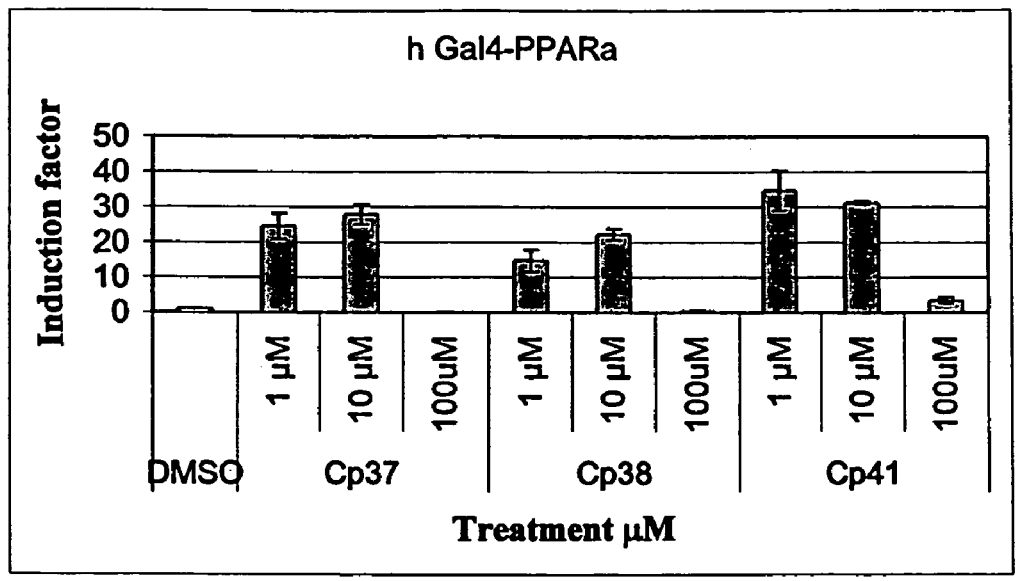
Figure : 2-6
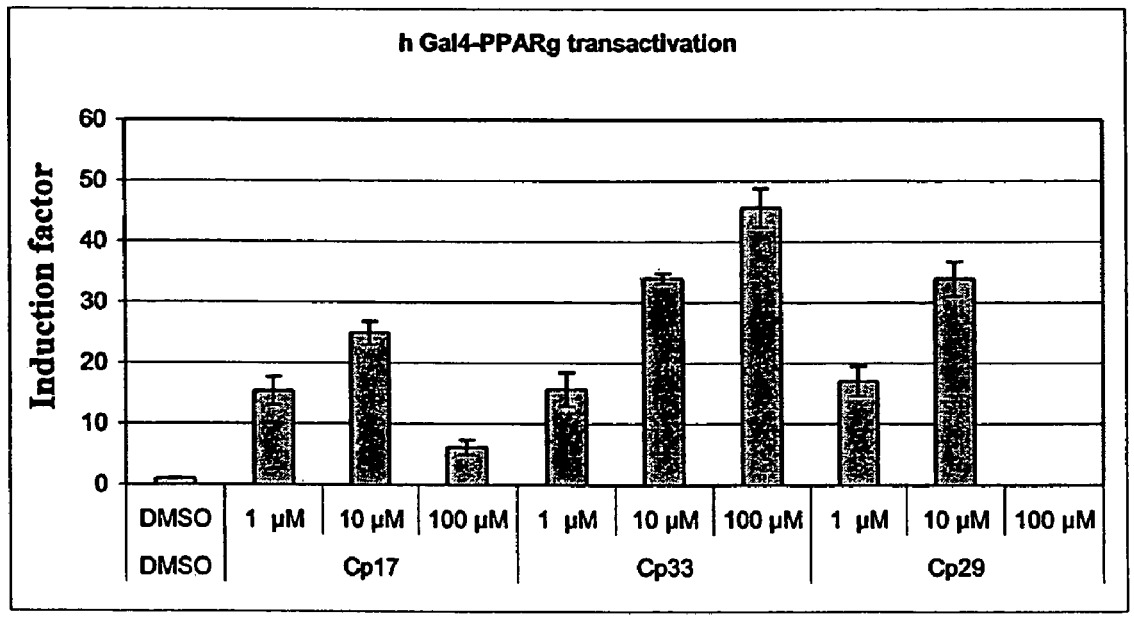
Figure : 2-7

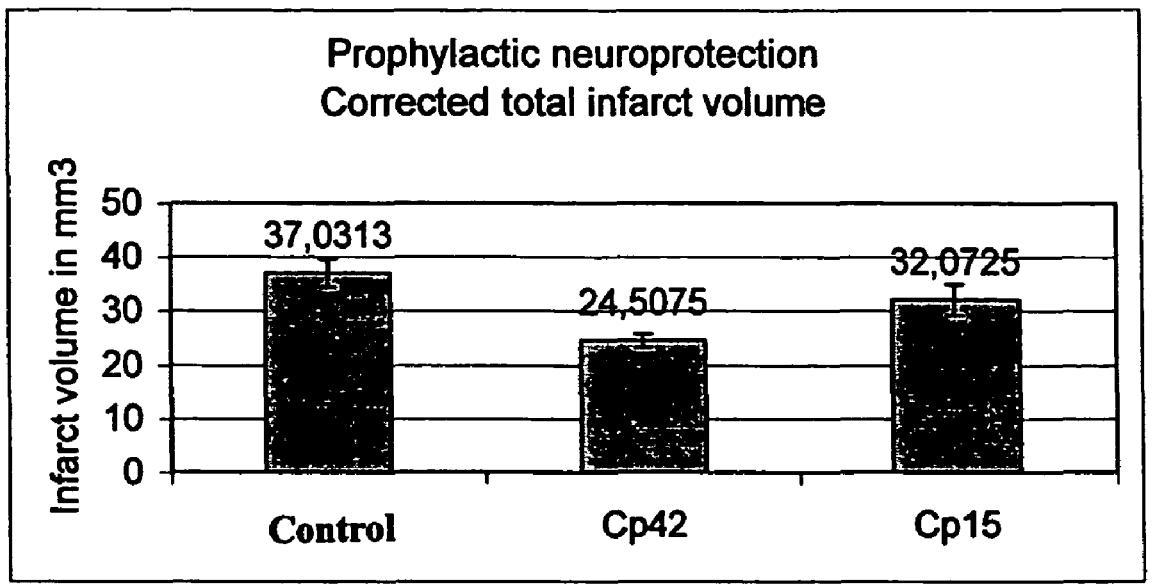
Figure : 3-1
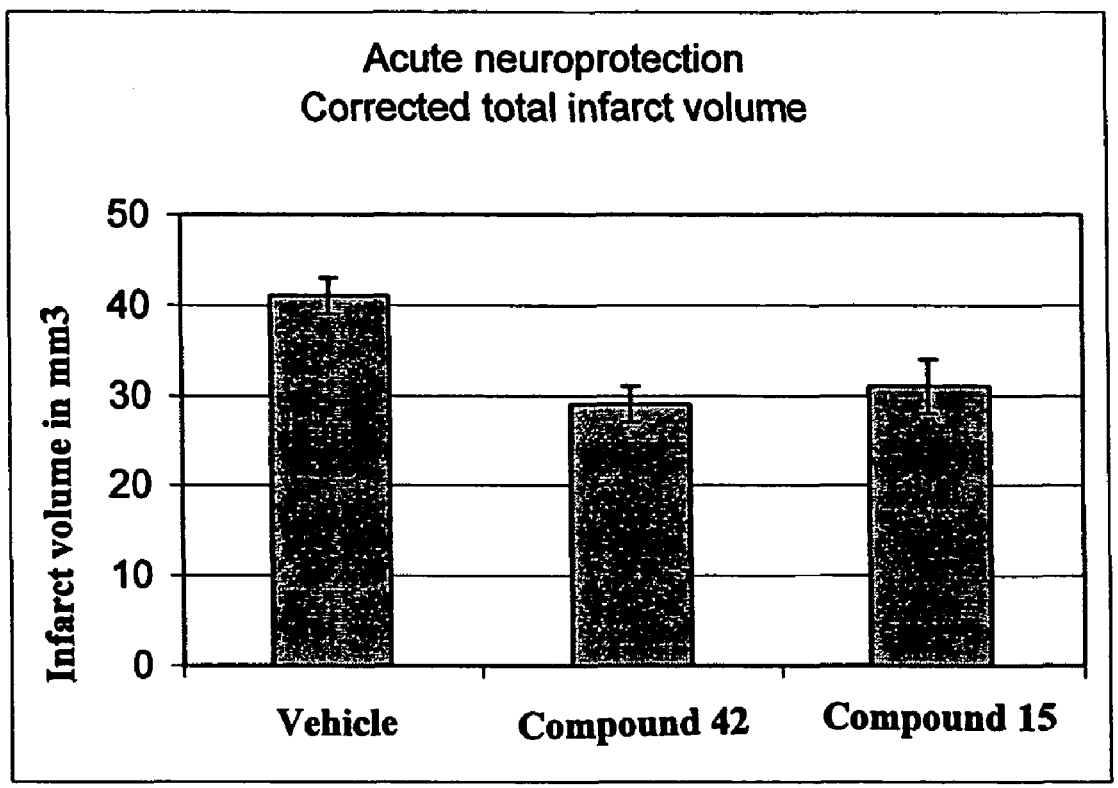
Figure : 3-2

SUBSTITUTED 1,3-DIPHENYLPROP-2-EN-1-ONE DERIVATIVES AND PREPARATION AND USES THEREOF

This application is the US national phase of international application PCT/FR2003/002127 filed 8 Jul. 2003 which designated the U.S. and claims benefit of FR 02/08571, dated 8 Jul. 2002, the entire content of which is hereby incorporated by reference.

The invention concerns novel substituted 1,3-diphenyl-prop-2-en-1-one derivatives, pharmaceutical compositions comprising same, their therapeutic uses, in particular for treating cerebral ischemia. The invention also concerns a method for preparing said derivatives.

In France, cerebrovascular disease (150,000 new cases annually) is the third leading cause of mortality and the leading cause of disability in adults. Ischemic and hemorrhagic stroke respectively account for 80% and 20% of all cerebrovascular accidents. Ischemic stroke is an important therapeutic issue that must be addressed in order to reduce the morbidity and mortality of cerebrovascular disease. Progress has been made not only in treating the acute phase of ischemia but also in preventing same. It is therefore important to keep in mind that the identification and management of risk factors are essential in the treatment of this pathology.

Drug-based treatments of cerebral ischemia are based on different strategies. A first strategy comprises preventing the occurrence of cerebral ischemic accidents through prevention of risk factors (hypertension, hypercholesterolemia, diabetes, atrial fibrillation, etc.) or through prevention of thrombosis, in particular with the help of antiplatelet drugs or anticoagulants (Gorelick 2002) (Adams 2002).

A second strategy comprises treating the acute phase of ischemia, so as to attenuate its long-term consequences (Lutsep and Clark 2001).

The pathophysiology of cerebral ischemia can be described as follows: the ischemic penumbra, an intermediate zone between the ischemic focus where the neurons are necrotized and the intact nerve tissue, is the site of a pathophysiological cascade which leads over the course of a few days to neuronal death, if reperfusion does not occur or if neuroprotection is insufficient. The first event, which takes place in the first few hours, is a massive release of glutamate which leads to neuron depolarization and cerebral oedema. Calcium influx into the cell induces mitochondrial damage leading to the release of free radicals and the induction of enzymes that promote degradation of neuronal membranes. Calcium influx and free radical production in turn activate certain transcription factors, such as NF-κB. Said activation induces inflammatory processes such as induction of endothelial adhesion proteins, polynuclear neutrophil infiltration of the ischemic focus, microglial activation, induction of enzymes like nitric oxide (NO) synthase type II or cyclooxygenase type II. These inflammatory processes lead to release of NO or prostanoids which are toxic to the cell. Together, these processes result in a phenomenon of apoptosis inducing irreversible lesions (Dimagl, Iadecola et al. 1999).

The concept of prophylactic neuroprotection is based on experimental data in animal models demonstrating ischemic tolerance. In fact, different procedures applied prior to experimentally induced brain ischemia attenuate the severity of the latter. Various stimuli can induce brain ischemic tolerance: preconditioning (brief ischemia preceding prolonged ischemia); heat stress; administration of a low dose of bacterial lipopolysaccharide (Bordet, Deplanque et al. 2000).

Said stimuli induce tolerance mechanisms which activate signals triggering protective mechanisms. Different triggering mechanisms have been identified: cytokines, inflammatory pathways, free radicals, NO, ATP-dependent potassium channels, adenosine. The observed lag time between the onset of early events and ischemic tolerance stems from the need for protein synthesis. Various types of proteins have been shown to induce ischemic tolerance: heat shock proteins, antioxidant enzymes and anti-apoptotic proteins (Nandagopal, Dawson et al. 2001).

Thus there is a real need for compounds capable of preventing the development of risk factors for cerebrovascular accidents such as atherosclerosis, diabetes, obesity, and the like, capable of providing prophylactic neuroprotection but also active neuroprotection in the acute phase of cerebral ischemia.

Fibrates are widely used in the treatment of hypertriglyceridemias. They also have beneficial effects in hypercholesterolemia. Fibrates have a pleiotropic mechanism of action. They activate a class of nuclear receptors (PPARs) involved in coordinating the expression of proteins responsible for lipid transport or metabolism. The pleiotropic nature of the fibrate mechanism of action stems from the diversity of PPAR target genes. In fact, fibrates are capable of normalizing serum lipid levels and therefore of reducing the development of atherosclerosis, but they also display anti-inflammatory properties on the vessel wall and on thrombosis (Fruchart, Staels et al. 2001).

The PPARs ($\alpha,\beta,\gamma$) belong to the hormone-activated nuclear receptor family. When activated by binding with their ligand, they heterodimerize with Retinoid-X-Receptor (RXR) and bind to "Peroxisome Proliferator Response Elements" (PPREs) located in the promoter sequence of target genes. Binding of PPAR to PPRE thereby induces expression of the target gene (Fruchart, Staels et al. 2001). The PPARs are distributed in a wide variety of organs, although they all exhibit a certain degree of tissue specificity with the exception of PPARβ the expression of which appears to be ubiquitous. PPARα expression is particularly high in liver and in the intestinal lumen whereas PPARγ is expressed mainly in fat tissue and spleen. The three subtypes ($\alpha, \beta, \gamma$) are expressed in the central nervous system. Cells such as oligodendrocytes and astrocytes more particularly express the PPARα subtype (Kainu, Wikstrom et al. 1994).

The target genes of PPARs control lipid and glucose metabolism. However, recent discoveries suggest that the PPARs participate in other biological processes. PPAR activation by their ligands induces changes in the transcriptional activity of genes which modulate the inflammatory process, antioxidant enzymes, angiogenesis, cell proliferation and differentiation, apoptosis, the activities of iNOS, MMPases and TIMPs (Smith, Dipreta et al. 2001; Clark 2002). For example, activation of PPAR α and γ is responsible for cessation of epidermal keratinocyte proliferation and promotes the differentiation thereof (Ellis, Varani et al. 2000; Komuves, Hanley et al. 2000).

Free radicals play a role in a very wide range of pathologies including allergy, tumor initiation and promotion, cardiovascular diseases (atherosclerosis, ischemia), genetic and metabolic disorders (diabetes), infectious and degenerative diseases (Alzheimer's disease, Parkinson's disease, Prion, etc.) and in ophthalmic disorders (Mates, Perez-Gomez et al. 1999).

Reactive oxygen species (ROS) are produced during normal cell functioning. ROS comprise the hydroxyl radical (OH), superoxide anion ($O_2^-$), hydrogen peroxide ($H_2O_2$) and nitric oxide (NO). Said species are very labile and, due to their high chemical reactivity, constitute a danger to the biological functions of cells. They induce lipid peroxidation, oxidation of certain enzymes and very extensive oxidation of proteins leading to degradation thereof. Protection against lipid peroxidation is a vital process in aerobic organisms, because peroxidation products can cause DNA damage. Thus a deregulation or modification of the equilibrium between the production, processing and elimination of radical species by natural antioxidant defenses leads to the establishment of processes that are deleterious to the cell or organism.

ROS are processed via an antioxidant system that comprises an enzymatic component and a non-enzymatic component. The enzymatic system is composed of several enzymes which have the following characteristics:

Superoxide dismutase (SOD) destroys the superoxide radical by converting it to peroxide. The peroxide in turn is acted upon by another enzyme system. Low levels of SOD are continuously produced by aerobic respiration. Three classes of SOD have been identified in humans, each containing Cu, Zn, Fe, Mn, or Ni as cofactor. The three forms of human SOD are distributed as follows: a cytosolic Cu—Zn SOD, a mitochondrial Mn—SO and an extracellular SOD.

Catalase is very efficient at converting hydrogen peroxide ($H_2O_2$) to water and $O_2$. Hydrogen peroxide is enzymatically catabolized in aerobic organisms. Catalase also catalyzes the reduction of a variety of hydroperoxides (ROOH).

Glutathione peroxidase uses selenium as cofactor and catalyzes the reduction of hydroperoxides (ROOH and $H_2O_2$) by using glutathione, and thereby protects cells against oxidative damage.

Non-enzymatic antioxidant defenses comprise molecules which are synthesized or supplied in the diet.

Antioxidant molecules are present in different cell compartments. Detoxification enzymes for example eliminate free radicals and are essential to cell life. The three most important types of antioxidant compounds are the carotenoids, vitamin C and vitamin E (Gilgun-Sherki, Melamed et al. 2001).

To avoid the phenomenon of apoptosis induced by cerebral ischemia and its resultant effects, the inventors have developed novel compounds capable of preventing the development of the risk factors described earlier and capable of exerting a prophylactic neuroprotective activity, but also of providing active neuroprotection during the acute phase of cerebral ischemia.

The inventors have also shown that the compounds according to the invention concurrently display PPAR activator, antioxidant and anti-inflammatory properties and, as such, said compounds have an important therapeutic or prophylactic potential in cerebral ischemia.

The invention thus concerns novel substituted 1,3-diphenylprop-2-en-1-one derivatives, pharmaceutical compositions containing same, their therapeutic uses, in particular for treating cerebral ischemia.

The present invention is therefore directed at providing novel substituted 1,3-diphenylprop-2-en-1-one derivatives having an improved formula and a satisfactory therapeutic efficacy.

These and other objectives are attained by the invention which in particular has as its object substituted 1,3-diphenyl-prop-2-en-1-one derivatives represented by formula (I) below:

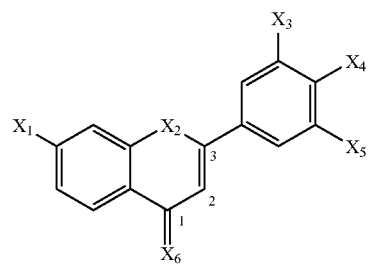

in which:
$X_1$ represents a halogen or a —R1 group or a group corresponding to the following formula: -G1-R1,
$X_2$ represents a halogen atom or a thionitroso group or a hydroxy group or an unsubstituted alkyloxy group or an alkylcarbonyloxy group or a thiol group or an alkylthio group or an alkylcarbonylthio group, $X_2$ can also represent an oxygen or sulfur atom bound to carbon 3 of the propene chain, so as to form a derivative of the type 2-phenyl-4H-1-benzopyran-4-one (this option is depicted in formula (I) by the dotted line),
$X_3$ represents a —R3 group or a group corresponding to the following formula: -G3-R3,
$X_4$ represents a halogen or a thionitroso group or a —R4 group or a group corresponding to the following formula: -G4-R4,
$X_5$ represents a —R5 group or a group corresponding to the following formula: -G5—R5,
$X_6$ is an oxygen atom or a nitrogen atom, in the case where $X_6$ is a nitrogen atom, it carries a hydrogen atom or a hydroxy group or an alkyloxy group,
R1, R3, R4, R5, which are the same or different, represent a hydrogen atom or an alkyl group substituted or not by at least one substituent which is part of group 1 or group 2 defined hereinbelow,
G1, G3, G4, G5, which are the same or different, represent an oxygen or sulfur atom,
with at least one of the groups X1, X3, X4 or X5 corresponding to the formula -G-R, and
with at least one of the groups R1, R3, R4 or R5 present in the form of an alkyl group having at least one substituent from group 1 or 2, said alkyl group being directly bound to the ring or being associated with a group G according to the formula -GR,
the substituents from group 1 are selected in the group consisting of carboxy groups having the formula: —$COOR_6$ and carbamoyl groups having the formula: —$CONR_6R_7$,
the substituents from group 2 are selected in the group consisting of sulfonic acid (—$SO_3H$) and sulfonamide groups having the formula: —$SO_2NR_6R_7$,
with $R_6$ and $R_7$, which are the same or different, representing a hydrogen atom or an alkyl group possibly substituted by at least one group of type 1 or 2,
the optical and geometrical isomers, racemates, tautomers, salts, hydrates and mixtures thereof,
with the exception of compounds represented by formula (I) in which:
—$X_1$, $X_2$, $X_3$ and $X_5$ each represent a hydrogen atom, $X_6$ represents an oxygen atom and $X_4$ represents a group corresponding to the formula —O—$CR_8R_9$—$COOR_{10}$, where $R_8$ and $R_9$, which are the same or different, represent a C1 to C2 alkyl group (comprising one or two carbon atoms), and $R_{10}$ represents a hydrogen atom or a C1 to C7 alkyl group (comprising one to seven carbon atoms), —$X_2$, $X_3$ and $X_5$ each represent a hydrogen atom, $X_1$ represents a halogen atom or a R1 or -G1R1 group, where R1 represents an unsubstituted C1 to C2 alkyl group and G1 represents an oxygen atom, $X_6$ represents an oxygen atom and $X_4$ represents a group corresponding to the formula —O—$CR_{11}R_{12}$—$COOR_{10}$, where $R_{11}$ and $R_{12}$, which are the same or different, represent a hydrogen atom or a C1 to C2 alkyl group, and $R_{10}$ represents a hydrogen atom or a C1 to C7 alkyl group, and —$X_2$— represents a hydrogen atom and $X_1$ represents -G1R1 where G1 represents an oxygen atom and R1 represents CH2COOH.

The invention also encompasses the prodrugs of the compounds represented by formula (I) which, after administration to a subject, are converted to compounds represented by formula (I) and/or metabolites of compounds represented by formula (I) which display similar therapeutic activity to compounds represented by formula (I).

The invention also has as its object a pharmaceutical composition comprising, in a pharmaceutically acceptable support, at least one compound represented by formula (I) such as defined hereinabove, possibly in association with another active therapeutic agent.

The invention also concerns the use of at least one compound represented by formula (I) for preparing a pharmaceutical composition for treating a cerebrovascular pathology, such as cerebral ischemia or cerebral hemorrhagic stroke.

The invention finally has as its object a method for preparing compounds represented by formula (I).

In the scope of the invention, the derivatives represented by formula (I) such as defined hereinabove can adopt a cis or trans conformation.

Advantageously, none of the groups X3, X4 and X5 represents a hydrogen atom. Compounds with formula (I) which meet this definition constitute compounds of general family (II).

Advantageously, one or two of the groups X3, X4 and X5 represent a hydrogen atom and X1 is an unsubstituted alkyl group. Compounds with formula (I) which meet this definition constitute compounds of general family (III).

Advantageously, one or two of the groups X3, X4 and X5 represent a hydrogen atom and X2 is a thionitroso group or an alkylcarbonyloxy group or a thiol group or an alkylthio group or an alkylcarbonylthio group, X2 can also represent an oxygen or sulfur atom bound to carbon 3 of the propene chain, so as to form a derivative of the type 2-phenyl-4H-1-benzopyran-4-one (this option is depicted in formula (I) by dotted lines). Compounds with formula (I) which meet this definition constitute compounds of general family (IV).

Advantageously, one or two of the groups X3, X4 and X5 represent a hydrogen atom and at least one of the groups X1, X3, X4 or X5 is the GR form in which G is a sulfur atom. Compounds with formula (I) which meet this definition constitute compounds of general family (V).

Advantageously, one or two of the groups X3, X4 and X5 represent a hydrogen atom and at least one of the groups X1, X3, X4 or X5 is the -G-R form in which G is an oxygen atom and R is an alkyl group substituted by a substitutent from group I in which R6 is not a hydrogen atom. Compounds with formula (I) which meet this definition constitute compounds of general family (VI).

Advantageously, one or two of the groups X3, X4 and X5 represent a hydrogen atom and at least one of the groups X1, X3, X4 or X5 is the GR form in which G is an oxygen atom and R is an alkyl group substituted by a sulfonamide such as defined hereinabove. Compounds with formula (I) which meet this definition constitute compounds of general family (VII).

Advantageously, X4 is a thionitroso group or a —R4 group or a group corresponding to the formula -G4-R4. Derivatives with formula (I) in which X4 meets this definition constitute derivatives represented by general formula (VIII) in which G4 and R4 are such as defined hereinabove.

Advantageously, X2 is a thionitroso group or a hydroxy group or an alkyloxy group or a thiol group or an alkylthio group. Derivatives with formula (I) in which X2 meets this definition constitute derivatives represented by general formula (IX).

Other advantageous derivatives represented by formula (I) of the invention have a general formula (X) such that X4 is a thionitroso group or a —R4 group or a group corresponding to the formula -G4-R4 and X2 is a thionitroso group or a hydroxy group or an alkyloxy group or a thiol group or an alkylthio group, G4 and R4 being such as defined hereinabove.

Other advantageous derivatives represented by formula (I) of the invention have a general formula (XI) such that X1 represents a —R1 group or a group corresponding to the formula -G1-R1, with R1 being an alkyl group substituted by a substituent which is part of group 1 and G1 and the substituent from group 1 being such as defined hereinabove.

More preferably, another object of the invention concerns derivatives represented by formula (XI) such as described hereinabove, characterized in that X1 is a -G1-R1 group.

Even more preferably, another object of the invention concerns derivatives represented by formula (XI) such as described hereinabove, characterized in that X1 is a -G1-R1 group in which G1 is an oxygen atom.

Other advantageous derivatives represented by formula (I) of the invention have a general formula (XII) such that X1 represents a —R1 group or a group corresponding to the formula -G1-R1, with R1 being an alkyl group substituted by a substituent which is part of group 2 and G1 and the substituent from group 2 being such as defined hereinabove.

Other advantageous derivatives represented by formula (I) of the invention have a general formula (XIII) such that X3 represents a —R3 group or a group corresponding to the formula -G3-R3, with R3 being an alkyl group substituted by a substituent which is part of group 1 and G3 and the substituent from group 1 being such as defined hereinabove.

Other advantageous derivatives represented by formula (I) of the invention have a general formula (XIV) such that X3 represents a —R3 group or a group corresponding to the formula -G3-R3, with R3 being an alkyl group substituted by a substituent which is part of group 2 and G3 and the substituent from group 2 being such as defined hereinabove.

Other advantageous derivatives represented by formula (I) of the invention have a general formula (XV) such that X4 represents a —R4 group or a group corresponding to the formula -G4-R4, with R4 being an alkyl group substituted by a substituent which is part of group 1 and G4 and the substituent from group 1 being such as defined hereinabove.

More preferably, another object of the invention concerns derivatives represented by formula (XV) such as described hereinabove, characterized in that X4 is a -G4-R4 group.

Even more preferably, another object of the invention concerns derivatives represented by formula (XV) such as described hereinabove, characterized in that X4 is a -G4-R4 group in which G4 is an oxygen atom.

Even more preferably, another object of the invention concerns derivatives represented by formula (XV) such as described hereinabove, characterized in that X4 is a -G4-R4 group in which G4 is an oxygen atom, and X3 or X5 respectively represent R3 or G3R3, on the one hand, and R5 or G5R5, on the other hand, with R3 or R5 being alkyl groups carrying a substitutent from group 1, said substituent from group 1 being such as defined hereinabove.

Other advantageous derivatives represented by formula (I) of the invention have a general formula (XVI) such that X4 represents a —R4 group or a group corresponding to the formula -G4-R4 with R4 being an alkyl group substituted by a substituent which is part of group 2 and G4 the substituent from group 2 being such as defined hereinabove.

Other advantageous derivatives represented by formula (I) of the invention have a general formula (XVII) such that X1 represents a halogen.

Other advantageous derivatives represented by formula (I) of the invention have a general formula (XVIII) such that X1 represents a —R1 group with R1 being a C1 to C4 alkyl group substituted or not by at least one substituent which is part of group 1 or group 2 defined hereinabove.

Other advantageous derivatives represented by formula (I) of the invention have a general formula (XIX) such that X1 represents a -G1R1 group with R1 being a C1 to C3 alkyl group substituted or not by at least one substituent which is part of group 1 or group 2 defined hereinabove.

Other advantageous derivatives represented by formula (I) of the invention have a general formula (XX) such that X1 represents a —R1 group with R1 being a C5 to C24 alkyl group substituted or not by at least one substituent which is part of group 1 or group 2 defined hereinabove.

Other advantageous derivatives represented by formula (I) of the invention have a general formula (XXI) such that X1 represents a -G1R1 group with R1 being a C4 to C24 alkyl group substituted or not by at least one substituent which is part of group 1 or group 2 defined hereinabove.

Other advantageous derivatives represented by formula (I) of the invention have a general formula (XXII) such that X6 represents an oxygen atom.

Another object of the invention concerns derivatives represented by formula (I) such as defined hereinabove, characterized in that X4 is a -G4-R4 group, R4 is such as defined hereinabove and X3 or X5 respectively represent R3 or G3R3, on the one hand, and R5 or G5R5, on the other hand, with R3 or R5 being an alkyl group carrying a substitutent from group 1, said substituent from group 1 being such as defined hereinabove.

Another object of the invention concerns derivatives represented by formula (I) in which X1, X3, X4 or X5 represent OC(CH3)2COOR6 with R6 being such as defined hereinabove.

Another object of the invention concerns derivatives represented by formula (I) in which X1, X3, X4 or X5 represent SC(CH3)2COOR6 with R6 being such as defined hereinabove.

According to the invention, the term "alkyl" designates a saturated hydrocarbon function, linear, branched or cyclic, halogenated or not, having more particularly from 1 to 24, preferably 1 to 10, carbon atoms such as methyl, ethyl, propyl, isopropyl, butyl, isobutyl, tert-butyl, pentyl, neopentyl, n-hexyl. Groups containing one or two carbon atoms or containing from two to seven carbon atoms are particularly preferred. Methyl and ethyl groups are quite particularly preferred.

The term thionitroso refers to a nitroso group bound to the aromatic ring through a sulfur atom.

The term halogen represents a chlorine atom or a bromine atom or an iodine atom or a fluorine atom.

The term alkyloxy designates an alkyl chain bound to the ring by an oxygen atom. The alkyl chain is defined earlier.

The term alkylthio refers to an alkyl chain bound to the aromatic ring by a sulfur atom (thioether bond). The alkyl chain is defined earlier.

According to a particular embodiment of the invention, preferred compounds are indicated below with their corresponding formulas:

1-[2-hydroxy-4-chlorophenyl]-3-[4-carboxydimethylmethyloxyphenyl]prop-2-en-1-one and 1-[2-hydroxy-4-chlorophenyl]-3-[4-isopropyloxycarbonyl dimethylmethyloxyphenyl]prop-2-en-1-one:

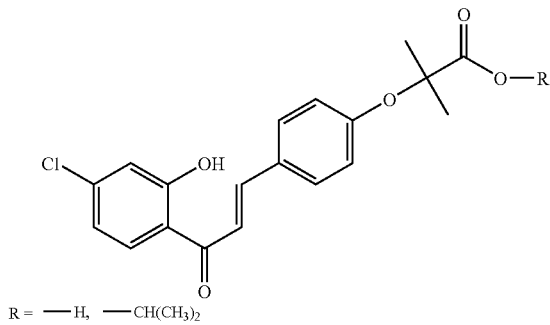

R = —H, —CH(CH$_3$)$_2$

1-[2-hydroxyphenyl]-3-[4-carboxydimethylmethyloxyphenyl]prop-2-en-1-one and 1-[2-hydroxyphenyl]-3-[4-isopropyloxycarbonyldimethylmethyloxyphenyl]prop-2-en-1-one

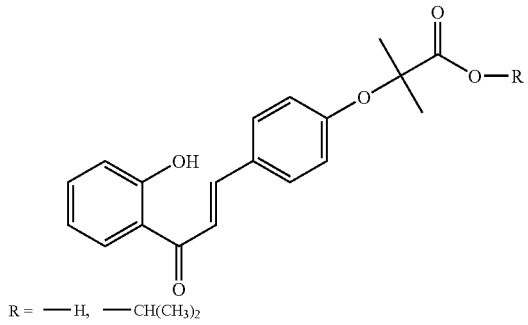

R = —H, —CH(CH$_3$)$_2$

1-[2-methylcarbonyloxyphenyl]-3-[4-carboxydimethylmethyloxyphenyl]prop-2-en-1-one and 1-[2-methylcarbonyloxyphenyl]-3-[4-isopropyloxycarbonyldimethyl methyloxyphenyl]prop-2-en-1-one:

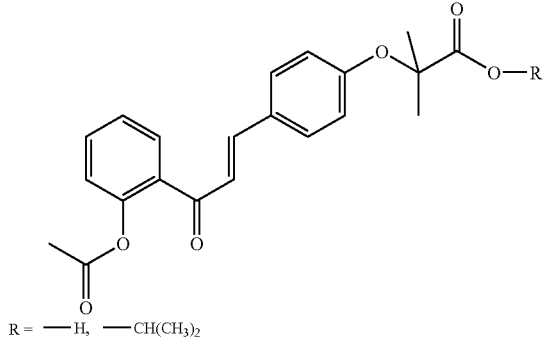

R = —H, —CH(CH$_3$)$_2$

1-[2-hydroxyphenyl]-3-[4-carboxydimethylmethyloxyphenyl]-1-hydroxyiminoprop-2-ene and 1-[2-hydroxyphenyl]-3-[4-isopropyloxycarbonyldimethylmethyloxyphenyl]-1-hydroxyiminoprop-2-ene:

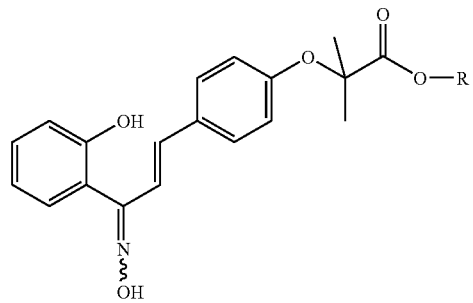

R = —H, —CH(CH₃)₂

1-[2-hydroxy-4-carboxydimethylmethyloxyphenyl]-3-[3,5-ditertbutyl-4-hydroxyphenyl]prop-2-en-1-one, 1-[2-hydroxy-ethyloxycarbonyl dimethylmethyloxyphenyl]-3-[3,5-ditertbutyl-4-hydroxyphenyl]prop-2-en-1-one and 1-[2-hydroxy-4-ethoxycarbonyldimethylmethyloxyphenyl]-3-[3,5-ditertbutyl-4-hydroxyphenyl]prop-2-en-1-one:

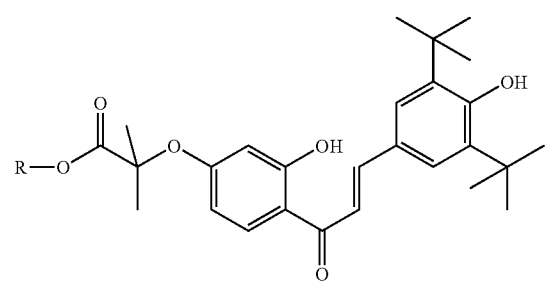

R = —H, —CH(CH₃)₂, —C₂H₅

1-[2-hydroxyphenyl]-3-[3-carboxydimethylmethyloxy-4-hydroxy-5-tertbutylphenyl]prop-2-en-1-one and 1-[2-hydroxyphenyl]-3-[3-isopropyloxycarbonyldimethylmethyloxy-4-hydroxy-5-tertbutylphenyl]prop-2-en-1-one:

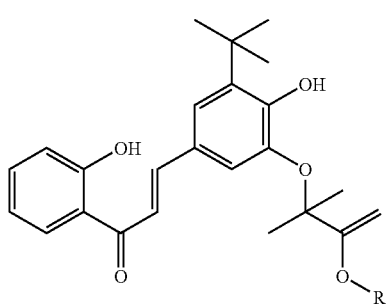

R = —H, —CH(CH₃)₂

1-[2-hydroxy-4-chlorophenyl]-3-[3-carboxydimethylmethyloxy-4-hydroxy-5-tertbutylphenyl]prop-2-en-1-one and 1-[2-hydroxy-4-chlorophenyl]-3-[3-isopropyloxycarbonyldimethylmethyloxy-4-hydroxy-5-tertbutylphenyl]prop-2-en-1-one:

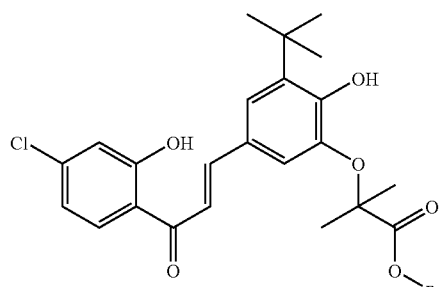

R = —H, —CH(CH₃)₂

1-[2-hydroxyphenyl]-3-[3-carboxydimethylmethyl-4-hydroxy-5-tertbutylphenyl]prop-2-en-1-one and 1-[2-hydroxyphenyl]-3-[3-isopropyloxycarbonyldimethylmethyl-4-hydroxy-5-tertbutylphenyl]prop-2-en-1-one:

R = —H, —CH(CH₃)₂

1-[2-hydroxy-4-chlorophenyl]-3-[3-carboxydimethylmethyl-4-hydroxy-5-tertbutylphenyl]prop-2-en-1-one and 1-[2-hydroxy-4-chlorophenyl]-3-[3-isopropyloxycarbonyldimethylmethyl-4-hydroxy-5-tertbutylphenyl]prop-2-en-1-one:

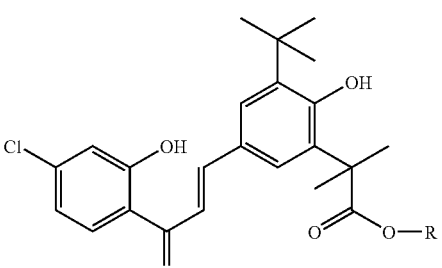

R = —H, —CH(CH₃)₂

1-[2-hydroxy-4-chlorophenyl]-3-[3,5-dimethoxy-4-carboxydimethylmethyl oxyphenyl]prop-2-en-1-one and 1-[2-hydroxy-4-chlorophenyl]-3-[3,5-dimethoxy-4-isopropyloxycarbonyldimethylmethyloxyphenyl]prop-2-en-1-one:

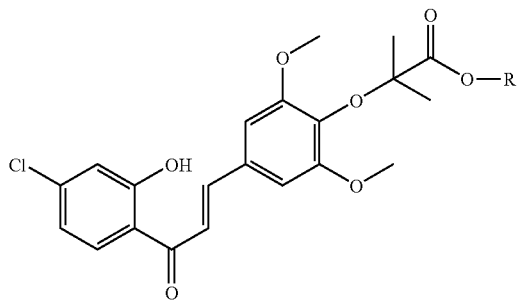

1-[2-hydroxyphenyl]-3-[3,5-dimethoxy-4-carboxydimethylmethyloxyphenyl]prop-2-en-1-one and 1-[2-hydroxyphenyl]-3-[3,5-dimethoxy-4-isopropyloxycarbonyldimethylmethyloxyphenyl]prop-2-en-1-one:

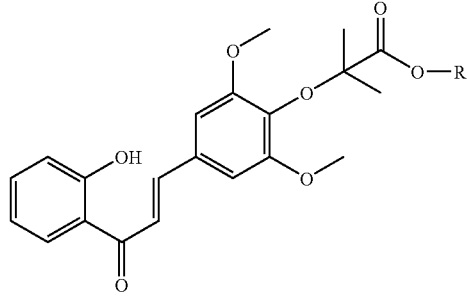

1-[2-hydroxy-4-carboxydimethylmethyloxyphenyl]-3-[3,5-dimethoxy-4-hydroxyphenyl]prop-2-en-1-one and 1-[2-hydroxy-4-isopropyloxycarbonyldimethylmethyloxyphenyl]-3-[3,5-dimethoxy-4-hydroxyphenyl]prop-2-en-1-one:

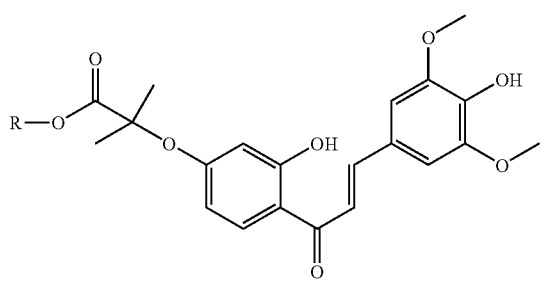

1-[2-hydroxy-4-chlorophenyl]-3-[3,4-dihydroxy-5-carboxydimethylmethyloxyphenyl]prop-2-en-1-one and 1-[2-hydroxy-4-chlorophenyl]-3-[3,4-dihydroxy-5-isopropyloxycarbonyldimethylmethyloxyphenyl]-2-propen-1-one:

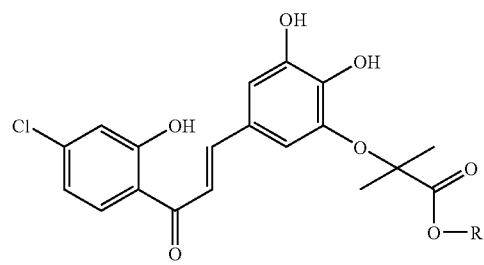

1-[2-hydroxy-4-carboxydimethylmethyloxyphenyl]-3-[3,5-dimethyl-4-hydroxyphenyl]prop-2-en-1-one and 1-[2-hydroxy-4-isopropyloxycarbonyl dimethylmethyloxyphenyl]-3-[3,5-dimethyl-4-hydroxyphenyl]prop-2-en-1-one:

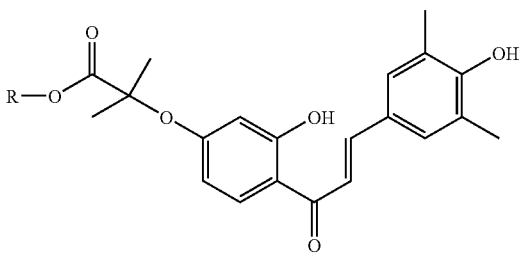

1-[2-hydroxy-4-chlorophenyl]-3-[3,5-dimethyl-4-carboxydimethylmethyl oxyphenyl]prop-2-en-1-one and 1-[2-hydroxy-4-chlorophenyl]-3-[3,5-dimethyl-4-isopropyloxycarbonyldimethylmethyloxyphenyl]prop-2-en-1-one (compound 15):

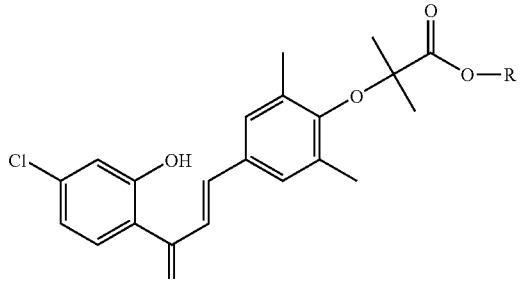

and 1-[2-hydroxyphenyl]-3-[3,5-dimethyl-4-carboxydimethylmethyloxyphenyl]prop-2-en-1-one and 1-[2-hydroxyphenyl]-3-[3,5-dimethyl-4-isopropyloxycarbonyl dimethylmethyloxyphenyl]prop-2-en-1-one:

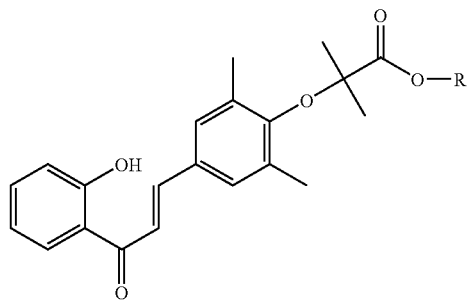

R = —H, —CH(CH₃)₂ and 1-[2-hydroxyphenyl]-3-[3-carboxydimethylmethyloxyphenyl]prop-2-en-1-one and 1-[2-hydroxyphenyl]-3-[3-isopropyloxycarbonyldimethylmethyloxyphenyl]prop-2-en-1-one:

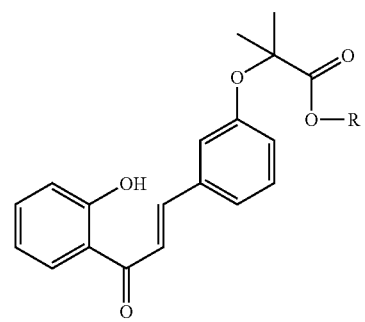

R = —H, —CH(CH₃)₂

1-[2-hydroxyphenyl]-3-[4-carboxydimethylmethylthiophenyl]prop-2-en-1-one and 1-[2-hydroxyphenyl]-3-[4-isopropyloxycarbonyldimethylmethylthiophenyl]prop-2-en-1-one (compound 18):

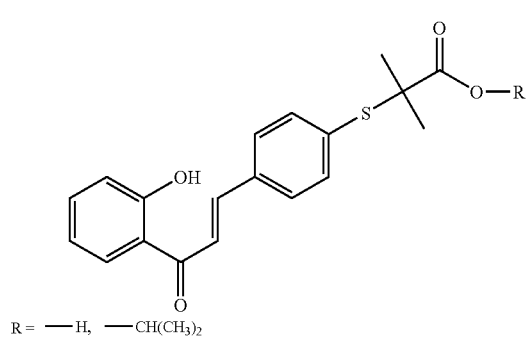

R = —H, —CH(CH₃)₂

1-[2-mercapto-4-methyloxyphenyl]-3-[4-carboxydimethylmethyloxyphenyl]prop-2-en-1-one and 1-[2-mercapto-4-methyloxyphenyl]-3-[4-isopropyloxycarbonyldimethylmethyloxyphenyl]prop-2-en-1-one:

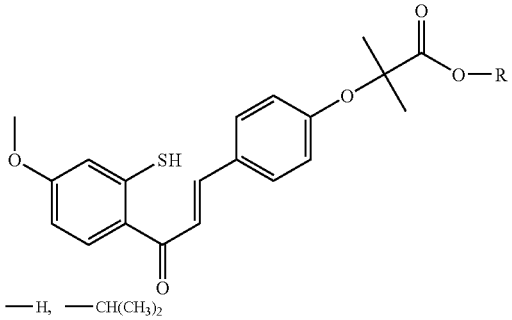

R = —H, —CH(CH₃)₂

1-[4-heptylphenyl]-3-[3-methyl-4-carboxydimethylmethyloxyphenyl]prop-2-en-1-one and 1-[4-heptylphenyl]-3-[3-methyl-4-isopropyloxycarbonyldimethylmethyloxyphenyl]prop-2-en-1-one:

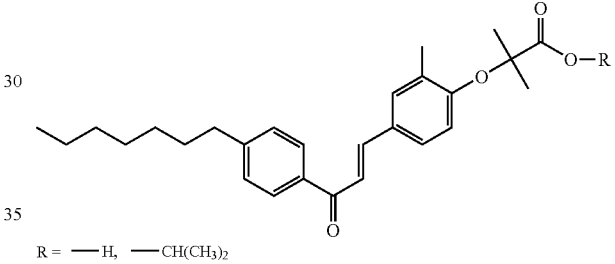

R = —H, —CH(CH₃)₂

1-[2-hydroxy-4-carboxydimethylmethyloxyphenyl]-3-[3,5-dibromo-4-hydroxyphenyl]prop-2-en-1-one,
1-[2-hydroxy-4-carboxydimethylmethyloxyphenyl]-3-[3-hydroxyphenyl]prop-2-en-1-one,
1-[2-hydroxy-4-carboxydimethylmethyloxyphenyl]-3-[4-methylthiophenyl]prop-2-en-1-one,
1-[2-hydroxy-4-carboxydimethylmethyloxyphenyl]-3-[4-methylthiophenyl]prop-2-en-1-one
1-[2,4-dihydroxyphenyl]-3-[4-carboxydimethylmethyloxyphenyl]prop-2-en-1-one,
1-[2-hydroxyphenyl]-3-[4-carboxydimethylmethyloxyphenyl]prop-2-en-1-one
1-[4-chlorophenyl]-3-[3,5-dimethyl-4-tertbutyloxycarbonyldimethylmethyloxyphenyl]prop-2-en-1-one
1-[4-chlorophenyl]-3-[3,5-dimethyl-4-isopropyloxycarbonyldimethylmethyloxyphenyl]prop-2-en-1-one,
1-[4-chlorophenyl]-3-[3,5-dimethyl-4-carboxydimethylmethyloxyphenyl]prop-2-en-1-one,
1-[2-hydroxy-4-carboxydimethylmethyloxyphenyl]-3-[4-chlorophenyl]prop-2-en-1-one,
1-[2-hydroxyphenyl]-3-[4-carboxydimethylmethylthiophenyl]prop-2-en-1-one,
1-[4-chloro-2-hydroxyphenyl]-3-[4-carboxydimethylmethylthiophenyl]prop-2-en-1-one,
1-[4-carboxydimethylmethyloxyphenyl]-3-[3,5-dimethyl-4-hydroxyphenyl]prop-2-en-1-one,
1-[4-methylthiophenyl]-3-[4-carboxydimethylmethyloxyphenyl]prop-2-en-1-one, 1-[4-carboxydimethylmethyloxyphenyl]-3-[4-chlorophenyl]prop-2-en-1-one,
1-[4-carboxydimethylmethylthiophenyl]-3-[4-methylthiophenyl]prop-2-en-1-one,
1-[2-hydroxy-4-bromophenyl]-3-[3,5-dimethyl-4-carboxydimethylmethyloxyphenyl]prop-2-en-1-one,
1-[4-carboxydimethylmethyloxyphenyl]-3-[4-methylthiophenyl]prop-2-en-1-one,
1-[4-methylthiophenyl]-3-[3,5-dimethyl-4-tertbutyloxycarbonyldimethylmethyloxyphenyl]prop-2-en-1-one,
1-[4-methylthiophenyl]-3-[3,5-dimethyl-4-isopropyloxycarbonyldimethylmethyloxyphenyl]prop-2-en-1-one,
1-[4-methylthiophenyl]-3-[3,5-dimethyl-4-carboxydimethylmethyloxyphenyl]prop-2-en-1-one,
1-[2-methoxyphenyl]-3-[3,5-dimethyl-4-tertbutyloxycarbonyldimethylmethyloxyphenyl]prop-2-en-1-one,
1-[2-methoxyphenyl]-3-[3,5-dimethyl-4-carboxydimethylmethyloxyphenyl]prop-2-en-1-one,
1-[4-hexyloxyphenyl]-3-[3,5-dimethyl-4-tertbutyloxycarbonyldimethylmethyloxyphenyl]prop-2-en-1-one,
1-[4-hexyloxyphenyl]-3-[3,5-dimethyl-4-carboxydimethylmethyloxyphenyl]prop-2-en-1-one,
2-(3,5-dimethyl-4-tertbutyloxycarbonyldimethylmethyloxyphenyl)-7-chloro-4H-1-benzopyran-4-one,
2-(3,5-dimethyl-4-carboxydimethylmethyloxyphenyl)-7-chloro-4H-1-benzopyran-4-one,
1-[2-methyloxy-chlorophenyl]-3-[3,5-dimethyl-4-tertbutyloxycarbonyldimethylmethyloxyphenyl]prop-2-en-1-one,
1-[2-methyloxy-4-chlorophenyl]-3-[3,5-dimethyl-4-carboxydimethylmethyloxyphenyl]prop-2-en-1-one,
1-[4-heptylphenyl]-3-[3,5-dimethyl-4-tertbutyloxycarbonyldimethylmethyloxyphenyl]prop-2-en-1-one,
1-[4-heptylphenyl]-3-[3,5-dimethyl-4-carboxydimethylmethyloxyphenyl]prop-2-en-1-one,
1-[4-bromophenyl]-3-[3,5-dimethyl-4-tertbutyloxycarbonyldimethylmethyloxyphenyl]prop-2-en-1-one,
1-[4-bromophenyl]-3-[3,5-dimethyl-4-carboxy dimethylmethyloxyphenyl]prop-2-en-1-one,
1-[2-hydroxyphenyl]-3-[3,5-dimethyl-4-isopropyloxycarbonyldimethylmethyloxyphenyl]prop-2-en-1-one.

The method according to the invention comprises contacting in basic medium or in acidic medium at least one compound represented by formula (A) with at least one compound represented by formula (B), formulas (A) and (B) being:

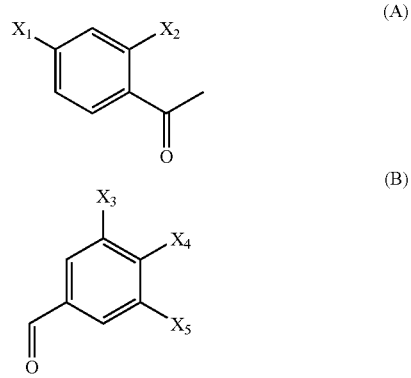

formulas in which X1, X2, X3, X4 and X5 are such as defined hereinabove.

The conditions for carrying out said reaction in acidic or basic medium are within reach of those skilled in the art and wide variations are possible.

Said two compounds are advantageously contacted in stoichiometric proportions. Contact is preferably done at room temperature (between approximately 18° C. and 25° C.) and at atmospheric pressure.

In basic medium, the reaction is preferably carried out in the presence of a strong base, such as an alkaline earth metal hydroxide, like sodium hydroxide or an alkaline metal alcoholate like sodium ethylate.

In acidic medium, the reaction is preferably carried out in the presence of a strong acid, such as hydrochloric acid.

The reaction pathway may be depicted as follows:

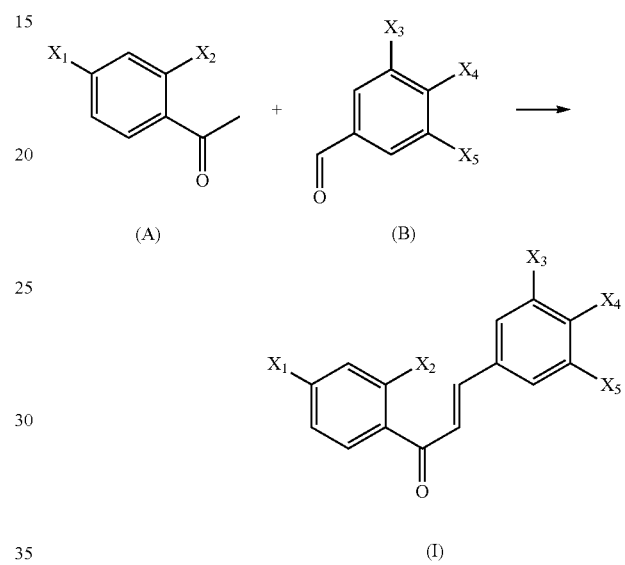

The synthesis in basic medium may be carried out in the following manner:

One molar equivalent of ketone (compound (A)) and one molar equivalent of aldehyde (compound (B)) are solubilized in a hydroalcoholic solution of 20 molar equivalents of sodium hydroxide. The mixture is stirred for approximately 18 hours at room temperature (between 18° C. and 25° C.). The medium is then acidified (in particular to a pH of approximately 2) in particular with hydrochloric acid. The expected substituted 1,3-diphenylprop-2-en-1-one can be obtained by precipitation or solid/liquid extraction after evaporation of the reaction medium. It can then be purified by silica gel chromatography or by crystallization.

The synthesis in acidic medium may be carried out in the following manner:

One molar equivalent of ketone (compound (A)) and one molar equivalent of aldehyde (compound (B)) are solubilized in an ethanol solution saturated with gaseous hydrochloric acid. The mixture is stirred at room temperature for approximately 6 hours, the solvent is eliminated, in particular by vacuum evaporation. The substituted 1,3-diphenylprop-2-en-1-one is purified, in particular by chromatography on silica gel.

The method for preparing compounds represented by formula (I) allows the preparation of compounds referred to hereinbelow as starting materials and intermediate compounds. The invention also has as its object certain starting materials and intermediate compounds obtained as provided for in the invention.

Said compounds (starting materials and intermediates) are more particularly selected in the group consisting of:
1-[4-chlorophenyl]-3-[3,5-dimethyl-4-hydroxyphenyl]prop-2-en-1-one (intermediate compound 1),
4-ethyloxycarbonyl dimethylmethylthioacetophenone (starting material 12),
1-[4-methylthiophenyl]-3-[3,5-dimethyl-4-hydroxyphenyl]prop-2-en-1-one (intermediate compound 2),
1-[2-methoxyphenyl]-3-[3,5-dimethyl-4-hydroxyphenyl]prop-2-en-1-one (intermediate compound 3),
1-[4-hexyloxyphenyl]-3-[3,5-dimethyl-4-hydroxyphenyl]prop-2-en-1-one (intermediate compound 4),
1-[2-hydroxy-4-chlorophenyl]-3-[3,5-dimethyl-4-hydroxyphenyl]prop-2-en-1-one (intermediate compound 5),
2-(3,5-dimethyl-4-hydroxyphenyl)-7-chloro-4H-1-benzopyran-4-one (intermediate compound 6),
1-[2-methyloxy-4-chlorophenyl]-3-[3,5-dimethyl-4-hydroxydimethylmethyloxyphenyl]prop-2-en-1-one (intermediate compound 7),
1-[4-heptylphenyl]-3-[3,5-dimethyl-4-hydroxyphenyl]prop-2-en-1-one (intermediate compound)
1-[4-bromophenyl]-3-[3,5-dimethyl-4-hydroxyphenyl]prop-2-en-1-one (intermediate compound 8)

Another object of the invention concerns any pharmaceutical composition comprising at least one compound represented by formula (I) such as defined hereinabove in a pharmaceutically acceptable support.

In an advantageous manner it is a pharmaceutical composition for the treatment or prophylaxis of cerebrovascular diseases and more particularly cerebral ischemia or cerebrovascular accidents. In fact, it was found in a surprising manner that compounds represented by formula (I) exhibit PPAR activator, antioxidant and anti-inflammatory properties and have prophylactic and acute neuroprotective activity in cerebral ischemia.

The invention also concerns the use of a compound such as defined hereinabove for preparing a pharmaceutical composition for practicing a method of treatment or prophylaxis of the human or animal body.

The invention also concerns the use, for preparing a pharmaceutical composition for curative or preventive treatment of cerebrovascular diseases and more particularly cerebral ischemia, of a compound represented by formula (I), including compounds having general formula (I) in which:

$X_1$, $X_2$, $X_3$ and $X_5$ each represent a hydrogen atom, $X_6$ represents an oxygen atom and $X_4$ represents a group corresponding to the formula —O—$CR_8R_9$—$COOR_{10}$, where $R_8$ and $R_9$, which are the same or different, represent a C1 to C2 alkyl group, and $R_6$ represents a hydrogen atom or a C1 to C7 alkyl group, $X_2$, $X_3$ and $X_5$ each represent a hydrogen atom, $X_1$ represents a halogen atom or a R1 or -G1R1 group, where R1 represents an unsubstituted C1 to C2 alkyl group and G1 represents an oxygen atom, $X_6$ represents an oxygen atom and $X_4$ represents a group corresponding to the formula —O—$CR_{11}R_{12}$—$COOR_{10}$, where $R_{11}$ and $R_{12}$, which are the same or different, represent a hydrogen atom or a C1 to C2 alkyl group, and $R_{10}$ represents a hydrogen atom or a C1 to C7 alkyl group and $X_2$ represents a hydrogen atom and X1 represents -G1R1 where G1 represents an oxygen atom and R1 represents CH2COOH.

The invention also concerns a method for treating cerebrovascular diseases and more particularly cerebral ischemia, comprising administering to a subject, particularly human, an effective dose of a compound or pharmaceutical composition such as defined hereinabove, including compounds represented by general formula (I) in which:

$X_1$, $X_2$, $X_3$ and $X_5$ each represent a hydrogen atom, $X_6$ represents an oxygen atom and $X_4$ represents a group corresponding to the formula —O—$CR_8R_9$—$COOR_{10}$, where $R_8$ and $R_9$, which are the same or different, represent a C1 to C2 alkyl group and $R_6$ represents a hydrogen atom or a C1 to C7 alkyl group, $X_2$, $X_3$ and $X_5$ each represent a hydrogen atom, $X_1$ represents a halogen atom or a R1 or -G1R1 group, where R1 represents an unsubstituted C1 to C2 alkyl group and G1 represents an oxygen atom, $X_6$ represents an oxygen atom and $X_4$ represents a group corresponding to the formula —O—$CR_{11}R_{12}$—$COOR_{10}$, where $R_{11}$ and $R_{12}$, which are the same or different, represent a hydrogen atom or a C1 to C2 alkyl group, and $R_{10}$ represents a hydrogen atom or a C1 to C7 alkyl group, and $X_2$ represents a hydrogen atom and $X_1$ represents -G1R1 where G1 represents an oxygen atom and R1 represents CH2COOH.

Preferably, the method for treating cerebrovascular diseases and more particularly cerebral ischemia, comprises administering to a subject, particularly human, an effective dose of a compound represented by formula (I) or a pharmaceutical composition such as defined hereinabove, with the exception of compounds having general formula (I) in which:

$X_1$, $X_2$, $X_3$ and $X_5$ each represent a hydrogen atom, $X_6$ represents an oxygen atom and $X_4$ represents a group corresponding to the formula —O—$CR_8R_9$—$COOR_{10}$, where $R_8$ and $R_9$, which are the same or different, represent a C1 to C2 alkyl group, and $R_6$ represents a hydrogen atom or a C1 to C7 alkyl group, $X_2$, $X_3$ and $X_5$ each represent a hydrogen atom, $X_1$ represents a halogen atom or a R1 or -G1R1 group, where R1 represents an unsubstituted C1 to C2 alkyl group and G1 represents an oxygen atom, $X_6$ represents an oxygen atom and $X_4$ represents a group corresponding to the formula —O—$CR_{11}R_{12}$—$COOR_{10}$, where $R_{11}$ and $R_{12}$, which are the same or different, represent a hydrogen atom or a C1 to C2 alkyl group, and $R_{10}$ represents a hydrogen atom or a C1 to C7 alkyl group, and $X_2$ represents a hydrogen atom and $X_1$ represents -G1R1 where G1 represents an oxygen atom and R1 represents CH2COOH.

The pharmaceutical compositions according to the invention advantageously comprise one or more pharmaceutically acceptable excipients or vehicles. Examples include saline, physiological, isotonic, buffered solutions and the like, compatible with pharmaceutical use and known to those skilled in the art. The compositions may contain one or more agents or vehicles selected in the group consisting of dispersants, solubilizers, stabilizers, preservatives, and the like. Agents or vehicles that can be used in the formulations (liquid and/or injectable and/or solid) are in particular methylcellulose, hydroxymethylcellulose, carboxymethylcellulose, polysorbate 80, mannitol, gelatin, lactose, plant oils, acacia, and the like. The compositions may be formulated as suspensions for injection, gels, oils, tablets, suppositories, powders, capsules, gelules, and the like, possibly by means of pharmaceutical forms or devices ensuring prolonged and/or delayed release. For this type of formulation, an agent such as cellulose, carbonates or starches is advantageously used.

The inventive compounds or compositions may be administered in different ways and in different forms. For instance, they may be administered by the oral or systemic route, such as for example by the intravenous, intramuscular, subcutaneous, transdermal, intra-arterial route, etc. For injections, the compounds are generally formulated as liquid suspensions, which can be injected through syringes or by infusion, for example. It is understood that the injection rate and/or the injected dose may be adapted by those skilled in the art according to the patient, the pathology, the method of administration, etc. Typically, the compounds are administered at doses ranging from 1 µg to 2 g per administration, preferably from 0.1 mg to 1 g per administration. The administrations may be given daily or repeated several times a day, as the case may be. Moreover, the inventive compositions may additionally comprise other active ingredients or agents.

LEGENDS OF FIGURES

FIG. 1-1, 1-2, 1-3: Evaluation of the antioxidant properties of compound 2, compound 3, compound 12, compound 14 and compound 17 on LDL oxidation by copper (Cu).

FIG. 1-1 shows the results of the experiment measuring formation of conjugated dienes over time. It can be seen that incubation of LDL with the test compounds at a concentration of $10^{-4}$M delayed conjugated diene formation. The lag phase was 111 minutes for copper alone as compared with a lag phase of 132, 145, 134 and 203 minutes, respectively, when LDL were incubated with compound 3, compound 12, compound 14, compound 17. The lag phase was greater than 480 minutes when LDL were incubated with compound 2. This lag in the formation of conjugated dienes is characteristic of antioxidants.

FIG. 1-2 shows the rate of diene formation after different treatments. Incubation of the compounds with LDL in the presence of copper slowed the rate of conjugated diene formation. This rate was 2 nmol/min/mg of LDL with copper alone, 1.7 nmol/min/mg of LDL when LDL were incubated in the presence of $10^{-4}$M compound 17, and not determined for compound 2 at $10^{-4}$M (not measurable because too low).

FIG. 1-3 represents the maximum amount of conjugated dienes formed over time. Incubation of LDL with copper led to formation of 348 nmol of conjugated dienes per mg of LDL; incubation with compound 2 at $10^{-4}$M led to an 84% decrease in conjugated diene formation (54.4 nmol per mg of LDL). In the presence of compounds 3 and 17, conjugated diene formation was respectively 303 and 327 nmol per mg of LDL.

FIGS. 1-4, 1-5, 1-6: Evaluation of the antioxidant propreties of compound 18, compound 19, compound 21 and compound 22 on LDL oxidation by copper (Cu).

FIG. 1-4 shows that incubation of LDL with the test compounds at a concentration of $10^{-4}$M delayed conjugated diene formation. The lag phase was 178 minutes for copper alone as compared with a lag phase of 241, 182 and 241 minutes (from the experimental deterimation), respectively, when LDL were incubated with compound 18, compound 19, or compound 22. The lag phase was more than 480 minutes when LDL were incubated with compound 21. This lag in the formation of conjugated dienes is characteristic of antioxidants.

FIG. 1-5 shows the rate of diene formation after different treatments. The rate of formation of conjugated dienes was 1.6 nmol/min/mg of LDL with copper alone, 1.4 nmol/min/mg of LDL when LDL were incubated in the presence of compound 18 at $10^{-4}$M, 1.3 nmol/min/mg of LDL when LDL were incubated in the presence of compounds 22, and not determined for compound 21 at $10^{-4}$M (not measurable because too low).

FIG. 1-6 represents the maximum amount of conjugated dienes formed over time. Incubation of LDL with copper led to formation of 353 nmol of conjugated dienes per mg of LDL. Incubation with compound 21 at $10^{-4}$M inhibited conjugated diene formation. Conjugated diene formation was respectively 305, 345 and 345 nmol per mg of LDL in the presence of compounds 18, 19 and 22.

FIGS. 1-7, 1-8: Evaluation of the antioxidant properties of compound 25 and compound 28 on LDL oxidation by copper (Cu).

FIG. 1-7 shows the results of the experiment measuring formation of conjugated dienes over time. It can be seen that incubation of LDL with the test compounds at a concentration of $10^{-4}$M delayed conjugated diene formation. The lag phase was 82 minutes for copper alone as compared with a lag phase of 120 and 135 minutes (from the experimental determination), respectively, when LDL were incubated with compound 25 and compound 29.

FIG. 1-8 represents the maximum amount of conjugated dienes formed over time. Incubation of LDL with copper led to formation of 393 nmol of conjugated dienes per mg of LDL. In the presence of compound 25 this value was 378 nmol per mg of LDL.

FIGS. 1-9, 1-10, 1-11: Evaluation of the antioxidant properties of compound 31, compound 33 and compound 35 on LDL oxidation by copper (Cu).

FIG. 1-9 shows the results of the experiment measuring formation of conjugated dienes over time. It can be seen that incubation of LDL with the test compounds at a concentration of $10^{-4}$M delayed conjugated diene formation. The lag phase was 80 minutes for copper alone as compared with a lag phase of 139, 247 and 149 minutes (from the experimental determination), respectively, when LDL were incubated with compound 31, compound 33, and compound 35. This lag in the formation of conjugated dienes is characteristic of antioxidants.

FIG. 1-10 shows the rate of diene formation after different treatments. Incubation of the compounds with LDL in the presence of copper slowed the rate of conjugated diene formation. This rate was 1.9 nmol/min/mg of LDL with copper alone, 1.6 nmol/min/mg of LDL when LDL were incubated in the presence of compound 31 at $10^{-4}$M, 0.8 nmol/min/mg of LDL when LDL were incubated in the presence of compound 33 and 1.5 nmol/min/mg of LDL when LDL were incubated in the presence of compound 35.

FIG. 1-11 represents the maximum amount of conjugated dienes formed over time. Incubation of LDL with copper led to formation of 298 nmol of conjugated dienes per mg of LDL, as compared with 257 nmol per mg of LDL in the presence of compound 33.

FIGS. 1-12, 1-13, 1-14: Evaluation of the antioxidant properties of compound 37, compound 38 and compound 41 on LDL oxidation by copper (Cu).

FIG. 1-12 shows the results of the experiment measuring formation of conjugated dienes over time. It can be seen that incubation of LDL with the test compounds at a concentration of $10^{-4}$M delayed conjugated diene formation. The lag phase was 120 minutes for copper alone as compared with a lag phase of 196, 284 and 411 minutes (from the experimental determination), respectively, when LDL were incubated with compound 37, compound 38, and compound 41.

FIG. 1-13 shows the rate of diene formation after different treatments. Incubation of the compounds with LDL in the presence of copper slowed the rate of conjugated diene formation. This rate was 1.8 nmol/min/mg of LDL with copper alone, 1.49 nmol/min/mg of LDL when LDL were incubated in the presence of compounds 37 at $10^{-4}$M, 0.71 nmol/min/mg of LDL when LDL were incubated in the presence of compounds 38 and 0.54 nmol/min/mg of LDL when LDL were incubated in the presence of compounds 41.

FIG. 1-14 represents the maximum amount of conjugated dienes formed over time. Incubation of LDL with copper led to formation of 372 nmol of conjugated dienes per mg of LDL, as compared with 338 nmol per mg of LDL, 244 nmol per mg of LDL, and 71 nmol per mg of LDL in the presence of compounds 37, 38 and 41, respectively.

The lag phase in the formation of conjugated dienes, the reduction in the rate of diene formation and the decrease in the total amount of dienes formed are characteristics of antioxidants.

FIGS. 2-1, 2-2, 2-3, 2-4, 2-5, 2-6: Evaluation of PPARα agonist properties of the inventive compounds in the PPARα/Gal4 transactivation system.

RK13 cells were incubated with the different compounds at concentrations of 10, 30 and 100 μM or 1, 10 and 100 μM for 24 hours. The results are expressed as the induction factor (luminescent signal relative to untreated cells) after the different treatments. The higher the induction factor the more potent the PPARα agonist activity.

FIG. 2-1:

The results show the induction factors for compound 3, compound 4, compound 7, compound 8 and compound 9. The values of these induction factors are given in Table 2-1.

TABLE 2-1

| Compound | Concentration | Induction factor |
|---|---|---|
| Cp3 | 10 μM | 30.12 |
|  | 30 μM | 27.27 |
|  | 100 μM | 25.84 |
| Cp4 | 10 μM | 3.99 |
|  | 30 μM | 22.15 |
|  | 100 μM | 61.07 |
| Cp7 | 10 μM | 36.48 |
|  | 30 μM | 50.37 |
|  | 100 μM | 37.84 |
| Cp8 | 10 μM | 0.62 |
|  | 30 μM | 1.27 |
|  | 100 μM | 9.98 |
| Cp9 | 10 μM | 2.11 |
|  | 30 μM | 5.00 |
|  | 100 μM | 28.19 |

The results show that compound 3 produced a maximum 27-fold induction at a concentration of 30 μM, compound 4 had a maximum induction factor of 60 at 100 μM, 22 at 30 μM and 4 at 10 μM. Compound 7 had a maximum induction factor of 50 at 100 μM. Compound 8 activated the system with a maximum induction factor of 10 at 100 μM. Compound 9 had an induction factor of 28 at 100 μM, the highest concentration.

FIG. 2-2:

The results show the induction factors for compound 11, compound 12, compound 13, compound 14 and compound 17. The values of these induction factors are given in Table 2-2.

TABLE 2-2

| Compound | Concentration | Induction factor |
|---|---|---|
| Cp11 | 1 μM | 1.20 |
|  | 10 μM | 1.39 |
|  | 100 μM | 10.19 |
| Cp12 | 1 μM | 1.12 |
|  | 10 μM | 8.45 |
|  | 100 μM | 22.54 |

TABLE 2-2-continued

| Compound | Concentration | Induction factor |
|---|---|---|
| Cp13 | 1 μM | 1.20 |
|  | 10 μM | 1.10 |
|  | 100 μM | 1.5 |
| Cp14 | 1 μM | 1.25 |
|  | 10 μM | 1.36 |
|  | 100 μM | 1.38 |
| Cp17 | 1 μM | 79.76 |
|  | 10 μM | 85.69 |
|  | 100 μM | 13.80 |

The results show that compound 11 produced a maximum 10-fold induction at a concentration of 100 μM, compound 12 had a maximum induction factor of 22 at 100 μM, 8 at 30 μM and 1 at 10 μM. Compounds 13 and 14 had induction factors comprised between 1.1 and 1.5 at the different concentrations tested. Compound 17 activated the system with a maximum induction factor of 85 at 10 μM and a minimum induction factor of 13.8 at the 100 μM concentration.

FIG. 2-3

The results show the induction factors for compound 19, compound 20, compound 21 and compound 22. The values of these induction factors are given in Table 2-3.

TABLE 2-3

| Compound | Concentration | Induction factor |
|---|---|---|
| Cp19 | 1 μM | 1.20 |
|  | 10 μM | 15.62 |
|  | 100 μM | 0.07 |
| Cp20 | 1 μM | 21.50 |
|  | 10 μM | 53.45 |
|  | 100 μM | 1.22 |
| Cp21 | 1 μM | 0.78 |
|  | 10 μM | 1.10 |
|  | 100 μM | 22.80 |
| Cp22 | 1 μM | 2.40 |
|  | 10 μM | 49.49 |
|  | 100 μM | 2.73 |

The results show that compound 19 produced a maximum 15.6-fold induction at 10 μM, compound 20 had a maximum induction factor of 53 at 10 μM. Compound 21 had induction factors comprised between 0.8 and 22 at the different concentrations tested. Compound 22 activated the system with a maximum induction factor of 50 at the 10 μM concentration.

FIG. 2-4

The results show the induction factors for compound 23, compound 24, compound 25, compound 26 and compound 29. The values of these induction factors are given in Table 2-4.

TABLE 2-4

| Compound | Concentration | Induction factor |
|---|---|---|
| Cp23 | 1 μM | 1.55 |
|  | 10 μM | 3.67 |
|  | 100 μM | 0.12 |
| Cp24 | 1 μM | 2.06 |
|  | 10 μM | 11.62 |
|  | 100 μM | 0.00 |
| Cp25 | 1 μM | 13.48 |
|  | 10 μM | 21.03 |
|  | 100 μM | 7.01 |

TABLE 2-4-continued

| Compound | Concentration | Induction factor |
|---|---|---|
| Cp26 | 1 µM | 1.75 |
|  | 10 µM | 7.85 |
|  | 100 µM | 1.08 |
| Cp29 | 1 µM | 28.36 |
|  | 10 µM | 25.26 |
|  | 100 µM | 0.27 |

Compound 23 had a maximum induction factor of 3.6 at 10 µM, compound 24 had a maximum induction factor of 11 at 10 µM. Compound 25 activated the system with induction factors comprised between 7 and 21 according to the concentrations tested. Compound 26 had a maximum induction factor of 7.8 for the 10 µM concentration, compound 29 had induction factors of 28 and 25 at 1 and 10 µM, respectively.

FIG. 2-5

The results show the induction factors for compound 31 and compound 33. The values of these induction factors are given in Table 2-5.

TABLE 2-5

| Compound | Concentration | Induction factor |
|---|---|---|
| Cp31 | 1 µM | 3.77 |
|  | 10 µM | 15.52 |
|  | 100 µM | 1.21 |
| Cp33 | 1 µM | 22.05 |
|  | 10 µM | 44.52 |
|  | 100 µM | 77.62 |

Compound 31 activated the system with an induction factor of 15.5 at the concentration of 10 µM. The induction factors for compound 33 were 22, 44 and 77 for the 1, 10 and 100 µM concentrations, respectively.

FIG. 2-6

The results show the induction factors for compound 37, compound 38 and compound 41. The values of these induction factors are given in Table 2-6.

TABLE 2-6

| Compound | Concentration | Induction factor |
|---|---|---|
| Cp37 | 1 µM | 24.55 |
|  | 10 µM | 27.83 |
|  | 100 µM | 0.02 |
| Cp38 | 1 µM | 14.70 |
|  | 10 µM | 22.22 |
|  | 100 µM | 0.311 |
| Cp41 | 1 µM | 34.61 |
|  | 10 µM | 31.18 |
|  | 100 µM | 3.39 |

The maximum induction factors for compounds 37, 38 and 41 were 27, 22 and 31, respectively, at the 10 µm concentration.

These results demonstrate that the inventive compounds tested exhibit PPARα ligand activity and therefore enable the transcriptional activation thereof.

FIG. 2-7: Evaluation of PPARγ agonist properties of the inventive compounds in the PPARγ/Gal4 transactivation system.

RK13 cells were incubated with the different compounds at concentrations of 1, 10 and 100 µM for 24 hours. The results are expressed as the induction factor (luminescent signal relative to untreated cells) after the different treatments. The higher the induction factor the more potent the PPARγ agonist activity.

The results in the figure show the induction factors for compound 17, compound 33, and compound 29. The values of these induction factors are given in Table 2-7.

TABLE 2-7

| Compound | | Induction factor |
|---|---|---|
| Cp17 | 1 µM | 15.37 |
|  | 10 µM | 24.92 |
|  | 100 µM | 6.13 |
| Cp33 | 1 µM | 15.65 |
|  | 10 µM | 33.90 |
|  | 100 µM | 45.58 |
| Cp29 | 1 µM | 17.05 |
|  | 10 µM | 33.89 |
|  | 100 µM | 0.01 |

The results show that compound 17 had a maximum induction factor of 25 at 10 µM. Compound 33 had a maximum induction factor of 45.6 at 100 µM and compound 29 of 33.9 at 10 µM.

These results demonstrate that the inventive compounds tested exhibit PPARγ ligand activity and therefore enable the transcriptional activation thereof.

FIGS. 3-1 and 3-2:

Evaluation of the acute and prophylactic neuroprotective properties of the inventive compounds FIG. 3-1: Prophylactic Neuroprotection.

This figure shows infarct volume in mm3 measured after intraluminal occlusion of the middle cerebral artery for 60 minutes followed by reperfusion for 24 hours before sacrifice. FIG. 3-1 shows infarct volume observed with three groups of C57Black/6 mice. Two of these animal groups were treated by gavage with compound 15 at 200 mg/kg/day or with compound 42 at 200 mg/kg/day for 14 days before occlusion.

It can be seen that infarct volume in untreated animals was 37 mm3 as compared with 24 mm3 for animals treated with compound 42 and 32 mm3 with compound 15.

FIG. 3-2: Acute Neuroprotection.

FIG. 3-2 shows infarct volume observed with three groups of C57 black/6 mice. Animals were treated with compound 15 at 200 mg/kg/day or with compound 42 at 200 mg/kg/day for 72 hours after occlusion.

It can be seen that total corrected infarct volume in untreated animals was 50 mm3 as compared with 39 mm3 for animals treated with compound 42 and 43 mm3 with compound 15.

The results presented in FIGS. 3-1 and 3-2 demonstrate the efficacy of the compounds as neuroprotective compounds. Said compounds are active as prophylactic treatment and as acute treatment.

Other aspects and advantages of the invention will become apparent in the following examples, which are given for purposes of illustration and not by way of limitation.

EXAMPLES

The inventive compounds were prepared according to the general methods outlined below.

Description of General Synthetic Methods of the Invention

Synthesis of 1,3-diphenylprop-2-en-1-ones

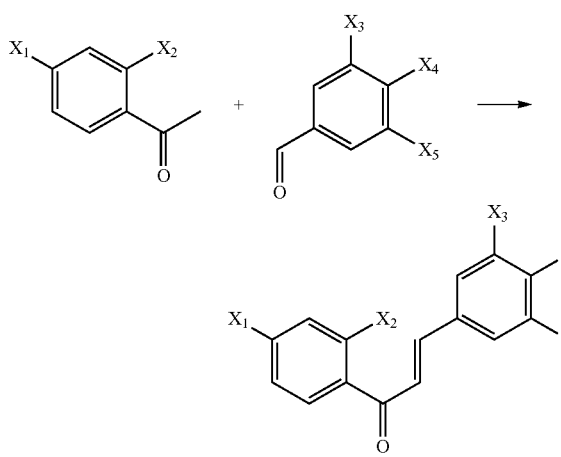

X1 = OH, Cl, Br—SCH3, ——OC6H13, ——C7H15, OC(CH3)2COOR6, SC(CH3)2COOR6,
X2 = H, O(2-phenyl-4-H-1-benzopyran-4-one), OCH3, OH
X4 = OH, Cl, Br, ——SCH3, OC(CH3)2COOR6, SC(CH3)2COOR6
X3 and X5 = CH3, C(CH3)3, OCH3, OH, OC(CH3)2COOR6
R6 = CH2CH3, H

General Method 1

Synthesis of 1,3-diphenylprop-2-en-1-ones in acidic medium

The ketone (1 eq) and the aldehyde (1 eq) were dissolved in ethanol solution saturated with gaseous hydrochloric acid. The reaction was stirred at room temperature for 6 hours and the solvent was then eliminated by vacuum evaporation. 1,3-diphenylprop-2-en-1-one was purified by chromatography on silica gel.

General Method 2

Synthesis of 1,3-diphenylprop-2-en-1-ones in basic medium

The ketone (1 eq) and the aldehyde (1 eq) were dissolved in a hydroalcoholic solution of sodium hydroxide (20 eq). The mixture was stirred at room temperature for 18 hours. The medium was acidified to pH=2 with hydrochloric acid. 1,3-diphenylprop-2-en-1-one was obtained by precipitation or solid/liquid extraction after evaporation of the reaction medium. It was purified by silica gel chromatography or by recrystallization.

General Method 3

Synthesis of substituted 1,3-diphenylprop-2-en-1-ones in the presence of sodium ethylate Sodium (1 eq) was dissolved in absolute ethanol. The ketone (1 eq) and the aldehyde (1 eq) were added. The reaction mixture was stirred at room temperature for 12 hours and 2 N sodium hydroxide (5 eq) was then added. The mixture was kept at 100° C. for 12 hours. The reaction medium was acidified by adding 6 N aqueous hydrochloric acid solution. The solvent was eliminated by vacuum evaporation. The residue was purified by chromatography on silica gel or by recrystallization.

O-Alkylation of Phenols and S-Alkylation of Thiophenols

General Method 4

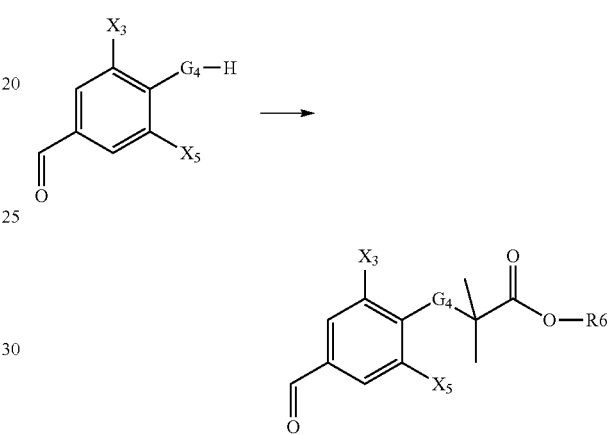

G4 = O, S
X3, X5 = H, CH3, OCH3
R6 = CH2CH3

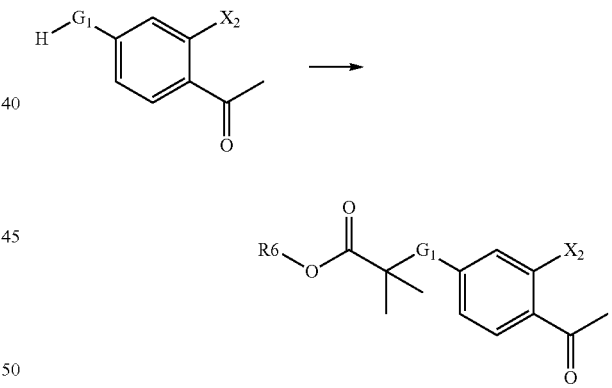

G1 = O, S
X2 = H, OH
R6 = CH2CH3

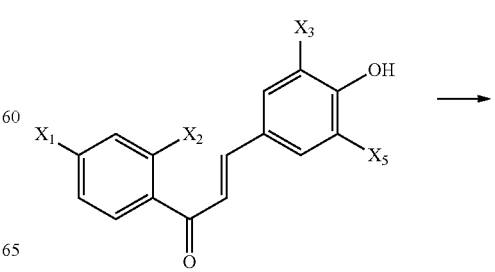

-continued

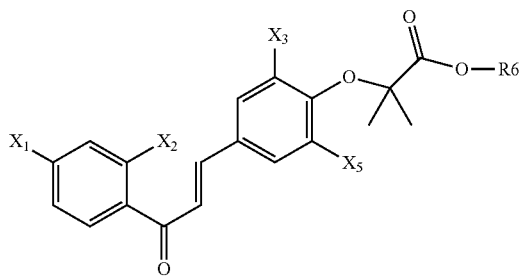

X1 = Cl, Br——SCH3, ——OC6H13, ——C7H15
X2 = H, O(2-phenyl-4-H-1-benzopyran-4-one), OCH3
X3 and X5 = CH3
R6 = CH2CH3, H The phenol (1 eq) was dissolved in acetonitrile. The halogenated derivative (1 to 10 eq) and potassium carbonate (5 eq) were then added. The reaction medium was briskly stirred under reflux for approximately 10 hours. The salts were eliminated by filtration, the solvent and excess reagent were eliminated by vacuum evaporation, and the expected product was purified by silica gel chromatography.

Acid Hydrolysis of Tertbutylic Esters

General Method 5

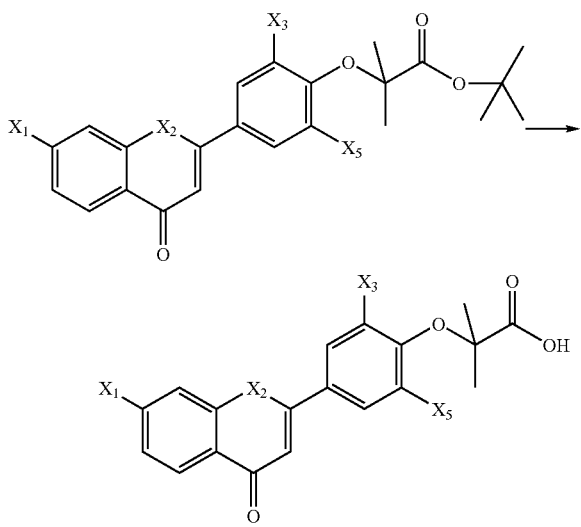

X3 and X5 = CH3,
X2 = H, O(2-phenyl-4-H-1-benzopyran-4-one), OCH3,
X1 = Cl, Br, ——SCH3, OC6H13, ——C7H15

The tertbutylic ester (1 eq) was dissolved in dichloromethane, trifluoroacetic acid (10 eq) was added, and the mixture was stirred at room temperature for 12 hours. The resulting product was purified by chromatography on silica gel or by recrystallization.

Synthesis of Starting Materials Used to Synthesize the Inventive Compounds

Starting Material 1

2'-Hydroxy-4'-(ethoxycarbonyldimethylmethoxy) acetophenone

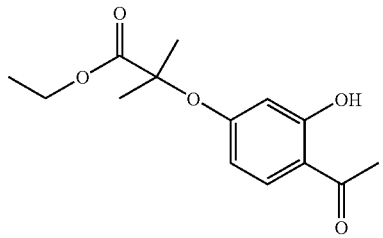

This compound was synthesized from 2',4'-dihydroxyacetophenone and ethyl bromoisobutyrate (1 eq) according to general method 4 described earlier. It was purified by chromatography on silica gel (elution:cyclohexane/ethyl acetate 9:1). 1H NMR CDCl$_3$ δppm: 1.25 (t, J=7.17 Hz, 3H), 1.67 (s, 6H), 2.56 (s, 3H), 4.24 (q, J=7.17 Hz, 2H), 6.27 (d, J=2.55 Hz, 1H), 6.37 (dd, J=2.55 Hz, J=8.72 Hz, 1H), 7.62 (d, J=8.72 Hz, 1H), 12.6 (signal, 1H).

Reference: U.S. Pat. No. 3,629,290 (1970), Fisons Pharmaceutical

Starting Material 2

3-chlorophenyl acetate

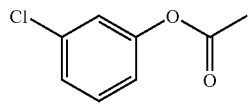

3-chlorophenol was dissolved in dichloromethane. Triethylamine (1 eq) and acetic anhydride (2 eq) were added. The mixture was stirred at room temperature for 5 hours. Solvent was eliminated by vacuum evaporation. The evaporation residue was taken up in dichloromethane, dried on magnesium sulfate and the solvent was eliminated by vacuum evaporation. Purification was by chromatography on silica gel (elution:cyclohexane/ethyl acetate 95:5). 1H NMR CDCl$_3$ δppm: 2.29 (s, 3H), 6.99-7.33 (m, 4H)

Starting Material 3

4'-Chloro-2'-hydroxyacetophenone

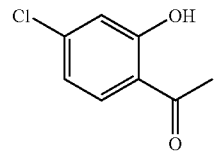

3-chlorophenyl acetate (starting material 2) was mixed with aluminium chloride (3 eq). The mixture was heated at 200° C. for 1 hour. The reaction medium was cooled to room temperature then poured in ice. The aqueous phase was extracted with methylene chloride which was dried on magnesium sulfate then vacuum evaporated.

Purification was by silica gel chromatography (elution: cyclohexane/ethyl acetate 95:5).

1H NMR CDCl$_3$ δppm: 3.41 (s, 3H), 6.81 (dd, J=8.82 Hz, J=1.47 Hz, 1H), 6.91 (d, J=1.47 Hz, 1H), 7.60 (d, 8.82 Hz, 1H), 12.33 (s, 1H)

Reference: Chen et al., J Chem Soc, 1958, 146-148.

Starting Material 4

4-Ethyloxacarbonyldimethylmethyloxybenzaldehyde

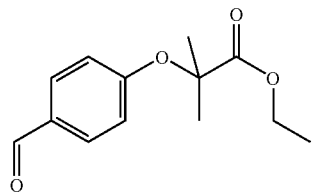

This compound was synthesized from 4-hydroxyabenzaldehyde and ethyl bromoisobutyrate according to general method 4 described earlier.

Purification was by silica gel chromatography (elution: cyclohexane/ethyl acetate 9:1).

1H NMR CDCl$_3$ δ ppm: 1.20 (t, J=6.96 Hz, 3H), 1.67 (s, 6H), 4.21 (q, J=6.96 Hz, 2H), 6.89 (d, J=8.91 Hz, 2H), 7.79 (d, J=8.94 Hz, 2H), 9.87 (S, 1H).

Starting Material 5

3,5-dimethyloxy-4-ethyloxycarbonyldimethylmethyloxybenzaldehyde

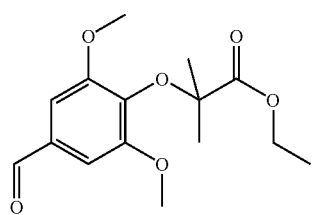

This compound was synthesized from 3,5-dimethyloxy-4-hydroxyabenzaldehyde and ethyl bromoisobutyrate according to general method 4 described earlier.

Purification was by silica gel chromatography (elution: cyclohexane/ethyl acetate 8:2).

1H NMR CDCl$_3$ δ ppm: 1.33 (t, J=7.29 Hz, 3H), 1.50 (s, 6H), 3.84 (s, 6H), 4.27 (q, J=7.29 Hz, 2H), 7.08 (s, 2H), 9.86 (s, 1H)

Starting Material 6

3,5-dimethyl-4-ethyloxycarbonyldimethylmethyloxybenzaldehyde

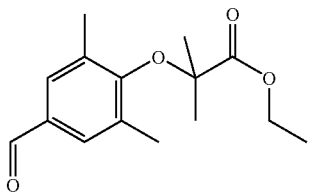

This compound was synthesized from 3,5-dimethyl-4-hydroxyabenzaldehyde and ethyl bromoisobutyrate according to general method 4 described earlier.

Purification was by silica gel chromatography (elution: cyclohexane/ethyl acetate 95:5).

1H NMR CDCl$_3$ δ ppm: 1.37 (t, J=7.14 Hz, 3H), 1.50 (s, 6H), 2.29 (s, 6H), 4.30 (q, J=7.14 Hz, 2H), 7.54 (s, 2H), 9.88 (s, 1H)

Starting Material 7

3-Ethyloxycarbonyldimethylmethyloxybenzaldehyde

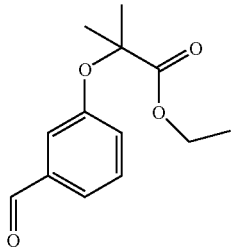

This compound was synthesized from 3-hydroxybenzaldehyde and ethyl bromoisobutyrate according to general method 4 described earlier.

Purification was by silica gel chromatography (elution: cyclohexane/ethyl acetate 9:1).

1H NMR CDCl$_3$ δ ppm: 1.24 (t, J=7.27 Hz, 3H), 1.62 (s, 6H), 4.25 (q, J=7.27 Hz, 2H), 7.11 (m, 1H), 7.31 (m, 1H), 7.40 (t, J=8.19 Hz, 1H), 7.49 (m, 1H), 9.93 (s, 1H).

Starting Material 8

4-Ethyloxycarbonyldimethylmethyl thiobenzaldehyde

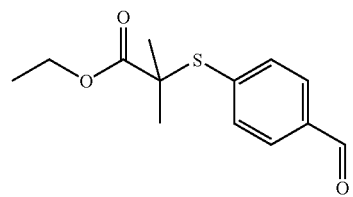

4-Methylthiobenzaldehyde (1 eq) was dissolved in methylene chloride and the solution cooled to 0° C. Metachloroperbenzoic acid (1.5 eq) was added in small fractions. The reaction was followed by thin-layer chromatography. Additional metachloroperbenzoic acid was possibly added so as to obtain total disappearance of the starting product. The precipitate was eliminated by filtration. Calcium hydroxide (1.5 eq) was added and the mixture was stirred for another 15 min. The solid was eliminated by filtration, the filtrate dried on magnesium sulfate and the methylene chloride was then eliminated by vacuum evaporation. The evaporation residue was taken up in acetic anhydride, then heated under reflux for 30 min and evaporated to dryness. The residue was taken up in methanol/triethylamine solution, stirred at room temperature for 15 minutes, then the solvents were eliminated by vacuum evaporation. The oily residue was taken up in a saturated aqueous ammonium chloride solution then extracted with methylene chloride. The organic phase was dried on magnesium sulfate and vacuum evaporated.

The resulting 4-mercaptobenzaldehyde intermediate was used without further purification. It was alkylated according to general method 4 to yield 4-ethyloxycarbonyldimethylmethylthiobenzaldehyde.

Purification was by silica gel chromatography (elution: cyclohexane/ethyl acetate 9:1).

1H NMR CDCl₃ δ ppm: 1.22 (t, J=7.46 Hz, 3H), 2.60 (s, 6H), 4.15 (q, J=7.46 Hz, 2H), 7.53 (d, J=8.38 Hz, 2H), 7.88 (d, J=8.39 Hz, 2H), 9.99 (s, 1H)

Reference: Young N R, Gauthier J Y., Coombs W. (1984). Tetrahedron Letters 25(17): 1753-1756.

Starting Material 9

4'-Ethyloxycarbonyldimethylmethyloxyacetophenone

This compound was synthesized from 4'-hydroxyacetophenone and ethyl bromoisobutyrate according to general method 4 described earlier.

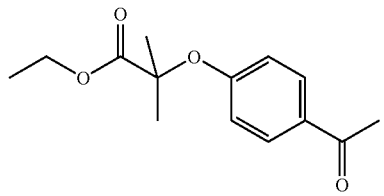

Purification was by silica gel chromatography (elution: cyclohexane/ethyl acetate 9:1).

1H NMR CDCl₃ ppm: 1.17 (t, J=5.64 Hz, 3H), 1.61 (s, 6H), 2.50 (s, 3H), 4.18 (q, J=5.64 Hz, 2H), 6.78 (d, J=8.82 Hz, 2H), 7.83 (d, J=8.81 Hz, 2H).

Starting Material 10

3-bromophenyl acetate

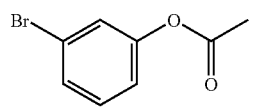

3-bromophenol was dissolved in dichloromethane. Triethylamine (1 eq) and acetic anhydride (2 eq) were added and the mixture was stirred at room temperature for 5 hours. The solvent was eliminated by vacuum evaporation. The evaporation residue was taken up in dichloromethane then dried on magnesium sulfate. The solvent was eliminated by vacuum evaporation.

Purification was by silica gel chromatography (elution: cyclohexane/ethyl acetate 95:5).

1H NMR CDCl₃ δ ppm: 2.30 (s, 3H), 7.0-7.4 (m, 4H)

Starting Material 11

2'-hydroxy-4'-bromoacetophenone

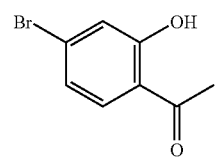

3-bromophenyl acetate (starting material 10) was mixed with aluminium chloride (3 eq), and the mixture was heated at 200° C. for 1 hour. The reaction medium was cooled to room temperature then poured in ice. The aqueous phase was extracted with methylene chloride which was dried on magnesium sulfate.

Purification was by silica gel chromatography (elution: cyclohexane/ethyl acetate 95:5).

1H NMR CDCl₃ δ ppm: 2.59 (s, 3H), 7.01 (d, J=8.5 Hz, 1H), 7.13 (s, 1H), 7.55 (d, J=8.5 Hz, 1H), 12.33 (s, 1H)

Starting Material 12

4'-Ethyloxycarbonyldimethylmethylthioacetochenone

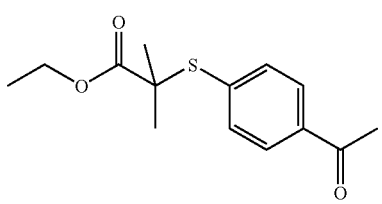

4'-methylthioacetophenone was dissolved in methylene chloride and the solution cooled to 0° C. Metachloroperbenzoic acid (1.5 eq) was added in small fractions. The reaction was followed by thin-layer chromatography. Additional metachloroperbenzoic acid was possibly added so as to obtain total disappearance of the starting product. The precipitate was eliminated by filtration. Calcium hydroxide (1.5 eq) was added and the mixture was stirred for another 15 min. The solid was eliminated by filtration, the filtrate dried on magnesium sulfate and the methylene chloride was then eliminated by vacuum evaporation.

The evaporation residue was taken up in acetic anhydride, then heated under reflux for 30 min and evaporated to dryness. The residue was taken up in methanol/triethylamine solution, stirred at room temperature for 15 minutes, then the solvents were eliminated by vacuum evaporation. The oily residue was taken up in a saturated aqueous ammonium chloride solution then extracted with methylene chloride. The organic phase was dried on magnesium sulfate then vacuum evaporated.

The resulting 4-mercaptoacetophenone intermediate was used without further purification. It was alkylated according to general method 4 to yield 4-ethyloxycarbonyldimethylm-ethylthioacetophenone. Purification was by silica gel chromatography (elution:cyclohexane/ethyl acetate 9:1).
Reference: Young N R, Gauthier J Y., Coombs w (1984). Tetrahedron Letters 25(17): 1753-1756.

1H NMR CDCl$_3$ δ ppm: 1.21 (t, J=7.32 Hz, 3H), 1.51 (s, 6H), 2.59 (s, 3H), 4.12 (q, J=7.32 Hz, 2H), 7.51 (d, J=8.40 Hz, 2H), 7.79 (d, J=8.40 Hz, 2H)

Synthesis of Intermediate Compounds Used to Synthesize the Inventive Compounds

Intermediate Compound 1

1-[4-chlorophenyl]-3-[3,5-dimethyl-4-hydroxyphenyl]prop-2-en-1-one

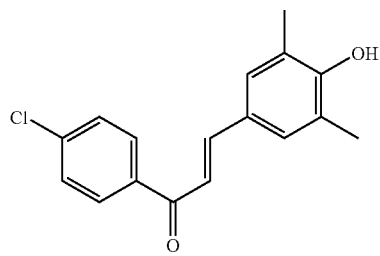

This compound was synthesized from 4-chloroacetophenone and 3,5-dimethyl-4-hydroxybenzaldehyde according to general method 1 described earlier.
Purification was by chromatography on silica gel (elution: cyclohexane/ethyl acetate 95:5).

1H NMR CDCl$_3$ δ ppm: 2.30 (s, 6H), 7.32 (s, 2H), 7.34 (d, J=15.25 Hz, 1H), 7.47 (d, J=8.86 Hz, 2H), 7.75 (d, J=15.26 Hz, 1H), 7.97 (d, J=8.86 Hz, 2H).

Intermediate Compound 2

1-[4-methylthiophenyl]-3-[3,5-dimethyl-4-hydroxyphenyl]prop-2-en-1-one

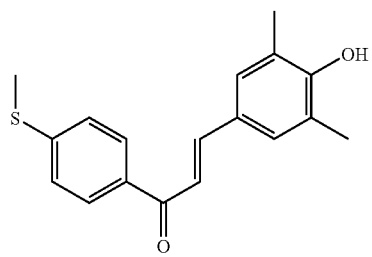

This compound was synthesized from 4'-methylthioacetophenone and 3,5-dimethyl-4-hydroxybenzaldehyde according to general method 1 described earlier.
Purification was by chromatography on silica gel (elution: cyclohexane/ethyl acetate 8:2).

1H NMR DMSO δ ppm: 2.22 (s, 6H), 2.54 (s, 3H), 7.36 (d, J=8.20 Hz, 2H), 7.48 (s, 2H), 7.62 (d, J=15.7 Hz, 1H), 7.74 (d, J=15.7 Hz, 1H), 8.10 (d, J=8.20 Hz, 2H), 8.92 (s, 1H)

Intermediate Compound 3

1-[2-methoxyphenyl]-3-[3,5-dimethyl-4-hydroxyphenyl]prop-2-en-1-one

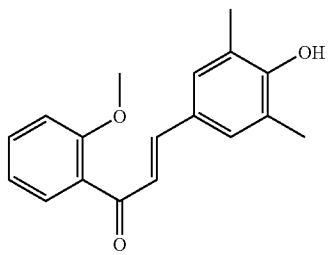

This compound was synthesized from 2'-methoxyacetophenone and 3,5-dimethyl-4-hydroxybenzaldehyde according to general method 1 described earlier.
Purification was by chromatography on silica gel (elution: cyclohexane/ethyl acetate 8:2).

1H NMR DMSO δ ppm: 2.39 (s, 6H), 2.22 (s, 6H), 7.58 (s, 2H), 7.67-7.62 (m, 3H), 7.82 (d, J=15.5 Hz, 1H), 8.17 (d, 1H), 12.96 (s, 1H)

Intermediate Compound 4

1-[4-hexyloxyphenyl]-3-[3,5-dimethyl-4-hydroxphenyl]prop-2-en-1-one

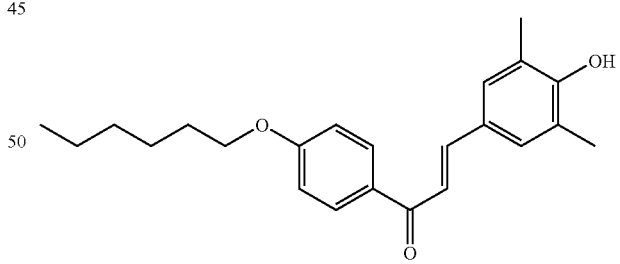

This compound was synthesized from 4-hexyloxyacetophenone and 3,5-dimethyl-4-hydroxybenzaldehyde according to general method 1 described earlier.
The expected compound was precipitated in the reaction medium, dried then used without further purification for the following reaction.

1H NMR DMSO δ ppm: 0.88 (m, 3H), 1.28-1.43 (m, 6H), 1.72 (m, 2H), 2.21 (s, 6H), 4.05 (t, J=6.42 Hz, 2H), 7.40 (d, J=8.43 Hz, 2H), 7.48 (s, 2H), 7.57 (d, J=15.24 Hz, 1H), 7.72 (d, J=15.24 Hz, 1H), 8.12 (d, J=8.43 Hz, 2H), 8.89 (s, 1H)

Intermediate Compound 5

1-[2-hydroxy-4-chlorophenyl]-3-[3,5-dimethyl-4-hydroxyphenyl]prop-2-en-1-one

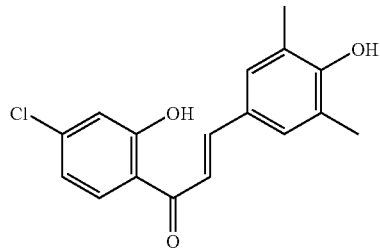

This compound was synthesized from 4'-chloro-2'-hydroxyacetophenone (starting material 3) and 3,5-dimethyl-4-hydroxybenzaldehyde according to general method 1 described earlier.

Purification was by chromatography on silica gel (toluene: 10).

1H NMR DMSO δppm: 2.21 (s, 6H), 7.1 (m, 2H), 7.55 (s, 2H), 7.72 (d, J=15.4 Hz, 1H), 7.80 (d, J=15.4 Hz, 1H), 8.25 (d, J=9.0 Hz, 1H), 9.09 (s, 1H), 13.04 (s, 1H)

Intermediate Compound 6

2-(3,5-dimethyl-4-hydroxyphenyl)-7-chloro-4H-1-benzopyran-4-one

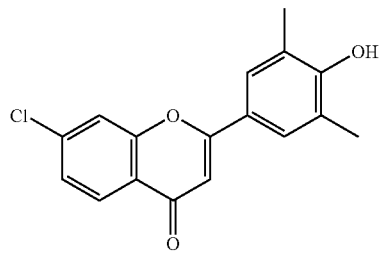

This compound was synthesized from 1-[2-hydroxy-4-chlorophenyl]-3-[3,5-dimethyl-4-hydroxyphenyl]prop-2-en-1-one (intermediate compound 5) according to the following method:

1-[2-hydroxy-4-chlorophenyl]-3-[3,5-dimethyl-4-hydroxyphenyl]prop-2-en-1-one was dissolved in dimethylsulfoxide, an iodine crystal was added, and the mixture was kept under reflux for 10 min.

The reaction medium was brought to room temperature, hydrolyzed. The precipitate was dried, rinsed with sodium thiosulfate solution then with water.

Purification was by dissolution in methylene chloride and precipitation by addition of heptane.

1H NMR DMSO δ ppm: 2.25 (s, 6H), 6.87 (s, 1H), 7.51 (d, J=8.55 Hz, 1H), 7.73 (s, 2H), 7.98 (m, 2H)

Reference: Doshi A G, S. P., Ghiya B J (1986). Indian J Chem Sect B 25: 759.

Intermediate Compound 7

1-[2-methyloxy-4-chlorophenyl]-3-[3,5-dimethyl-4-hydroxydimethylmethyloxyphenyl]prop-2-en-1-one

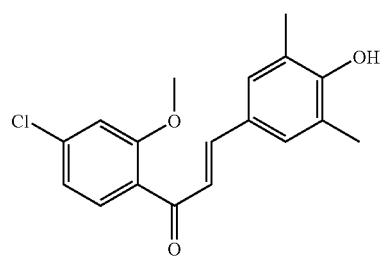

This compound was synthesized from 4'-chloro-2'-methoxyacetophenone and 3,5-dimethyl-4-hydroxybenzaldehyde according to general method 1 described earlier.

Purification was by chromatography on silica gel (elution: cyclohexane/ethyl acetate 85:15).

1H NMR DMSO δ ppm: 2.21 (s, 6H), 3.90 (s, 3H), 7.12 (m, 1H), 7.23 (d, J=15.5 Hz, 1H), 7.29 (s, J=1.80 Hz, 1H), 7.38 (d, J=15.5 Hz, 1H), 7.41 (s, 2H), 7.48 (d, J=7.98 Hz, 1H)

Intermediate Compound 8

1-[4-bromophenyl]-3-[3,5-dimethyl-4-hydroxyphenyl]prop-2-en-1-one

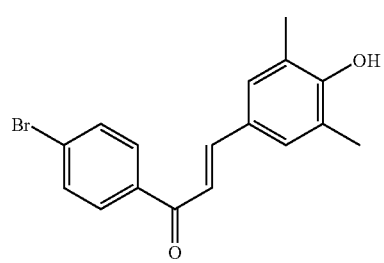

This compound was synthesized from 4'-bromoacetophenone and 3,5-dimethyl-4-hydroxybenzaldehyde according to general method 1 described earlier.

Purification was by chromatography on silica gel (elution: cyclohexane/ethyl acetate 85:15).

1H NMR DMSO δ ppm: 2.30 (s, 6H), 7.32 (s, 2H), 7.56-7.66 (m, 3H), 7.75 (d, J=15.27 Hz, 1H), 7.90 (d, J=8.70 Hz, 2H), 9.82 (s, 1H)

Intermediate Compound 9

1-[4-heptylphenyl]-3-[3,5-dimethyl-4-hydroxyphenyl]prop-2-en-1-one

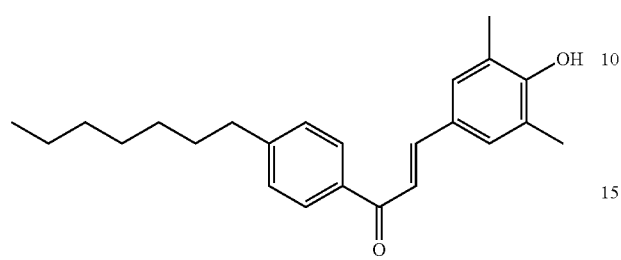

This compound was synthesized from 4'-heptylacetophenone and 3,5-dimethyl-4-hydroxybenzaldehyde according to general method 1 described earlier.

Purification was by chromatography on silica gel (elution: cyclohexane/ethyl acetate 85:15).

1H NMR DMSO δ ppm: 0.84 (m, 3H), 1.25 (m, 8H), 1.60 (m, 2H), 2.21 (s, 6H), 2.65 (t, J=7.50 Hz, 2H), 7.35 (d, J=8.02 Hz, 2H), 7.48 (s, 2H), 7.60 (d, J=15.48 Hz, 1H), 7.71 (d, J=15.48 Hz, 1H), 8.05 (d, J=8.02 Hz, 2H), 8.92 (s, 1H)

Synthesis of the Inventive Compounds

Compound 1

1-[2-hydroxy-4-ethoxycarbonyldimethylmethyloxyphenyl]-3-[3,5-ditertbutyl-4-hydroxyphenyl]prop-2-en-1-one

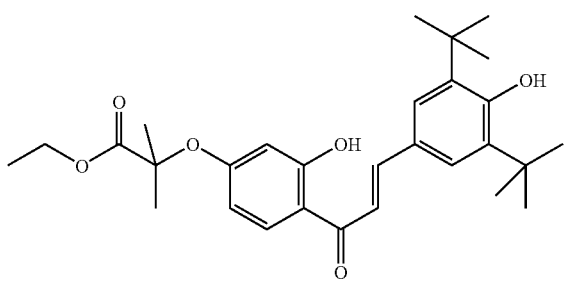

This compound was synthesized from 2'-hydroxy-4'-(ethoxycarbonyldimethylmethoxy)acetophenone (starting material 1) and 3,5-ditertbutyl-4-hydroxybenzaldehyde according to general method 1 described earlier.

Purification was by chromatography on silica gel (elution: cyclohexane/ethyl acetate 9:1).

1H NMR CDCl$_3$ δ ppm: 1.25 (t, J=7.11 Hz, 3H), 1.45 (s, 18H), 1.70 (s, 6H), 4.26 (q, J=7.11 Hz, 2H), 5.63 (s, 1H), 6.33 (d, J=2.37 Hz, 1H), 6.42 (dd, J=8.8 Hz, J=2.37 Hz, 1H), 7.41 (d, J=15.39 Hz, 1H), 7.5 (s, 2H), 7.83 (d, J=8.8 Hz, 1H), 7.88 (J=15.39 Hz, 1H), 13.5 (s, 1H)

Compound 2

1-[2-hydroxy-4-carboxydimethylmethyloxyphenyl]-3-[3,5-ditertbutyl-3-hydroxyphenyl]prop-2-en-1-one

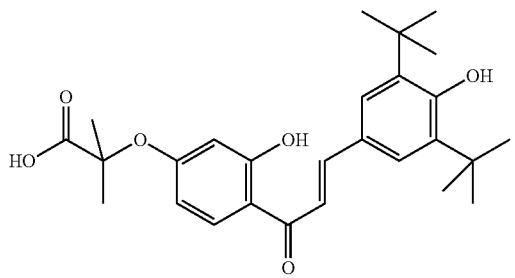

This compound was synthesized from 1-[2-hydroxy-4-ethoxycarbonyldimethylmethyloxyphenyl]-3-[3,5-ditertbutyl-4-hydroxyphenyl]prop-2-en-1-one (compound 1) according to the following method:

The ester was dissolved in ethanol, an aqueous 1N sodium hydroxide solution (5 eq) was added, and the mixture was kept under reflux for 10 hours. The medium was acidified by addition of 12 N hydrochloric acid then extracted with ethyl acetate. The organic phase was dried on magnesium sulfate then vacuum evaporated.

Purification was by preparative HPLC (reverse phase RP18, Licrospher 12 μm, elution:water-methanol-trifluoroacetic acid: 22:78:0.1).

1H NMR CDCl$_3$ δ ppm: 1.49 (s, 18H), 1.73 (s, 6H), 5.62 (s, 1H), 6.44 (d, J=15.5 Hz, 1H), 7.01 (m, 2H), 7.57 (t, 1H), 7.81 (d, J=15.5 Hz, 1H), 7.87 (d, 2H), 7.93 (d, 1H), 8.26 (d, 1H)

MS (ES-MS): 453.2 (M−1)

Compound 3

1-[2-hydroxy-4-chlorophenyl]-3-[4-carboxydimethylmethyloxyphenyl]prop-2-en-1-one

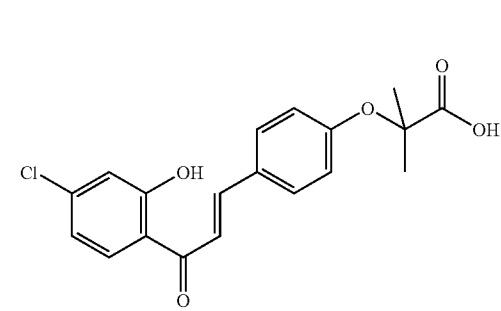

This compound was synthesized from 2'-hydroxy-4'-chloroacetophenone and 4-ethyloxycarbonyldimethylmethyloxybenzaldehyde (starting material 9) according to general method 2 described earlier.

Purification was by chromatography on silica gel (elution: cyclohexane/ethyl acetate 9:1).

1H NMR DMSO δ ppm: 1.58 (s, 6H), 6.87 (d, J=8.54 Hz, 2H), 7.05 (dd, J=8.54 Hz, 1.83 Hz, 1H), 7.09 (d, J=1.2 Hz, 1H), 7.90-7.80 (m, 4H), 8.25 (m, 8.52 Hz, 1H), 12.84 (s, 1H), 13.26 (s, 1H)

MS (ES-MS): 359.0 (M−1)

Compound 4

1-[2-hydroxyphenyl]-3-[4-carboxydimethylmethyloxyphenyl]prop-2-en-1-one

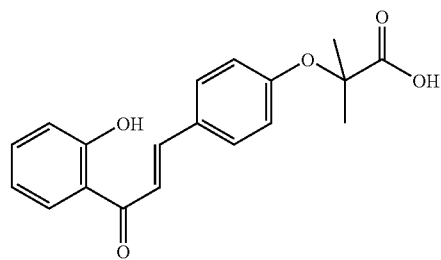

This compound was synthesized from 2'-hydroxyacetophenone and 4-ethyloxycarbonyldimethylmethyloxybenzaldehyde (starting material 4) according to general method 2 described earlier.

Purification was by chromatography on silica gel (elution: cyclohexane/ethyl acetate 9:1).

1H NMR DMSO δ ppm: 1.58 (s, 6H), 6.88 (d, 2H), 7.01 (m, 2H), 7.57 (t, 1H), 7.81 (d, J=15.5 Hz, 1H), 7.87 (d, 2H), 7.93 (d, J=15.5 Hz, 1H), 8.26 (d, 1H), 12.69 (s, 1H)

MS (ES-MS): 325.1 (M−1)

Compound 5

1-[2-hydroxyphenyl]-3-[3,5-dimethoxy-4-carboxydimethylmethyloxyphenyl]prop-2-en-1-one

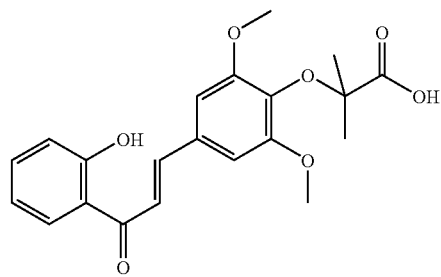

This compound was synthesized from 2'-hydroxyacetophenone and 3,5-dimethyloxy-4-ethyloxycarbonyldimethylmethyloxybenzaldehyde (starting material 5) according to general method 2 described earlier.

Purification was by chromatography on silica gel (elution: cyclohexane/ethyl acetate 9:1).

1H NMR DMSO δ ppm: 1.35 (s, 6H), 3.80 (s, 6H), 7.00-7.03 (m, 2H), 7.25 (s, 2H), 7.59 (t, 1H, J=8.07 Hz, 1H), 7.81 (d, J=15.5 Hz, 1H), 8.00 (d, J=15.5 Hz, 1H), 8.31 (d, J=8.07 Hz, 1H), 12.36 (s, 1H), 12.69 (s, 1H)

MS (ES-MS): 385.3 (M−1)

Compound 6

1-[2-hydroxy-4-chlorophenyl]-3-[3,5-dimethoxy-4-carboxydimethylmethyloxyphenyl]prop-2-en-1-one

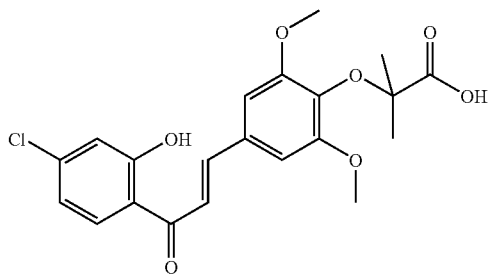

This compound was synthesized from 2'-hydroxy-4'-chloroacetophenone (starting material 3) and 3,5-dimethyloxy-4-ethyloxycarbonyldimethylmethyloxybenzaldehyde (starting material 5) according to general method 2 described earlier.

Purification was by chromatography on silica gel (elution: cyclohexane/ethyl acetate 9:1).

1H NMR DMSO δ ppm: 1.34 (s, 6H), 3.80 (s, 6H), 7.08 (dd, J=1.77 Hz, 1H), 7.12 (d, J=1.77 Hz, 1H), 7.24 (s, 2H), 7.79 (d, J=15.4 Hz, 1H), 7.93 (d, J=15.4 Hz, 1H), 8.27 (d, J=8.3 Hz, 1H), 12.36 (s, 1H), 12.69 (s, 1H)

MS (ES-MS): 419.0 (M−1)

Compound 7

1-[2-hydroxy-4-chlorophenyl]-3-[3,5-dimethyl-4-carboxydimethyl methyloxyphenyl]prop-2-en-1-one

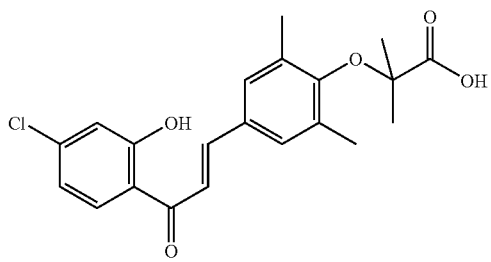

This compound was synthesized from 2'-hydroxy-4'-chloroacetophenone (starting material 3) and 3,5-dimethyl-4-ethyloxycarbonyldimethylmethyloxybenzaldehyde (starting material 6) according to general method 2 described earlier.

Purification was by chromatography on silica gel (elution: cyclohexane/ethyl acetate 9:1).

1H NMR DMSO δ ppm: 1.39 (s, 6H), 2.22 (s, 6H), 7.07 (m, 1H), 7.12 (d, J=2.07 Hz, 1H), 7.61 (s, 2H), 7.74 (d, J=15.5 Hz, 1H), 7.87 (d, J=15.5 Hz, 1H), 8.26 (d, 1H), 12.76 (s, 1H)

MS (ES-MS): 387.1 (M−1)

Compound 8

1-[2-hydroxy-4-carboxydimethylmethyloxyphenyl]-
3-[3,5-dibromo-4-hydroxyphenyl]prop-2-en-1-one

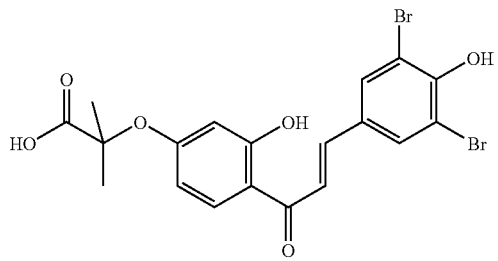

This compound was synthesized from 2'-hydroxy-4'-ethyl oxycarbonyldimethylmethyloxyacetophenone (starting material 1) and 3,5-dibromo-4-hydroxybenzaldehyde according to general method 2 described earlier.

Purification was by chromatography on silica gel (elution: cyclohexane/ethyl acetate 9:1).

1H NMR CDCl$_3$ δ ppm: 1.60 (s, 6H), 6.24 (d, J=2.47 Hz, 1H), 6.43 (dd, J=2.47 Hz, J=8.52 Hz, 1H), 7.70 (d, J=15.5 Hz, 1H), 7.96 (d, J=15.5 Hz, 1H), 8.22 (s, 2H), 8.34 (d, J=9.16 Hz, 1H), 13.34 (s, 1H)

MS (ES-MS): 498.6 (M−1)

Compound 9

1-[2-hydroxyphenyl]-3-[3-carboxydimethylmethyloxyphenyl]prop-2-en-1-one

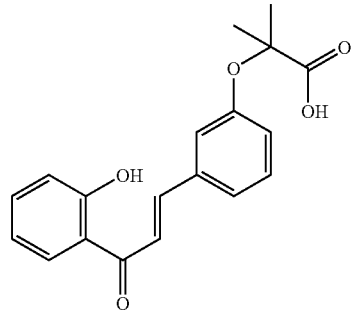

This compound was synthesized from 2'-hydroxyacetophenone and 3-ethyloxycarbonyldimethylmethyloxybenzaldehyde (starting material 7) according to general method 2 described earlier.

Purification was by chromatography on silica gel (elution: cyclohexane/ethyl acetate 9:1).

1H NMR DMSO δ ppm: 1.56 (s, 6H), 6.91 (dd, J=8.01 Hz, J=2.47 Hz, 1H), 7.03-6.99 (m, 2H), 7.41-7.36 (m, 2H), 7.60-7.52 (m, 2H), 7.77 (d, J=15.5 Hz, 1H), 13.17 (s, 1H)

MS (ES-MS): 325.8 (M−1)

Compound 10

1-[2-hydroxy-4-carboxydimethylmethyloxyphenyl]-
3-[3-hydroxyphenyl]prop-2-en-1-one

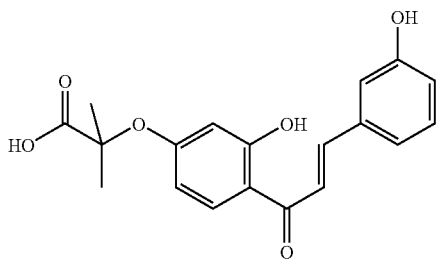

This compound was synthesized from 2'-hydroxy-4'-ethyloxycarbonyl dimethylmethyloxyacetophenone (starting material 1) and 3-hydroxybenzaldehyde according to general method 2 described earlier.

Purification was by chromatography on silica gel (elution: cyclohexane/ethyl acetate 9:1).

1H NMR DMSO δ ppm: 1.60 (s, 6H), 6.25 (d, J=2.47 Hz, 1H), 6.43 (dd, J=2.47 Hz, 9.09 Hz, 1H), 6.89 (m, 1H), 7.35-7.24 (m, 3H), 7.73 (d, 1H), 7.92 (d, J=15.5 Hz, 1H), 8.27 (d, J=15.5 Hz, 1H), 13.21 (s, 1H), 13.39 (s, 1H).

MS (ES-MS): 341 (M−1)

Compound 11

1-[2-hydroxyphenyl]-3-[3,5-dimethyl-4-carboxydimethylmethyloxyphenyl]prop-2-en-1-one

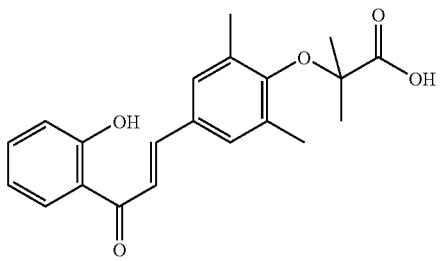

This compound was synthesized from 2'-hydroxyacetophenone and 3,5-dimethyl-4-ethyloxycarbonyldimethylmethyloxybenzaldehyde (starting material 6) according to general method 2 described earlier.

Purification was by chromatography on silica gel (elution: cyclohexane/ethyl acetate 9:1) followed by preparative HPLC (reverse phase RP18, Licrospher 12 μm, elution:water-methanol-trifluoroacetic acid: 22:78:0.1).

1H NMR DMSO δ ppm: 1.57 (s, 6H), 2.31 (s, 6H), 6.96 (t, J=8.17 Hz, 1H), 7.04 (d, J=8.72 Hz, 1H), 7.35 (s, 2H), 7.49 (t, J=8.2 Hz, 1H), 7.58 (d, J=15.8 Hz, 1H), 7.84 (d, J=15.8 Hz, 1H), 7.94 (d, J=8.7 Hz, 1H), 12.87 (s, 1H)

MS (ES-MS): 353.1 (M−1)

Compound 12

1-[2-hydroxy-4-carboxydimethylmethyloxyphenyl]-3-[4-methylthiophenyl]prop-2-en-1-one

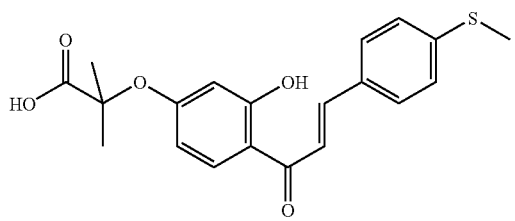

This compound was synthesized from 2'-hydroxy-4'-ethyloxycarbonyldimethylmethyloxyacetophenone (starting material 1) and 4-methylthiobenzaldehyde according to general method 2 described earlier.

Purification was by chromatography on silica gel (elution: cyclohexane/ethyl acetate 9:1) followed by preparative HPLC (reverse phase RP18, Licrospher 12 μm, elution:water-methanol-trifluoroacetic acid: 22:78:0.3).

1H NMR DMSO δ ppm: 1.60 (s, 6H), 2.54 (s, 3H), 6.25 (d, 1H), 6.43 (dd, J=2.47 Hz, 1H), 7.33 (d, J=8.56 Hz, 2H), 7.8 (d, 15.5 Hz, 1H), 7.86 (d, J=8.56 Hz, 2H), 7.98 (d, J=15.5 Hz, 1H), 8.29 (d, J=9.1 Hz, 1H), 13.34 (s, 1H)

MS (ES-MS): 373.1 (M−1)

Compound 13

1-[2,4-dihydroxyphenyl]-3-[4-carboxydimethylmethyloxyphenyl]prop-2-en-1-one

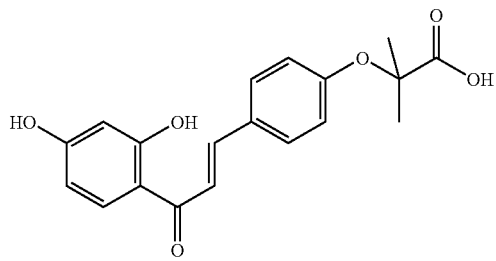

This compound was synthesized from 2',4'-dihydroxyacetophenone and 4-ethoxycarbonyldimethylmethyloxybenzaldehyde (starting material 4) according to general method 2 described earlier.

Purification was by chromatography on silica gel (elution: cyclohexane/ethyl acetate 9:1) followed by preparative HPLC (reverse phase RP18, Licrospher 12 μm, elution: water-methanol-trifluoroacetic acid: 34:66:0.1).

1H NMR DMSO δ ppm: 1.57 (s, 6H), 6.29 (d, J=2.16 Hz, 1H), 6.41 (dd, J=9.18 Hz, J=2.16 Hz, 1H), 6.86 (d, J=8.64 Hz, 2H), 7.75 (d, J=15.67 Hz, 1H), 7.83-7.88 (m, 3H), 8.19 (d, J=9.18 Hz, 1H), 10.74 (s, 1H), 13.53 (s, 1H)

MS (maldi-Tof): 343.1 (M+1)

Compound 14

1-[2-hydroxyphenyl]-3-[4-carboxydimethylmethyloxyphenyl]prop-2-en-1-one

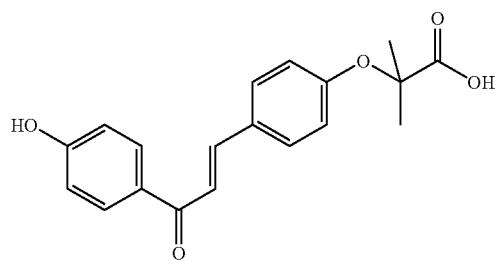

This compound was synthesized from 4'-hydroxyacetophenone and 4-ethoxycarbonyldimethylmethyloxybenzaldehyde (starting material 4) according to general method 2 described earlier.

Purification was by chromatography on silica gel (elution: cyclohexane/ethyl acetate 9:1) followed by preparative HPLC (reverse phase RP18, Licrospher 12 μm, elution:water-methanol-trifluoroacetic acid: 34:66:0.1).

1H NMR DMSO δ ppm: 1.56 (s, 6H), 6.85 (d, J=8.63 Hz, 2H), 6.90 (d, J=9.21 Hz, 2H), 7.63 (d, J=15.54 Hz, 1H), 7.78 (m, 3H), 8.05 (d, J=8.61 Hz, 2H), 10.40 (s, 1H), 13.22 (s, 1H)

MS (maldi-Tof): 327.1 (M+1)

Compound 15

1-[4-chlorophenyl]-3-[3,5-dimethyl-4-isopropyloxycarbonyldimethylmethyloxyphenyl]prop-2-en-1-one

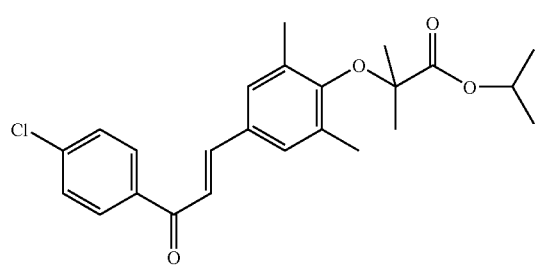

This compound was synthesized from 1-[4-chlorophenyl]-3-[3,5-dimethyl-4-hydroxyphenyl]prop-2-en-1-one (intermediate compound 1) and isopropyl bromoisobutyrate according to general method 4 described earlier.

Purification was by chromatography on silica gel (elution: cyclohexane/ethyl acetate 9:1).

1H NMR DMSO δ ppm: 1.25 (d, J=6.06 Hz, 6H), 1.39 (s, 6H), 5.00 (sept, J=6.06 Hz, 1H), 7.57 (s, 2H), 7.62 (d, J=8.40 Hz, 2H), 7.64 (d, J=15.8 Hz, 1H), 7.81 (d, J=15.8 Hz, 1H), 8.16 (d, J=8.40 Hz, 2H).

MS (Maldi-Tof): 415.1 (M+1)

Compound 16

1-[4-chlorophenyl]-3-[3,5-dimethyl-4-tertbutyloxy-carbonyldimethylmethyloxyphenyl]prop-2-en-1-one

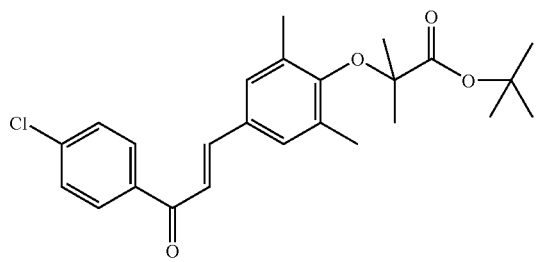

This compound was synthesized from 1-[4-chlorophenyl]-3-[3,5-dimethyl-4-hydroxyphenyl]prop-2-en-1-one (intermediate compound 1) and tertbutyl bromoisobutyrate according to general method 4 described earlier.

Purification was by chromatography on silica gel (elution: cyclohexane/ethyl acetate 9:1).

Compound 17

1-[4-chlorophenyl]-3-[3,5-dimethyl-4-carboxydimethylmethyloxyphenyl]prop-2-en-1-one

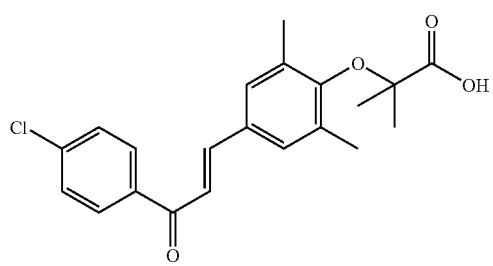

This compound was synthesized from 1-[4-chlorophenyl]-3-[3,5-dimethyl-4-tertbutyloxycarbonyldimethyl-methyloxyphenyl]prop-2-en-1-one (compound 16) according to general method 5 described earlier.

Purification was by chromatography on silica gel (elution: dichloromethane/methanol 98:2)

1H NMR DMSO δ ppm: 1.39 (s, 6H), 2.22 (s, 6H), 7.58 (s, 2H), 7.67-7.62 (m, 3H), 7.82 (d, J=15.5 Hz, 1H), 8.17 (d, 1H), 12.96 (s, 1H)

MS (Maldi-Tof): 373.3 (M+1)

Compound 18

1-[2-hydroxy-4-carboxydimethylmethyloxyphenyl]-3-[4-chlorophenyl]prop-2-en-1-one

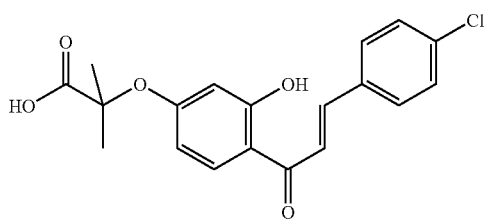

This compound was synthesized from 2'-hydroxy-4'-ethyloxycarbonyldimethylmethyloxyacetophenone (starting material 1) and 4-chlorobenzaldehyde according to general method 2 described earlier.

Purification was by chromatography on silica gel (elution: cyclohexane/ethyl acetate 9:1) followed by preparative HPLC (reverse phase RP18, Licrospher 12 μm, elution:water-methanol-trifluoroacetic acid: 22:78:0.1).

1H NMR DMSO δ ppm: 1.60 (s, 6H), 6.25 (d, J=2.47 Hz, 1H), 6.45 (dd, J=2.47 Hz, J=9.12 Hz, 1H), 6.55 (d, J=8.55 Hz, 2H), 7.82 (d, J=15.54 Hz, 1H), 7.97 (d, J=8.55 Hz, 2H), 8.03 (d, J=15.54 Hz, 1H), 8.29 (d, J=9.12 Hz, 1H), 13.20 (s, 1H), 13.39 (s, 1H)

MS (ES-MS): 359.0 (M−1)

Compound 19

1-[2-hydroxyphenyl]-3-[4-carboxydimethylmethyl thiophenyl]prop-2-en-1-one

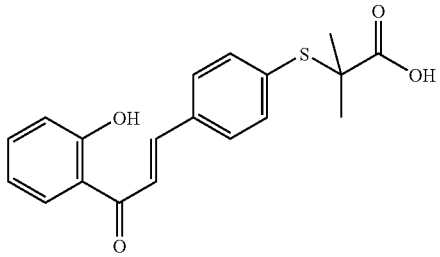

This compound was synthesized from 2'-hydroxyacetophenone and ethyloxycarbonyldimethylmethylthiobenzaldehyde (starting material 8) according to general method 2 described earlier.

Purification was by chromatography on silica gel (elution: dichloromethane/methanol 95:5) followed by preparative HPLC (reverse phase RP18, Licrospher 12 μm, elution:water-methanol-trifluoroacetic acid: 22:78:0.1).

1H NMR DMSO δ ppm: 1.44 (s, 6H), 6.99-7.05 (m, 1H), 7.52 (d, J=8.1 Hz, 2H), 7.58 (m, 1H), 7.83 (d, J=15.5 Hz, 1H), 7.92 (d, J=8.1 Hz, 2H), 8.09 (d, J=15.5 Hz, 1H), 8.26 (dd, J=1.62, J=8.6 Hz, 1H), 12.47 (s, 1H), 12.78 (s, 1H)

MS (Maldi-Tof): 242.9 (M+1)

Compound 20

1-[4-chloro-2-hydroxyphenyl]-3-[4-carboxydimethylmethylthiophenyl]prop-2-en-1-one

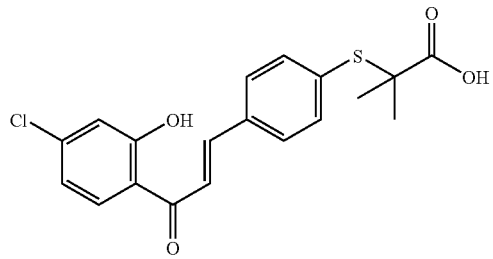

This compound was synthesized from 4'-chloro-2'-hydroxyacetophenone (starting material 3) and 4-ethyloxycarbonyldimethylmethylthiobenzaldehyde (starting material 8) according to general method 2 described earlier.

Purification was by chromatography on silica gel (elution: dichloromethane/methanol 95:5) followed by preparative HPLC (reverse phase RP18, Licrospher 12 μm, elution:water-methanol-trifluoroacetic acid: 22:78:0.1).

1H NMR DMSO δ ppm: 1.43 (s, 6H), 7.05 (dd, J=1.7 Hz, J=8.46 Hz, 1H), 7.11 (d, J=2.25 Hz, 1H), 7.51 (d, J=7.92 Hz, 2H), 7.82 (d, J=15.8 Hz, 1H), 7.89 (d, J=7.9 Hz, 2H), 8.05 (d, J=15.2 Hz, 1H), 8.23 (d, J=8.46 Hz, 1H), 12.57 (s, 1H), 12.78 (s, 1H).

MS (Maldi-Tof): 377.0 (M−1)

Compound 21

1-[4-carboxydimethylmethyloxyphenyl]-3-[3,5-dimethyl-4-hydroxyphenyl]prop-2-en-1-one

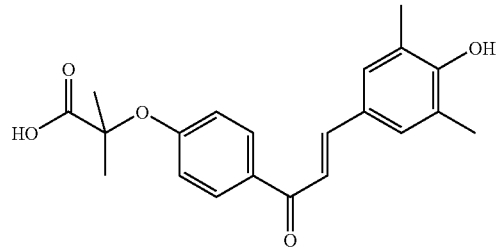

This compound was synthesized from 4-ethyloxycarbonyldimethylmethyloxy acetophenone (starting material 9) and 3,5-dimethyl-4-hydroxybenzaldehyde according to general method 2 described earlier.

Purification was by chromatography on silica gel (elution: dichloromethane/methanol 95:5) followed by preparative HPLC (reverse phase RP18, Licrospher 12 μm, elution:water-methanol-trifluoroacetic acid 22:78:0.1).

1H NMR DMSO δ ppm: 1.60 (s, 6H), 2.21 (s, 6H), 6.91 (d, J=9.09 Hz, 2H), 7.48 (s, 2H), 7.57 (d, J=15.12 Hz, 1H), 7.70 (d, J=15.63 Hz, 1H), 8.09 (d, J=9.06 Hz, 2H), 8.9 (s, 1H), 13.29 (s, 1H)

MS (Maldi-Tof): 355.2 (M+1)

Compound 22

1-[4-methylthiophenyl]-3-[4-carboxydimethylmethyloxyphenyl]prop-2-en-1-one

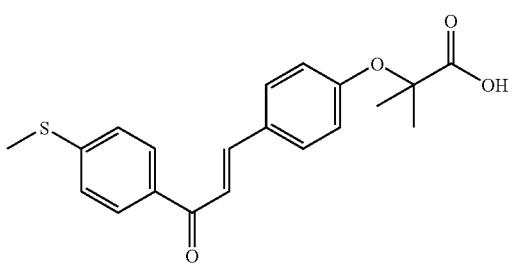

This compound was synthesized from 4'-methylthioacetophenone (starting material 12) and 4-ethyloxycarbonyldimethylmethyloxybenzaldehyde (starting material 9) according to general method 2 described earlier.

Purification was by chromatography on silica gel (elution: dichloromethane/methanol 95:5) followed by preparative HPLC (reverse phase RP18, Licrospher 12 μm, elution:water-methanol-trifluoroacetic acid 22:78:0.1).

1H NMR DMSO δ ppm: 1.57 (s, 6H), 2.57 (s, 3H), 6.86 (d, J=8.94 Hz, 2H), 7.41 (d, J=8.40 Hz, 2H), 7.69 (d, J=15.2 Hz, 1H), 7.84-7.78 (m, 3H), 8.09 (d, J=8.4 Hz, 2H), 13.21 (s, 1H)

MS (Maldi-Tof): 357.2 (M−1)

Compound 23

1-[4-carboxydimethylmethyloxyphenyl]-3-[4-chlorophenyl]prop-2-en-1-one

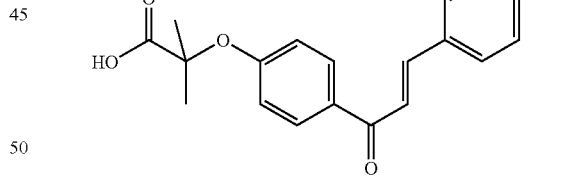

This compound was synthesized from 4-ethyloxycarbonyl dimethylmethyloxyacetophenone (starting material 9) and 4-chlorobenzaldehyde according to general method 3 described earlier.

Purification was by chromatography on silica gel (elution: dichloromethane/methanol 95:5) followed by preparative HPLC (reverse phase RP18, Licrospher 12 μm, elution:water-methanol-trifluoroacetic acid 22:78:0.1).

1H NMR DMSO δ ppm: 1.72 (s, 6H), 6.97 (d, J=8.61 Hz, 2H), 7.39 (d, J=8.25 Hz, 2H), 7.50 (d, J=15.72 Hz, 1H), 7.57 (d, J=8.61 Hz, 2H), 7.77 (d, J=15.72 Hz, 1H), 7.99 (d, J=8.61 Hz, 2H), 13.30 (s, 1H)

MS (Maldi-Tof): 345.1 (M+1)

Compound 24

1-[4-carboxydimethylmethylthiophenyl]-3-[4-methylthiophenyl]prop-2-en-1-one

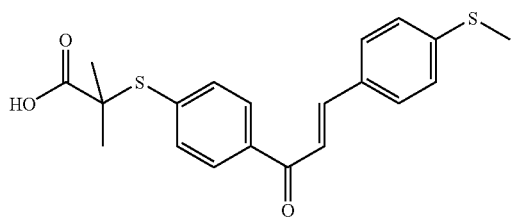

This compound was synthesized from 4-ethyloxycarbonyl dimethylmethylthioacetophenone (starting material 12) and 4-methylthiobenzaldehyde according to general method 3 described earlier.

Purification was by chromatography on silica gel (elution: dichloromethane/methanol 95:5) followed by preparative HPLC (reverse phase RP18, Licrospher 12 µm, elution:water-methanol-trifluoroacetic acid 22:78:0.1).

1H NMR DMSO δ ppm: 1.46 (s, 6H), 2.54 (s, 3H), 7.33 (d, J=8.61 Hz, 2H), 7.59 (d, J=8.10 Hz, 2H), 7.73 (d, J=15.66 Hz, 1H), 7.85 (d, J=8.10 Hz, 2H), 7.92 (d, J=15.66 Hz, 1H), 8.13 (d, 8.10 Hz, 2H), 12.85 (s, 1H)

MS (Maldi-Tof): 373.1 (M+1)

Compound 25

1-[2-hydroxy-4-bromophenyl]-3-[3,5-dimethyl-4-carboxydimethylmethyloxyphenyl]prop-2-en-1-one

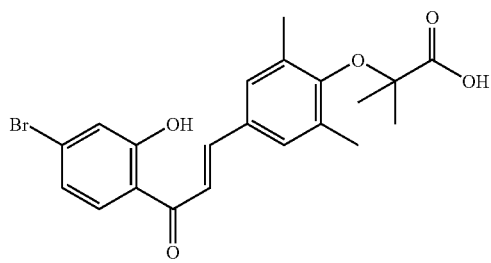

This compound was synthesized from 4'-bromo-2'-hydroxyacetophenone (starting material 11) and 3,5-dimethyl-4-ethyloxycarbonyldimethyloxybenzaldehyde (starting material 6) according to general method 2 described earlier.

Purification was by chromatography on silica gel (elution: dichloromethane/methanol 95:5) followed by preparative HPLC (reverse phase RP18, Licrospher 12 µm, elution:water-methanol-trifluoroacetic acid 22:78:0.1).

1H NMR DMSO δ ppm: 1.39 (s, 6H), 2.22 (s, 6H), 7.20 (dd, J=2.16, J=8.55 Hz, 1H), 7.25 (d, J=1.59 Hz, 1H), 7.60 (s, 2H), 7.73 (d, J=15.51 Hz, 1H), 7.86 (d, J=15.51 Hz, 1H), 8.16 (d, J=8.58 Hz, 1H), 12.70 (s, 1H), 13.30 (s, 1H)

MS (ES-MS): 432.9 (M−1)

Compound 26

1-[4-carboxydimethylmethyloxyphenyl]-3-[4-methylthiohenyl]prop-2-en-1-one

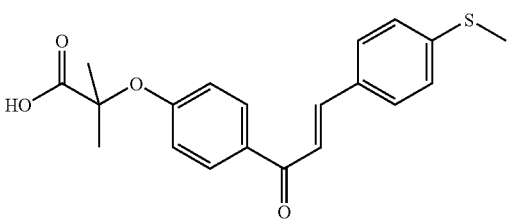

This compound was synthesized from 4'-ethyloxycarbonyldimethylmethyloxyacetophenone (starting material 9) and 4-methylthiobenzaldehyde according to general method 2 described earlier.

Purification was by chromatography on silica gel (elution: dichloromethane/methanol 95:5) followed by preparative HPLC (reverse phase RP18, Licrospher 12 µm, elution:water-methanol-trifluoroacetic acid 22:78:0.1).

1H NMR DMSO δ ppm: 1.60 (s, 6H), 2.53 (s, 3H), 6.93 (d, J=9.00 Hz, 2H), 7.32 (d, J=8.49 Hz, 2H), 7.68 (d, J=15.51 Hz, 1H), 7.82 (d, J=8.52 Hz, 2H), 7.89 (d, J=15.51 Hz, 1H), 8.13 (d, 9.00 Hz, 2H), 13.30 (s, 1H)

MS (Maldi-Tof): 355.0 (M+1)

Compound 27

1-[4-methylthiophenyl]-3-[3,5-dimethyl-4-tertbutyloxycarbonyldimethylmethyloxyphenyl]prop-2-en-1-one

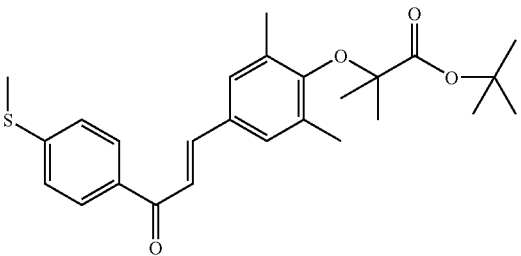

This compound was synthesized from 1-[4-methylthiophenyl]-3-[3,5-dimethyl-4-hydroxyphenyl]prop-2-en-1-one (intermediate compound 2) and tertbutyl bromoisobutyrate according to general method 4 described earlier.

Purification was by chromatography on silica gel (elution: cyclohexane/ethyl acetate 8:2).

Compound 28

1-[4-methylthiophenyl]-3-[3,5-dimethyl-4-isopropyloxycarbonyldimethylmethyloxyphenyl]prop-2-en-1-one

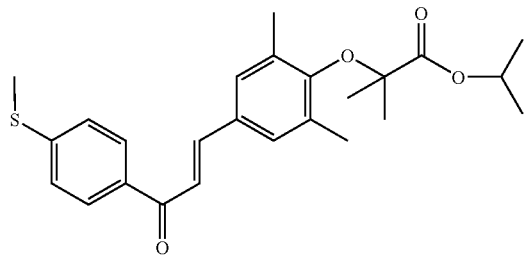

This compound was synthesized from 1-[4-methylthiophenyl]-3-[3,5-dimethyl-4-hydroxyphenyl]prop-2-en-1-one (intermediate compound 2) and isopropyl bromoisobutyrate according to general method 4 described earlier.

Purification was by chromatography on silica gel (elution: cyclohexane/ethyl acetate 9:1).

1H NMR DMSO δ ppm: 1.25 (d, J=6.18 Hz, 6H), 1.39 (s, 6H), 2.18 (s, 6H), 2.57 (s, 3H), 4.99 (sept, J=6.18 Hz, 1H), 7.40 (d, J=8.28 Hz, 2H), 7.58 (s, 2H), 7.62 (d, J=15.5 Hz, 1H), 7.82 (d, J=15.5 Hz, 1H), 8.10 (d, J=8.28 Hz, 2H), 12.97 (s, 1H)

MS (Maldi-Tof): 427.1 (M+1)

Compound 29

1-[4-methylthiophenyl]-3-[3,5-dimethyl-4-carboxydimethylmethyloxyphenyl]prop-2-en-1-one

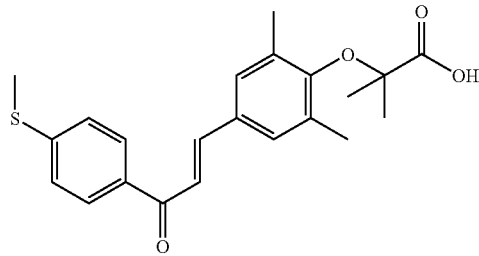

This compound was synthesized from 1-[4-methylthiophenyl]-3-[3,5-dimethyl-4-tertbutyloxycarbonyldimethylmethyloxyphenyl]prop-2-en-1-one (compound 28) according to general method 5 described earlier.

Purification was by chromatography on silica gel (elution: dichloromethane/methanol 98:2).

1H NMR DMSO δ ppm: 1.39 (s, 6H), 2.22 (s, 6H), 2.57 (s, 3H), 7.40 (d, J=8.55 Hz, 2H), 7.57 (s, 2H), 7.62 (d, J=15.5 Hz, 1H), 7.83 (d, J=15.5 Hz, 1H), 8.10 (d, J=8.55 Hz, 2H), 12.97 (s, 1H)

MS (ES-MS): 383.3 (M−1)

Compound 30

1-[2-methoxyphenyl]-3-[3,5-dimethyl-4-tertbutyloxycarbonyldimethylmethyloxyphenyl]prop-2-en-1-one

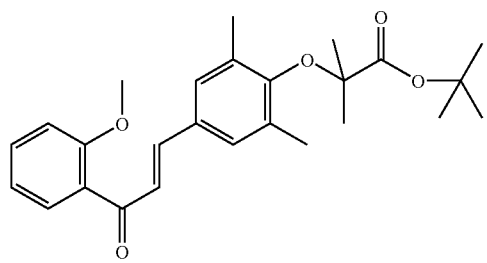

This compound was synthesized from 1-[2-methoxyphenyl]-3-[3,5-dimethyl-4-hydroxyphenyl]prop-2-en-1-one (intermediate compound 3) and tertbutyl bromoisobutyrate according to general method 4 described earlier.

Purification was by chromatography on silica gel (elution: cyclohexane/ethyl acetate 9:1).

Compound 31

1-[2-methoxyphenyl]-3-[3,5-dimethyl-4-carboxydimethylmethyloxyphenyl]prop-2-en-1-one

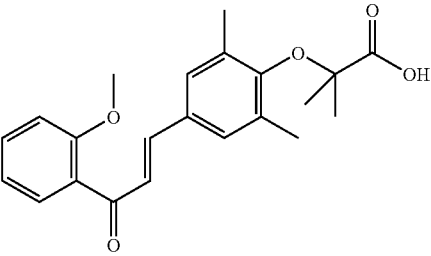

This compound was synthesized from 1-[2-methoxyphenyl]-3-[3,5-dimethyl-4-tertbutyloxycarbonyldimethylmethyloxyphenyl]prop-2-en-1-one (compound 30) according to general method 5 described earlier.

Purification was by chromatography on silica gel (elution: dichloromethane/methanol 98:2).

1H NMR DMSO δ ppm: 1.38 (s, 6H), 2.19 (s, 6H), 3.93 (s, 3H), 7.05 (m, 1H), 7.20 (d, J=8.31 Hz, 1H), 7.25 (d, J=15.5 Hz, 1H), 7.37 (d, J=15.5 Hz, 1H), 7.39 (s, 2H), 7.46 (d, J=7.2 Hz, 1H), 7.53 (m, 1H), 12.93 (s, 1H)

MS (ES-MS): 367.1 (M−1)

Compound 32

1-[4-hexyloxyphenyl]-3-[3,5-dimethyl-tertbutyloxy-carbonyldimethylmethyloxyphenyl]prop-2-en-1-one

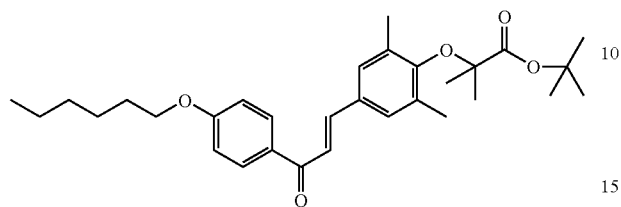

This compound was synthesized from 1-[4-hexyloxyphenyl]-3-[3,5-dimethyl-4-hydroxyphenyl]prop-2-en-1-one (intermediate compound 4) and tertbutyl bromoisobutyrate according to general method 4 described earlier.

Purification was by chromatography on silica gel (elution: cyclohexane/ethyl acetate 95:5)

Compound 33

1-[4-hexyloxyphenyl]-3-[3,5-dimethyl-4-carboxydimethylmethyloxyphenyl]prop-2-en-1-one

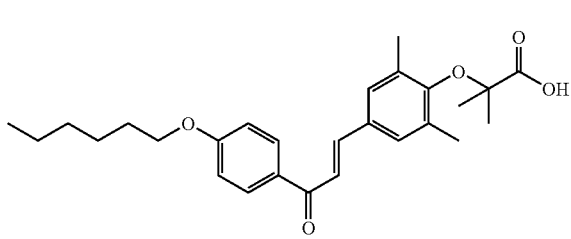

This compound was synthesized from 1-[4-hexyloxyphenyl]-3-[3,5-dimethyl-4-tertbutyloxycarbonyldimethylmethyloxyphenyl]prop-2-en-1-one (compound 32) according to general method 5 described earlier.

Purification was by recrystallization in methanol.

1H NMR DMSO δ ppm: 0.88 (t, J=6.33 Hz, 3H), 1.30 (m, 4H), 1.39 (s, 6H), 1.44 (m, 2H), 1.73 (m, 2H), 2.22 (s, 6H), 4.06 (t, J=6.30 Hz, 2H), 7.06 (d, J=8.61 Hz, 2H), 7.56 (s, 2H), 7.58 (d, J=15.5 Hz, 1H), 7.82 (d, J=15.5 Hz, 1H), 8.13 (d, J=6.61 Hz, 2H)

MS (ES-MS): 437.2 (M−1)

Compound 34

2-(3,5-dimethyl-4-tertbutyloxycarbonyldimethyl-methyloxyphenyl)-7-chloro-4H-1-benzopyran-4-one

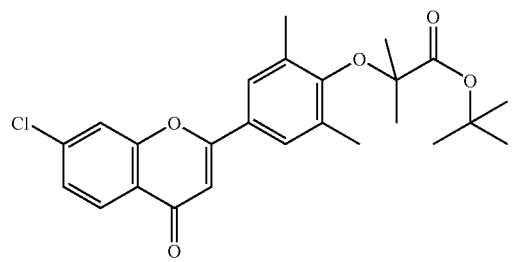

This compound was synthesized from 2-(3,5-dimethyl-4-hydroxyphenyl)-7-chloro-4H-1-benzopyran-4-one (intermediate compound 6) and tertbutyl bromoisobutyrate according to general method 4 described earlier. Purification was by precipitation in the solvent mixture dichloromethane/heptane.

Compound 35

2-(3,5-dimethyl-carboxydimethylmethyloxyphenyl)-7-chloro-4H-1-benzopyran-4-one

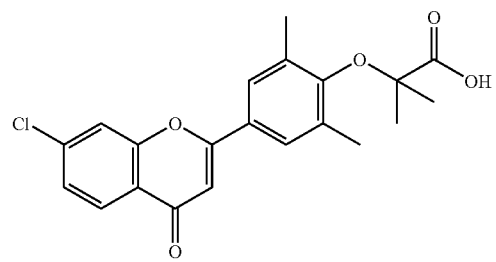

This compound was synthesized from 2-(3,5-dimethyl-4-tertbutyloxycarbonyldimethylmethyloxyphenyl)-7-chloro-4H-1-benzopyran-4-one (compound 34) according to general method 5 described earlier.

Purification was by preparative HPLC (reverse phase RP18, Licrospher 12 μm, elution:water-methanol-trifluoroacetic acid: 22:78:0.1).

1H NMR DMSO δ ppm: 1.24 (s, 6H), 2.28 (s, 6H), 7.02 (s, 1H), 7.56 (dd, J=8.71 Hz, J=1.75 Hz, 1H), 7.85 (s, 2H), 8.03 (d, J=1.75 Hz, 1H), 8.06 (d, 8.71 Hz, 1H)

MS (Maldi-Tof): 387.1 (M+1)

Compound 36

1-[2-methyloxy-4-chlorophenyl]-3-[3,5-dimethyl-4-tertbutyloxycarbonyldimethylmethyloxyphenyl]prop-2-en-1-one

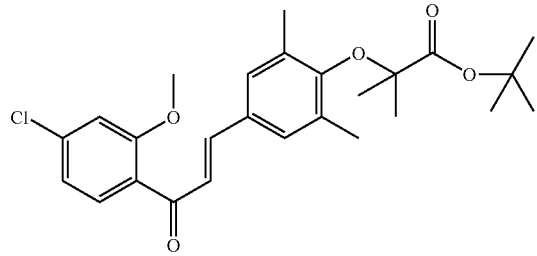

This compound was synthesized from 1-[2-methyloxy-4-chlorophenyl]-3-[3,5-dimethyl-4-hydroxydimethylmethyloxyphenyl]prop-2-en-1-one (intermediate compound 7) and tertbutyl bromoisobutyrate according to general method 4 described earlier.

Purification was by chromatography on silica gel (elution: cyclohexane/ethyl acetate 9:1).

Compound 37

1-[2-methyloxy-4-chlorophenyl]-3-[3,5-dimethyl-4-carboxydimethylmethyloxyphenyl]prop-2-en-1-one

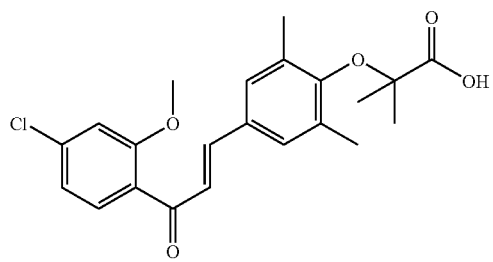

This compound was synthesized from 1-[2-methoxy-4-chlorophenyl]-3-[3,5-dimethyl-4-tertbutyloxycarbonyldimethylmethyloxyphenyl]prop-2-en-1-one (compound 36) according to general method 5 described earlier.

Purification was by chromatography on silica gel (elution: dichloromethane/methanol 98:2)

1H NMR DMSO δ ppm: 1.38 (s, 6H), 2.19 (s, 6H), 3.89 (s, 3H), 7.12 (dd, J=7.98 Hz, J=1.71 Hz, 1H), 7.23 (d, J=15.56 Hz, 1H), 7.29 (s, J=1.71 Hz, 1H), 7.38 (d, J=15.7 Hz, 1H), 7.41 (s, 2H), 7.48 (d, J=7.98 Hz, 1H)

MS (ES-SM): 401.2 (M−1)

Compound 38

1-[4-heptylphenyl]-3-[3,5-dimethyl-4-tertbutyloxycarbonyldimethylmethyloxyphenyl]prop-2-en-1-one

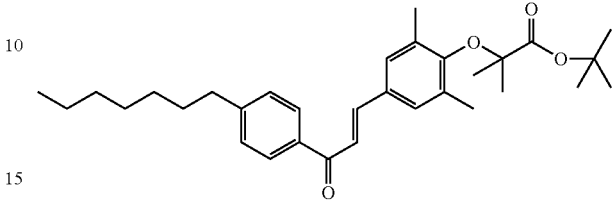

This compound was synthesized from 1-[4-heptylphenyl]-3-[3,5-dimethyl-4-hydroxyphenyl]prop-2-en-1-one (intermediate compound 9) and tertbutyl bromoisobutyrate according to general method 4 described earlier.

Purification was by chromatography on silica gel (elution: cyclohexane/ethyl acetate 9:1)

Compound 39

1-[4-heptylphenyl]-3-[3,5-dimethyl-4-carboxydimethylmethyloxyphenyl]prop-2-en-1-one

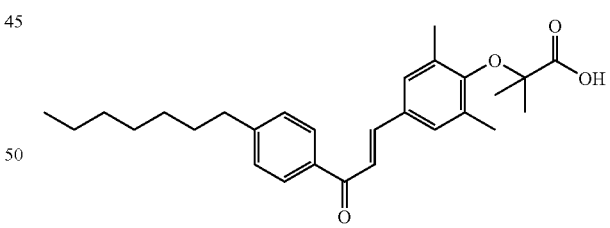

This compound was synthesized from 1-[4-heptylphenyl]-3-[3,5-dimethyl-4-tertbutyloxycarbonyldimethylmethyloxyphenyl]prop-2-en-1-one (compound 38) and tertbutyl bromoisobutyrate according to general method 4 described earlier.

Purification was by chromatography on silica gel (elution: dichloromethane/methanol 98:2)

1H NMR DMSO δ ppm: 0.85 (m, 3H), 1.30-1.24 (m, 8H), 1.39 (s, 6H), 1.60 (m, 2H), 2.22 (s, 6H), 2.67 (t, 2H, J=7.4 Hz), 7.37 (d, J=8.04 Hz, 2H), 7.57 (s, 2H), 7.62 (d, J=15.66 Hz, 1H), 7.82 (d, J=15.69 Hz, 1H), 8.07 (d, J=8.07 Hz, 2H)

MS (ES-MS): 435.3 (M−1)

Compound 40

1-[4-bromophenyl]-3-[3,5-dimethyl-4-tertbutyloxy-carbonyldimethylmethyloxyphenyl]prop-2-en-1-one

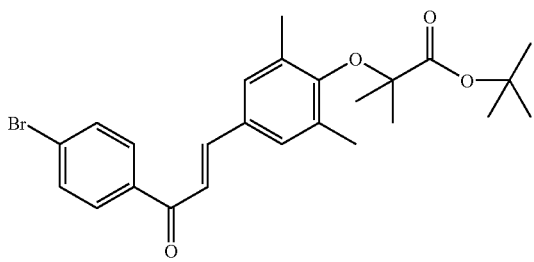

This compound was synthesized from 1-[4-bromophenyl]-3-[3,5-dimethyl-4-hydroxyphenyl]prop-2-en-1-one (intermediate compound 8) and tertbutyl bromoisobutyrate according to general method 4 described earlier.

Purification was by chromatography on silica gel (elution: cyclohexane/ethyl acetate 9:1)

Compound 41

1-[4-bromophenyl]-3-[3,5-dimethyl-4-carboxy dimethylmethyloxyphenyl]prop-2-en-1-one

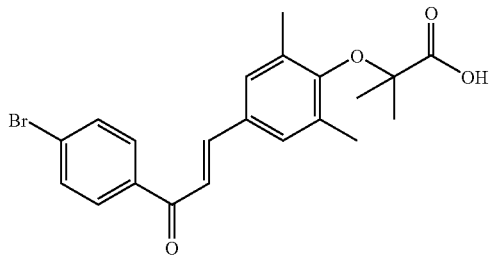

This compound was synthesized from 1-[4-bromophenyl]-3-[3,5-dimethyl-4-tertbutyloxycarbonyldimethyl-methyloxyphenyl]prop-2-en-1-one (compound 40) according to general method 5 described earlier.

Purification was by chromatography on silica gel (elution: dichloromethane/methanol 98:2)

1H NMR DMSO δ ppm: 1.39 (s, 6H), 2.22 (s, 6H), 7.58 (s, 2H), 7.65 (d, J=15.39 Hz, 1H), 7.84-7.77 (m, 3H), 8.09 (d, J=8.19 Hz, 1H), 13.01 (s, 1H)

MS (ES-MS): 417.2 (M−1)

Compound 42

1-[2-hydroxyphenyl]-3-[3,5-dimethyl-4-isopropyloxycarbonyldimethylmethyloxyphenyl]prop-2-en-1-one

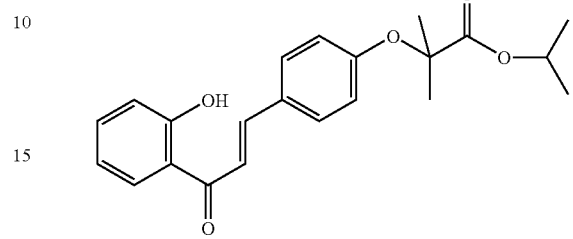

1-[2-hydroxyphenyl]-3-[4-carboxydimethylmethyloxyphenyl]prop-2-en-1-one (compound 4; 1 eq) was dissolved in dichloromethane. Dichloromethylmethyl ether (3 eq) was added and the mixture was kept under reflux for 8 hours. The solvent and excess reagent were eliminated by vacuum evaporation. The evaporation residue was taken up in isopropanol (50 eq) stirred for 12 hours at room temperature and the isopropanol was then eliminated by vacuum evaporation. Purification was by chromatography on silica gel (elution: toluene/ethyl acetate 7:3)

1H NMR CDCl$_3$ δppm: 1.21 (d, J=6.09 Hz, 6H), 1.65 (s, 6H), 5.10 (sept, J=6.10 Hz, 1H), 6.86 (d, J=8.65 Hz, 2H), 6.95 (m, 1H), 7.02 (dd, J=8.65 Hz, J=1.53 Hz, 1H), 7.48 (m, 1H), 7.54 (d, J=15.25 Hz, 1H), 7.57 (d, J=8.65 Hz, 2H), 7.87 (d, J=15.25 Hz, 1H), 7.93 (d, J=8.40 Hz, 1H), 12.94 (signal exchangeable D$_2$O, 1H)

MS (Maldi-Tof): 369.1 (M+1)

Example 2

Evaluation of the Antioxidant Properties of the Inventive Compounds

1. Protection Against LDL Oxidation by Copper:

The inventive compounds which were tested are the compounds whose preparation is described in the above examples.

LDL oxidation is an important alteration and plays a predominant role in the establishment and development of atherosclerosis (Jurgens, Hoff et al. 1987). The following protocol allows to demonstrate the antioxidant properties of compounds. Unless otherwise indicated, the reagents were from Sigma (St Quentin, France).

LDL were prepared according to the method described by Lebeau et al. (Lebeau, Furman et al. 2000).

The solutions of test compounds were prepared at $10^{-2}$ M concentration in bicarbonate buffer (pH 9) and diluted in PBS to obtain final concentrations ranging from 0.1 to 100 µM for a total ethanol concentration of 1% (V/V).

Prior to oxidation, EDTA was removed from the LDL preparation by dialysis. Oxidation then took place at 30° C. by addition of 100 µl of 16.6 µM CuSO$_4$ solution to 160 µL of LDL (125 µg protein/ml) and 20 µl of a test compound solution. The formation of dienes, the species under observation, was followed by measuring optical density at 234 nm in the samples treated with the compounds but in the presence or absence of copper. Optical density at 234 nm was measured every 10 minutes for 8 hours in a thermostated spectrophotometer (Tecan Ultra 380). The analyses were performed in triplicate. The compounds were considered to have antioxidant activity when they induced a longer lag phase and reduced the rate of oxidation and the amount of dienes formed in comparison with the control sample. The inventors demonstrate that the inventive compounds have at least one of the above-described antioxidant properties indicating that the inventive compounds have intrinsic antioxidant activity.

Typical results are given in FIGS. 1-1, 1-2, 1-3, 1-4, 1-5, 1-6, 1-7, 1-8, 1-9, 1-10, 1-11, 1-12, 1-13 and 1-14 illustrating the antioxidant properties of inventive compounds 2, 3, 4, 5, 6, 7, 8, 9, 10, 14, 17, 18, 19, 21, 22, 25, 29, 31, 33, 35, 37, 38 and 41.

2. Evaluation of Protection Conferred by the Inventive Compounds Against Lipid Peroxidation:

The inventive compounds which were tested are the compounds whose preparation is described in the above examples.

LDL oxidation was determined by the TBARS method.

According to the same principle described earlier, LDL were oxidized with $CuSO_4$ and lipid peroxidation was determined as follows:

TBARS were measured by a spectrophotometric method, lipid hydroperoxidation was measured using lipid-dependent peroxidation of iodide to iodine. The results are expressed as nmol of malondialdehyde (MDA) or as nmol of hydroperoxide/mg of protein.

The previous results obtained by measuring inhibition of conjugated diene formation were confirmed by the experiments measuring LDL lipid peroxidation. The inventive compounds also effectively protected LDL against lipid peroxidation induced by copper (oxidizing agent).

Example 3

Measurement of the Antioxidant Properties of the Inventive Compounds on Cell Cultures Culture Protocol:

Neuronal, neuroblastoma (human) and PC12 cells (rat) were the cell lines used for this type of study. PC12 cells were prepared from a pheochromocytoma and Rave been characterized by Greene and Tischler (Greene and Tischler, 1976). These cells are commonly used in studies of neuron differentiation, signal transduction and neuronal death. PC12 cells were grown as previously described (Farinelli, Park et al. 1996) in complete RPMI medium (Invitrogen) supplemented with 10% horse serum and 5% fetal calf serum.

(Primary) cultures of endothelial and smooth muscle cells were also used. Cells were obtained from Promocell (Promocell GmBH, Heidelberg) and cultured according to the supplier's instructions.

The cells were treated with different doses of the compounds ranging from 5 to 300 µM for 24 hours. The cells were then recovered and the increase in expression of the target genes was evaluated by quantitative PCR.

mRNA Measurement:

mRNA was extracted from the cultured cells treated or not with the inventive compounds. Extraction was carried out with the reagents of the Absolutely RNA RT-PCR miniprep kit (Stratagene, France) as directed by the supplier. mRNA was then assayed by spectrometry and quantified by quantitative RT-PCR with a Light Cycler Fast Start DNA Master Sybr Green I kit (Roche) on a Light Cycler System (Roche, France). Primer pairs specific for the genes encoding the antioxidant enzymes superoxide dismutase (SOD), catalase and glutathione peroxidase (GPx) were used as probes. Primer pairs specific for the β-actin and cyclophilin genes were used as control probes.

An increase in mRNA expression of the antioxidant enzyme genes, measured by quantitative RT-PCR, was demonstrated in the different cell types used, when the cells were treated with the inventive compounds.

Control of Oxidative Stress:

Measurement of Oxidizing Species in the Cultured Cells:

The antioxidant properties of the compounds were also evaluated by means of a fluorescent tag the oxidation of which is followed by appearance of a fluorescence signal. The reduction in the intensity of the emitted fluorescence signal was determined in cells treated with the compounds in the following manner: PC12 cells cultured as described earlier (black 96-well plates, transparent bottom, Falcon) were incubated with increasing doses of $H_2O_2$ (0.25 mM-1 mM) in serum-free medium for 2 and 24 hours. After incubation, the medium was removed and the cells were incubated with 10 µM dichlorodihydrofluorescein diacetate solution (DCFDA, Molecular Probes, Eugene, USA) in PBS for 30 min at 37° C. in a 5% $CO_2$ atmosphere. The cells were then rinsed with PBS. The fluorescence emitted by the oxidation tag was measured on a fluorimeter (Tecan Ultra 384) at an excitation wavelength of 495 nm and an emission wavelength of 535 nm. The results are expressed as the percentage of protection relative to the oxidized control.

Fluorescence intensity was lower in the cells incubated with the inventive compounds than in untreated cells. These findings indicate that the inventive compounds promote inhibition of the production of oxidative species in cells subjected to oxidative stress. The previously described antioxidant properties are also effective at inducing antiradical protection in cultured cells.

Measurement of Lipid Peroxidation:

The protective effect of the compounds on lipid peroxidation in cultured cells (cell models noted hereinabove) was determined as follows: the different cell lines and the primary cell cultures were treated as described earlier, the cell supernatant was recovered after treatment and the cells were lysed and recovered for determination of protein concentration. Lipid peroxidation was detected as follows:

Lipid peroxidation was measured by using thiobarbituric acid (TBA) which reacts with lipid peroxidation of aldehydes such as malondialdehyde (MDA). After treatment, the cell supernatant was collected (900 µl) and 90 µl of butylated hydroxytoluene were added (Morliere, Moysan et al. 1991). One milliliter of 0.375% TBA solution in 0.25 M HCl containing 15% trichloroacetic acid was also added to the reaction medium. The mixture was heated at 80° C. for 15 min, cooled on ice and the organic phase was extracted with butanol. The organic phase was analysed by spectrofluorimetry ($\lambda exc=515$ nm and $\lambda em=550$ nm) on a Shimazu 1501 spectrofluorimeter (Shimadzu Corporation, Kyoto, Japan). TBARS are expressed as MDA equivalents using tetra-ethoxypropane as standard. The results were normalized for protein concentration.

The decrease in lipid peroxidation observed in the cells treated with the inventive compounds confirms the previous results.

The inventive compounds advantageously exhibit intrinsic antioxidant properties allowing to slow and/or inhibit the effects of an oxidative stress. The inventors also show that the inventive compounds are capable of inducing the expression of genes encoding antioxidant enzymes. These particular features of the inventive compounds allow cells to more effectively fight against oxidative stress and therefore be protected against free radical-induced damage.

Example 4

Evaluation of PPAR Activation In Vitro by the Inventive Compounds

The inventive compounds having a carboxylic acid function, which were tested, are the compounds whose preparation is described in the above examples.

Nuclear receptors of the PPAR subfamily which are activated by two major pharmaceutical classes—fibrates and glitazones, widely used in the clinic for the treatment of dyslipidemias and diabetes—play an important role in lipid and glucose homeostasis. The following experimental data show that the inventive compounds activate PPARα and PPARγ in vitro.

PPAR activation was tested in vitro in RK13 fibroblast cell lines by measuring the transcriptional activity of chimeras composed of the DNA binding domain of the yeast gal4 transcription factor and the ligand binding domain of the different PPARs. These latter results were then confirmed in cell lines according to the following protocols:

The example is given for RK13 cells.

a. Culture Protocols

RK13 cells were from ECACC (Porton Down, UK) and were grown in DMEM medium supplemented with 10% (V/V) fetal calf serum, 100 U/ml penicillin (Gibco, Paisley, UK) and 2 mM L-glutamine (Gibco, Paisley, UK). The culture medium was changed every two days. Cells were kept at 37° C. in a humidified 95% air/5% $CO_2$ atmosphere.

b. Description of Plasmids Used for Transfection

The plasmids pG5TkpGL3, pRL-CMV, pGal4-hPPARα, pGal4-hPPARγ and pGal4-φ have been described by Raspe, Madsen et al. (1999). The pGal4-mPPARα and pGal4-hPPARγ constructs were obtained by cloning into the pGal4-φ vector of PCR-amplified DNA fragments corresponding to the DEF domains of the human PPARα and PPARγ nuclear receptors.

c. Transfection

RK13 cells were seeded in 24-well culture dishes at $5\times10^4$ cells/well and transfected for 2 hours with the reporter plasmid pG5TkpGL3 (50 ng/well), the expression vectors pGal4-φ, pGal4-mPPARα, pGal4-hPPARα, pGal4-hPPARγ (100 ng/well) and the transfection efficiency control vector pRL-CMV (1 ng/well) according to the previously described protocol (Raspe, Madsen et al. 1999), then incubated for 36 hours with the test compounds. At the end of the experiment, the cells were lysed (Gibco, Paisley, UK) and luciferase activity was determined with a Dual-Luciferase™ Reporter Assay System kit (Promega, Madison, Wis., USA) according to the supplier's instructions as previously described. The protein content of the cell extracts was then measured with the Bio-Rad Protein Assay (Bio-Rad, Munich, Germany) as directed by the supplier.

The inventors demonstrate an increase in luciferase activity in cells treated with the inventive compounds and transfected with the pGal4-hPPARα plasmid. Said induction of luciferase activity indicates that the inventive compounds are activators of PPARα.

The results are given in FIGS. 2-1, 2-2, 2-3, 2-4, 2-5, 2-6 which illustrate the PPARα activator properties of inventive compounds 3, 4, 7, 8, 9, 11, 12, 13, 14, 17, 19, 20, 21, 22, 23, 24, 25, 26, 29, 31, 33, 37, 38, 41.

The inventors demonstrate an increase in luciferase activity in cells treated with the inventive compounds and transfected with the pGal4-hPPARγ plasmid. Said induction of luciferase activity indicates that the inventive compounds are activators of PPARγ.

The results are given in FIG. 2-7 which illustrates the PPARγ activator properties of inventive compounds 17, 33 and 29.

Example 5

Evaluation of the Anti-Inflammatory Properties of the Inventive Compounds

An inflammatory response is observed in many neurological disorders, including multiple sclerosis, Alzheimer's disease and Parkinson's disease, cerebral ischemia and head trauma, and inflammation is also an important factor in neurodegeneration. In stroke, one of the first reactions of glial cells is to release cytokines and free radicals. This release of cytokines and free radicals results in an inflammatory response in the brain which can lead to neuronal death (Rothwell 1997).

Cell lines and primary cells were cultured as described hereinabove.

LPS bacterial endotoxin (*Escherichia coli* 0111:B4) (Sigma, France) was reconstituted in distilled water and stored at 4° C. Cells were treated with LPS 1 µg/ml for 24 hours. To avoid interference from other factors the culture medium was completely changed.

TNF-α is an important factor in the inflammatory response to stress (oxidative stress for example). To evaluate TNF-α secretion in response to stimulation by increasing doses of LPS, the culture medium of stimulated cells was removed and TNF-α was assayed with an ELISA-TNF-α kit (Immunotech, France). Samples were diluted 50-fold so as to be in the range of the standard curve (Chang, Hudson et al. 2000).

The anti-inflammatory property of the compounds was characterized as follows: the cell culture medium was completely changed and the cells were incubated with the test compounds for 2 hours, after which LPS was added to the culture medium at 1 µg/ml final concentration. After a 24-hour incubation, the cell supernatant was recovered and stored at −80° C. when not treated directly. Cells were lysed and protein was quantified with the Bio-Rad Protein Assay kit (Bio-Rad, Munich, Germany) according to the supplier's instructions.

The measurement of the decrease in TNF-α secretion induced by treatment with the test compounds is expressed as pg/ml/µg protein and as the percentage relative to the control. These results show that the inventive compounds have anti-inflammatory properties.

Example 6

Evaluation of the Neuroprotective Effects of the Inventive Compounds in a Cerebral Ischemia-Reperfusion Model Prophylactic Model:
1. Treatments of Animals
1.1 Animals and Administration of the Compounds C57 black/6 mice (wild-type) were used for this experiment.

Animals were maintained on a 12 hour light-dark cycle at a temperature of 20° C.±3° C. Water and food were available ad libitum. Food intake and weight gain were recorded.

The inventive compounds (200 mg/kg/day) or the vehicle (0.5% carboxycellulose (CMC)) were administered to the animals by gavage, for 14 days before ischemia induction in the middle cerebral artery.

1.2 Ischemia Induction-Reperfusion by Intraluminal Occlusion of the Middle Cerebral Artery:

Animals were anesthetized by intraperitoneal injection of 300 mg/kg chloral hydrate. A rectal probe was inserted and body temperature was maintained at 37° C.±0.5° C. Blood pressure was monitored throughout the experiment.

Under a surgical microscope, the right carotid artery was exposed by a median incision in the neck. The pterygopalatine artery was ligated at its origin and an arteriotomy was fashioned in the external carotid artery so as to insert a nylon monofilament, which was gently advanced to the common carotid artery and then into the internal carotid artery so as to occlude the origin of the middle cerebral artery. The filament was withdrawn one hour later to allow reperfusion.

2. Measurement of Brain Infarct Volume:

Twenty-four hours after reperfusion, animals previously treated or not with the compounds were euthanized by pentobarbital overdose.

Brains were rapidly frozen and sliced. Sections were stained with cresyl violet. Unstained zones of the brain sections were considered to be damaged by the infarct. Areas were measured and the volume of the infarct and the two hemispheres was calculated by the following formula: (corrected infarct volume=infarct volume−(volume of right hemisphere−volume of left hemisphere)) to compensate for cerebral oedema.

Analysis of the brain sections from treated animals revealed a marked decrease in infarct volume as compared with untreated animals. When the inventive compounds were administered to the animals before the ischemia (prophylactic effect), they were capable of inducing neuroprotection.

An example of the results is given in FIG. 3-1 which illustrates the prophylactic neuroprotective properties of inventive compounds 15 and 42.

3. Measurement of Antioxidant Enzyme Activity:

The mouse brains were frozen, crushed and reduced to powder, then resuspended in saline solution. The different enzyme activities were then measured as described by the following authors: superoxide dismutase (Flohe and Otting 1984); glutathione peroxidase (Paglia and Valentine 1967); glutathione reductase (Spooner, Delides et al. 1981); glutathione-S-transferase (Habig and Jakoby 1981); catalase (Aebi 1984).

Said different enzyme activities were increased in brain preparations from animals treated with the inventive compounds.

Curative or Acute Phase Treatment Model

1. Ischemia Induction/Reperfusion by Intraluminal Occlusion of the Middle Cerebral Artery.

Animals such as those described previously were used for this experiment. Animals were anesthetized by intraperitoneal injection of 300 mg/kg chloral hydrate. A rectal probe was inserted and body temperature was maintained at 37° C.±0.5° C. Blood pressure was monitored throughout the experiment.

Under a surgical microscope, the right carotid artery was exposed by a median incision in the neck. The pterygopalatine artery was ligated at its origin and an arteriotomy was fashioned in the external carotid artery so as to insert a nylon monofilament, which was gently advanced to the common carotid artery and then into the internal carotid artery so as to occlude the origin of the middle cerebral artery. The filament was withdrawn one hour later to allow reperfusion.

2. Treatment of Animals:

Animals first subjected to ischemia-reperfusion were treated with the inventive compounds by the oral or systemic route one or more times after reperfusion.

3. Measurement of Brain Infarct Volume:

Seventy-two hours after reperfusion, animals previously treated or not with the compounds were euthanized by pentobarbital overdose.

Brains were rapidly frozen and sliced. Sections were stained with cresyl violet. Unstained zones of the brain sections were considered to be damaged by the infarct. Areas were measured and the volume of the infarct and the two hemispheres was calculated by the following formula: (corrected infarct volume=infarct volume−(volume of right hemisphere−volume of left hemisphere)) to compensate for cerebral oedema.

In the case of curative treatment (treatment of the acute phase), animals treated with the inventive compounds had fewer brain lesions than untreated animals. In fact, the infarct volume was smaller when the inventive compounds were administered one or more times after ischemia-reperfusion.

An example of the results is given in FIG. 3-2 which illustrates the acute neuroprotective properties of inventive compounds 15 and 42.

The use of the inventive compounds in different experimental models shows that said novel compounds have intrinsic antioxidant activity, are capable of delaying and reducing the effects of an oxidative stress, and furthermore also induce the expression of genes coding for antioxidant enzymes which together with their antioxidant nature reinforces the protection against free radicals in cell cultures. In addition, the inventive compounds also exhibit anti-inflammatory activity and are capable of activating the PPARα. nuclear receptor Finally, use of the inventive compounds, containing an ester function or a carboxylic acid function, in an animal ischemia-reperfusion model revealed the beneficial neuroprotective effect of both preventive and curative treatment.

Bibliography

Adams, H. P., Jr. (2002). "Emergent use of anticoagulation for treatment of patients with ischemic stroke." *Stroke* 33(3): 856-61.

Aebi, H. (1984). "Catalase in vitro." *Methods Enzymol* 105: 121-6.

Bordet, R., D. Deplanque, et al. (2000). "Increase in endogenous brain superoxide dismutase as a potential mechanism of lipopolysaccharide-induced brain ischemic tolerance." *J Cereb Blood Flow Metab* 20(8): 1190-6.

Chabrier, P. E., M. Auguet, et al. (1999). "BN 80933, a dual inhibitor of neuronal nitric oxide synthase and lipid peroxidation: a promising neuroprotective strategy." *Proc Natl Acad Sci USA* 96(19): 10824-9.

Chang, R. C., P. Hudson, et al. (2000). "Influence of neurons on lipopolysaccharide-stimulated production of nitric oxide and tumor necrosis factor-alpha by cultured glia." *Brain Res* 853(2): 236-44.

Clark, R. B. (2002). "The role of PPARs in inflammation and immunity." *J Leukoc Biol* 71(3): 388-400.

Dimagl, U., C. Iadecola, et al. (1999). "Pathobiology of ischaemic stroke: an integrated view." *Trends Neurosci* 22(9): 391-7.

Ellis, C. N., J. Varani, et al. (2000). "Troglitazone improves psoriasis and normalizes models of proliferative skin dis-

The invention claimed is:
1. A compound of formula (I)

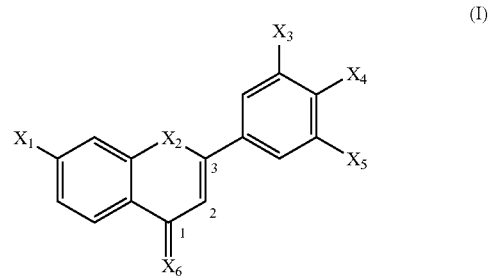

in which:
X$_1$ is a halogen, R1 or -G1-R1,
X$_2$ is hydrogen, hydroxy or an unsubstituted alkyloxy,
X$_3$ is —R3 or -G3-R3,
X$_4$ is a —R4 or -G4-R4,
X$_5$ is —R5 or -G5-R5,
X$_6$ is oxygen,
R1, R3 and R5, which are the same or different, are an unsubstituted alkyl having from one to seven carbon atoms,
R4 is an alkyl having from one to seven carbon atoms substituted by a group 1 substituent,
G1, G3, G4, and G5, which are the same or different, are oxygen or sulphur wherein at least one of X$_1$, X$_3$, X$_4$ and X$_5$ is G1R1, G3R3, G4R4 and G5R5, respectively,
said group 1 substituent being selected from the group consisting of —COOR$_6$ and —CONR$_6$R$_7$,
wherein R$_6$ and R$_7$, which are the same or different, are hydrogen or an unsubstituted alkyl having from one to seven carbon atoms, or an optical isomer, a geometric isomer, a racemate, a tautomer, a salt or mixtures thereof.

2. The compound of according to claim 1, wherein both G1 and G4 are sulfur.

3. The compound according to claim 1, wherein X$_2$ is hydrogen.

4. The compound according to claim 1, wherein X$_1$ is -G1-R1.

5. The compound according to claim 1, wherein X$_1$ is -G1-R1 and G1 is oxygen.

6. The compound according to claim 1, wherein X$_1$ is -G1-R1 and G1 is sulfur.

7. The compound according to claim 1, wherein X$_4$ is -G4-R4 group.

8. The compound according to claim 1, wherein X$_4$ is -G4-R4 and G4 is oxygen.

9. The compound according to claim 1, wherein G4 is an oxygen atom, and X$_3$ and X$_5$ respectively represent R3 and R5, wherein R3 and R5 are alkyl groups having one or two carbon atoms.

10. The compound according to claim 1 wherein X$_1$ is a halogen.

11. The compound according to claim 1, wherein X$_4$ is OC(CH$_3$)$_2$COOR$_6$.

12. The compound according to claim 1, wherein $X_4$ represents $SC(CH_3)_2COOR_6$.

13. A compound selected in the group consisting of:
1-[2-hydroxy-4-chlorophenyl]-3-[3,5-dimethoxy-4-carboxydimethylmethyloxyphenyl]prop-2-en-1-one,
1-[2-hydroxy-4-chlorophenyl]-3-[3,5-dimethoxy-4-isopropyloxycarbonyldimethylmethyloxyphenyl]prop-2-en-1-one,
1-[2-hydroxy-4-chlorophenyl]-3-[3,5-dimethyl-4-carboxydimethylmethyloxyphenyl]prop-2-en-1-one,
1-[2-hydroxy-4-chlorophenyl]-3-[3,5-dimethyl-4-isopropyloxycarbonyldimethylmethyloxyphenyl]prop-2-en-1-one,
1-[4-chlorophenyl]-3-[3,5-dimethyl-4-tertbutyloxycarbonyldimethylmethyloxyphenyl]prop-2-en-1-one,
1-[4-chlorophenyl]-3-[3,5-dimethyl-4-isopropyloxycarbonyldimethylmethyloxyphenyl]prop-2-en-1-one,
1-[4-chlorophenyl]-3-[3,5-dimethyl-4-carboxydimethylmethyloxyphenyl]prop-2-en-1-one,
1-[2-hydroxy-4-bromophenyl]-3-[3,5-dimethyl-4-carboxydimethylmethyloxyphenyl]prop-2-en-1-one,
1-[4-methylthiophenyl]-3-[3,5-dimethyl-4-tertbutyloxycarbonyldimethylmethyloxyphenyl]prop-2-en-1-one,
1-[4-methylthiophenyl]-3-[3,5-dimethyl-4-isopropyloxycarbonyldimethylmethyloxyphenyl]prop-2-en-1-one,
1-[4-methylthiophenyl]-3-[3,5-dimethyl-4-carboxydimethylmethyloxyphenyl]prop-2-en-1-one,
1-[4-hexyloxyphenyl]-3-[3,5-dimethyl-4-tertbutyloxycarbonyldimethylmethyloxyphenyl]prop-2-en-1-one,
1-[4-hexyloxyphenyl]-3-[3,5-dimethyl-4-carboxydimethylmethyloxyphenyl]prop-2-en-1-one,
1-[2-methyloxy-4-chlorophenyl]-3-[3,5-dimethyl-4-tertbutyloxycarbonyldimethylmethyloxyphenyl]prop-2-en-1-one,
1-[2-methyloxy-4-chlorophenyl]-3-[3,5-dimethyl-4-carboxydimethylmethyloxyphenyl]prop-2-en-1-one,
1-[4-heptylphenyl]-3-[3,5-dimethyl-4-tertbutyloxycarbonyldimethylmethyloxyphenyl]prop-2-en-1-one,
1-[4-heptylphenyl]-3-[3,5-dimethyl-4-carboxydimethylmethyloxyphenyl]prop-2-en-1-one,
1-[4-bromophenyl]-3-[3,5-dimethyl-4-tertbutyloxycarbonyldimethylmethyloxyphenyl]prop-2-en-1-one, and
1-[4-bromophenyl]-3-[3,5-dimethyl-4-carboxydimethylmethyloxyphenyl]prop-2-en-1-one.

14. A compound selected in the group consisting of:
1-[4-methylthiophenyl]-3-[3,5-dimethyl-4-carboxydimethylmethyloxyphenyl]prop-2-en-1-one,
1-[4-hexyloxyphenyl]-3-[3,5-dimethyl-4-carboxydimethylmethyloxyphenyl]prop-2-en-1-one, and
1-[4-bromophenyl]-3-[3,5-dimethyl-4-carboxydimethylmethyloxyphenyl]prop-2-en-1-one.

15. A method for preparing a compound of claim 1, comprising contacting in basic or acidic medium at least one compound corresponding to formula (A) with at least one compound corresponding to formula (B):

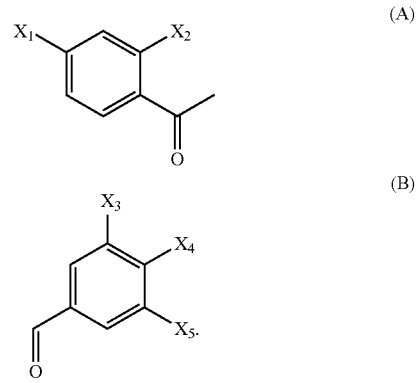

16. A pharmaceutical composition comprising, in a pharmaceutically acceptable support, at least one compound of claim 1.

17. A pharmaceutical composition comprising, in a pharmaceutically acceptable support, at least one compound of claim 1, in a form for the treatment of a cerebral ischemia.

* * * * *